United States Patent
Katus et al.

(10) Patent No.: US 10,792,329 B2
(45) Date of Patent: Oct. 6, 2020

(54) S100 BASED TREATMENT OF CARDIAC POWER FAILURE

(71) Applicant: Ruprecht-Karls-Universitat Heidelberg, Heidelberg (DE)

(72) Inventors: Hugo Katus, Heidelberg (DE); Patrick Most, Heidelberg (DE)

(73) Assignee: RUPRECHT-KARLS-UNIVERSITÄT HEIDELBERG, Heidelberg (DE)

( * ) Notice: Subject to any disclaimer, the term of this patent is extended or adjusted under 35 U.S.C. 154(b) by 0 days.

(21) Appl. No.: 15/026,116

(22) PCT Filed: Oct. 1, 2014

(86) PCT No.: PCT/EP2014/071024
§ 371 (c)(1),
(2) Date: Mar. 30, 2016

(87) PCT Pub. No.: WO2015/049277
PCT Pub. Date: Apr. 9, 2015

(65) Prior Publication Data
US 2016/0228504 A1    Aug. 11, 2016

(30) Foreign Application Priority Data
Oct. 1, 2013  (EP) .................... 13186913

(51) Int. Cl.
| | | |
|---|---|---|
| *A61K 38/17* | (2006.01) | |
| *A61K 48/00* | (2006.01) | |
| *C07K 14/47* | (2006.01) | |
| *A61K 38/04* | (2006.01) | |
| *A61K 38/08* | (2019.01) | |
| *C12N 7/00* | (2006.01) | |

(52) U.S. Cl.
CPC .......... *A61K 38/1709* (2013.01); *A61K 38/04* (2013.01); *A61K 38/08* (2013.01); *A61K 48/005* (2013.01); *A61K 48/0058* (2013.01); *C07K 14/4702* (2013.01); *C12N 7/00* (2013.01); *C12N 2750/14121* (2013.01); *C12N 2750/14132* (2013.01); *C12N 2750/14143* (2013.01); *C12N 2750/14171* (2013.01)

(58) Field of Classification Search
CPC .... A61K 38/1709; A61K 38/04; A61K 38/08; A61K 48/005; A61K 48/0058; C07K 14/4702; C12N 7/00; C12N 2750/14121; C12N 2750/14132; C12N 2750/14143; C12N 2750/14171

See application file for complete search history.

(56) References Cited

U.S. PATENT DOCUMENTS 7,588,756 B1    9/2009  Katus et al.
2012/0129758 A1    5/2012  Most et al.

FOREIGN PATENT DOCUMENTS

WO    2011/092285    8/2011

OTHER PUBLICATIONS

Pleger et al., Sci. Transl. Med., 3(92): 1-20, 2011.*
Pleger, Sven et al. "Stable myocardial-specific AAV6-S100A1 gene therapy results in chronic functional heart failure rescue" Circulation (2007), vol. 115(19), pp. 2506-2515.
Most, Patrick et al. "S100A1: a novel inotropic regulator of cardiac performance. Transition from molecular physiology to pathophysiological relevance" American Journal of Physiology: Regulatory, Integrative and Comparative Physiology (2007), vol. 293(2) pp. R568-R577.
Volkers, Mirko et al., "S100A1 decreases calcium spark frequency and alters their spatial characteristics in permeabilized adult ventricular cardiomyocytes" Cell Calcium (2007) vol. 41(2) pp. 135-143.
The International Search Report (ISR) for PCT/EP2014/071024 dated Jan. 20, 2015, pp. 1-5.
The Written Opinion of the International Searching Authority for PCT/EP2014/071024 dated Jan. 20, 2015, pp. 1-6.
Doevendans et al., "Cardiovascular phenotyping in mice" Cardiovascular Research 39:34-49 (1998).
Garg et al., "A gross comparative anatomical study of hearts in human cadavers and pigs" IJMDS 2(2):170-177 (Jul. 2013).
Piao et al., "Change Trends of Organ Weight Background Data in Sprague Dawley Rats at Different Ages" J Tox Pathol. 26:29-34 (2013).

* cited by examiner

*Primary Examiner* — Thaian N. Ton
(74) *Attorney, Agent, or Firm* — McDonnell Boehnen Hulbert & Berghoff LLP

(57) ABSTRACT

The present invention relates to S100 protein and nuclei acids encoding S100 protein for enhancing the cardiac power as well as vectors and pharmaceuticals comprising the same and uses thereof.

8 Claims, 9 Drawing Sheets

Figure 1:
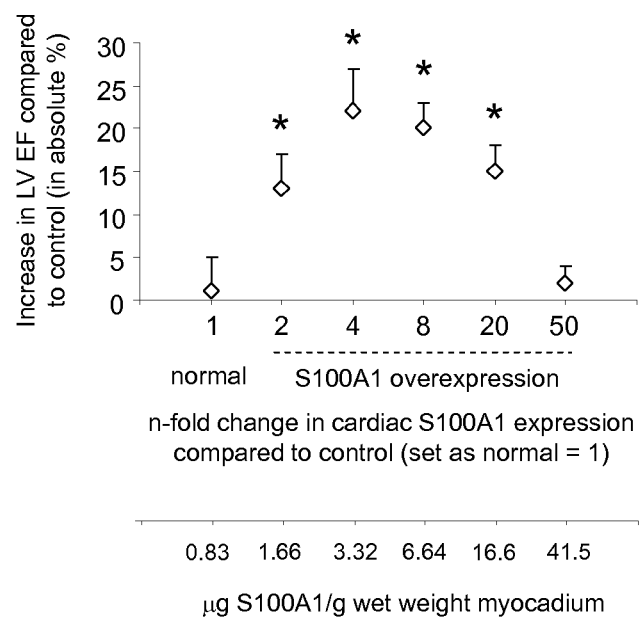

Specification includes a Sequence Listing.

SEQUENCE LISTING

<160> NUMBER OF SEQ ID NOS: 394

<210> SEQ ID NO 1
<211> LENGTH: 4
<212> TYPE: PRT
<213> ORGANISM: Artificial Sequence
<220> FEATURE:
<223> OTHER INFORMATION: core motif variants
<220> FEATURE:
<221> NAME/KEY: VARIANT
<222> LOCATION: (1)..(1)

```
<223> OTHER INFORMATION: Xaa at position 1 may be valine, isoleucine or
      methionin
<220> FEATURE:
<221> NAME/KEY: VARIANT
<222> LOCATION: (2)..(2)
<223> OTHER INFORMATION: Xaa at position 2 may be alanine, glycine or
      serine
<220> FEATURE:
<221> NAME/KEY: VARIANT
<222> LOCATION: (3)..(3)
<223> OTHER INFORMATION: Xaa at position 3 may be alanine or valine

<400> SEQUENCE: 1

Xaa Xaa Xaa Leu
1

<210> SEQ ID NO 2
<211> LENGTH: 10
<212> TYPE: PRT
<213> ORGANISM: Artificial
<220> FEATURE:
<223> OTHER INFORMATION: variable peptide based on amino acids 76 to 85
      of human S100A1
<220> FEATURE:
<221> NAME/KEY: VARIANT
<222> LOCATION: (1)..(1)
<223> OTHER INFORMATION: Xaa at position 1 may be valine or isoleucine
<220> FEATURE:
<221> NAME/KEY: VARIANT
<222> LOCATION: (2)..(2)
<223> OTHER INFORMATION: Xaa at position 2 may be valine 2 or isoleucine
<220> FEATURE:
<221> NAME/KEY: VARIANT
<222> LOCATION: (3)..(3)
<223> OTHER INFORMATION: Xaa at position 3 may be leucine or methionine
<220> FEATURE:
<221> NAME/KEY: VARIANT
<222> LOCATION: (4)..(4)
<223> OTHER INFORMATION: Xaa at position 4 may be valine, isoleucine
      or methionine
<220> FEATURE:
<221> NAME/KEY: VARIANT
<222> LOCATION: (5)..(5)
<223> OTHER INFORMATION: Xaa at position 5 may be alanine, glycine or
      serine
<220> FEATURE:
<221> NAME/KEY: VARIANT
<222> LOCATION: (6)..(6)
<223> OTHER INFORMATION: Xaa at position 6 may be alanine or valine
<220> FEATURE:
<221> NAME/KEY: VARIANT
<222> LOCATION: (8)..(8)
<223> OTHER INFORMATION: Xaa at position 8 may be threonine or alanine
<220> FEATURE:
<221> NAME/KEY: VARIANT
<222> LOCATION: (9)..(9)
<223> OTHER INFORMATION: Xaa at position 9 may be valine, alanine or
      isoleucine
<220> FEATURE:
<221> NAME/KEY: VARIANT
<222> LOCATION: (10)..(10)
<223> OTHER INFORMATION: Xaa at position 10 may be alanine, methionine
      or valine

<400> SEQUENCE: 2

Xaa Xaa Xaa Xaa Xaa Xaa Leu Xaa Xaa Xaa
1               5                   10

<210> SEQ ID NO 3
<211> LENGTH: 6
<212> TYPE: PRT
<213> ORGANISM: Artificial Sequence
<220> FEATURE:
<223> OTHER INFORMATION: hydrophilic motif
<220> FEATURE:
```

```
<221> NAME/KEY: VARIANT
<222> LOCATION: (1)..(1)
<223> OTHER INFORMATION: Xaa at position 1 may be aspartic acid or
      glutamic acid
<220> FEATURE:
<221> NAME/KEY: VARIANT
<222> LOCATION: (2)..(2)
<223> OTHER INFORMATION: Xaa at position 2 may be lysine or arginine
<220> FEATURE:
<221> NAME/KEY: VARIANT
<222> LOCATION: (3)..(3)
<223> OTHER INFORMATION: Xaa at position 3 may be aspartic acid or
      glutamic acid
<220> FEATURE:
<221> NAME/KEY: VARIANT
<222> LOCATION: (4)..(4)
<223> OTHER INFORMATION: Xaa at position 4 may be aspartic acid or
      glutamic acid
<220> FEATURE:
<221> NAME/KEY: VARIANT
<222> LOCATION: (5)..(5)
<223> OTHER INFORMATION: Xaa at position 5 may be proline or glycine
<220> FEATURE:
<221> NAME/KEY: VARIANT
<222> LOCATION: (6)..(6)
<223> OTHER INFORMATION: Xaa at position 6 may be proline or glycine

<400> SEQUENCE: 3

Xaa Xaa Xaa Xaa Xaa Xaa
1               5

<210> SEQ ID NO 4
<211> LENGTH: 4
<212> TYPE: PRT
<213> ORGANISM: Artificial Sequence
<220> FEATURE:
<223> OTHER INFORMATION: core motif variant

<400> SEQUENCE: 4

Val Gly Ala Leu
1

<210> SEQ ID NO 5
<211> LENGTH: 4
<212> TYPE: PRT
<213> ORGANISM: Artificial Sequence
<220> FEATURE:
<223> OTHER INFORMATION: core motif variant

<400> SEQUENCE: 5

Ile Ala Ala Leu
1

<210> SEQ ID NO 6
<211> LENGTH: 4
<212> TYPE: PRT
<213> ORGANISM: Artificial Sequence
<220> FEATURE:
<223> OTHER INFORMATION: core motif variant

<400> SEQUENCE: 6

Val Ser Val Leu
1

<210> SEQ ID NO 7
<211> LENGTH: 4
<212> TYPE: PRT
<213> ORGANISM: Artificial Sequence
<220> FEATURE:
<223> OTHER INFORMATION: core motif variant
```

```
<400> SEQUENCE: 7

Met Gly Ala Leu
1

<210> SEQ ID NO 8
<211> LENGTH: 4
<212> TYPE: PRT
<213> ORGANISM: Artificial Sequence
<220> FEATURE:
<223> OTHER INFORMATION: core motif variant

<400> SEQUENCE: 8

Val Ala Ala Leu
1

<210> SEQ ID NO 9
<211> LENGTH: 10
<212> TYPE: PRT
<213> ORGANISM: Artificial
<220> FEATURE:
<223> OTHER INFORMATION: amino acids 76 to 85 of human S100A1

<400> SEQUENCE: 9

Val Val Leu Val Ala Ala Leu Thr Val Ala
1               5                   10

<210> SEQ ID NO 10
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 10

Val Ile Leu Val Ala Ala Leu Thr Val Ala
1               5                   10

<210> SEQ ID NO 11
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 11

Val Val Met Val Ala Ala Leu Thr Val Ala
1               5                   10

<210> SEQ ID NO 12
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 12

Ile Ile Leu Val Gly Ala Leu Thr Val Ala
1               5                   10

<210> SEQ ID NO 13
<211> LENGTH: 10
<212> TYPE: PRT
<213> ORGANISM: Artificial
<220> FEATURE:
```

```
<223> OTHER INFORMATION: peptide variant based on amino acids 76 to 85
      of human S100A1

<400> SEQUENCE: 13

Val Val Leu Ile Ala Ala Leu Ala Ala Ala
1               5                   10

<210> SEQ ID NO 14
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 14

Val Ile Leu Val Ser Val Leu Thr Val Ala
1               5                   10

<210> SEQ ID NO 15
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 15

Ile Ile Leu Met Gly Ala Leu Thr Val Ala
1               5                   10

<210> SEQ ID NO 16
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 16

Val Val Met Val Ala Ala Leu Thr Val Val
1               5                   10

<210> SEQ ID NO 17
<211> LENGTH: 6
<212> TYPE: PRT
<213> ORGANISM: Artificial
<220> FEATURE:
<223> OTHER INFORMATION: hydrophilic motif

<400> SEQUENCE: 17

Asp Lys Asp Asp Pro Pro
1               5

<210> SEQ ID NO 18
<211> LENGTH: 9
<212> TYPE: PRT
<213> ORGANISM: Artificial Sequence
<220> FEATURE:
<223> OTHER INFORMATION: S100A1 protein derived domain variant

<400> SEQUENCE: 18

Val Val Leu Val Ala Ala Leu Thr Val
1               5

<210> SEQ ID NO 19
<211> LENGTH: 8
```

```
<212> TYPE: PRT
<213> ORGANISM: Artificial Sequence
<220> FEATURE:
<223> OTHER INFORMATION: S100A1 protein derived domain variant

<400> SEQUENCE: 19

Val Val Leu Val Ala Ala Leu Thr
1               5

<210> SEQ ID NO 20
<211> LENGTH: 7
<212> TYPE: PRT
<213> ORGANISM: Artificial Sequence
<220> FEATURE:
<223> OTHER INFORMATION: S100A1 protein derived domain variant

<400> SEQUENCE: 20

Val Val Leu Val Ala Ala Leu
1               5

<210> SEQ ID NO 21
<211> LENGTH: 9
<212> TYPE: PRT
<213> ORGANISM: Artificial Sequence
<220> FEATURE:
<223> OTHER INFORMATION: S100A1 protein derived domain variant

<400> SEQUENCE: 21

Val Leu Val Ala Ala Leu Thr Val Ala
1               5

<210> SEQ ID NO 22
<211> LENGTH: 8
<212> TYPE: PRT
<213> ORGANISM: Artificial Sequence
<220> FEATURE:
<223> OTHER INFORMATION: S100A1 protein derived domain variant

<400> SEQUENCE: 22

Val Leu Val Ala Ala Leu Thr Val
1               5

<210> SEQ ID NO 23
<211> LENGTH: 7
<212> TYPE: PRT
<213> ORGANISM: Artificial Sequence
<220> FEATURE:
<223> OTHER INFORMATION: S100A1 protein derived domain variant

<400> SEQUENCE: 23

Val Leu Val Ala Ala Leu Thr
1               5

<210> SEQ ID NO 24
<211> LENGTH: 6
<212> TYPE: PRT
<213> ORGANISM: Artificial Sequence
<220> FEATURE:
<223> OTHER INFORMATION: S100A1 protein derived domain variant

<400> SEQUENCE: 24

Val Leu Val Ala Ala Leu
1               5

<210> SEQ ID NO 25
<211> LENGTH: 8
<212> TYPE: PRT
```

<213> ORGANISM: Artificial Sequence
<220> FEATURE:
<223> OTHER INFORMATION: S100A1 protein derived domain variant

<400> SEQUENCE: 25

Leu Val Ala Ala Leu Thr Val Ala
1               5

<210> SEQ ID NO 26
<211> LENGTH: 7
<212> TYPE: PRT
<213> ORGANISM: Artificial Sequence
<220> FEATURE:
<223> OTHER INFORMATION: S100A1 protein derived domain variant

<400> SEQUENCE: 26

Leu Val Ala Ala Leu Thr Val
1               5

<210> SEQ ID NO 27
<211> LENGTH: 6
<212> TYPE: PRT
<213> ORGANISM: Artificial Sequence
<220> FEATURE:
<223> OTHER INFORMATION: S100A1 protein derived domain variant

<400> SEQUENCE: 27

Leu Val Ala Ala Leu Thr
1               5

<210> SEQ ID NO 28
<211> LENGTH: 5
<212> TYPE: PRT
<213> ORGANISM: Artificial Sequence
<220> FEATURE:
<223> OTHER INFORMATION: S100A1 protein derived domain variant

<400> SEQUENCE: 28

Leu Val Ala Ala Leu
1               5

<210> SEQ ID NO 29
<211> LENGTH: 7
<212> TYPE: PRT
<213> ORGANISM: Artificial Sequence
<220> FEATURE:
<223> OTHER INFORMATION: S100A1 protein derived domain variant

<400> SEQUENCE: 29

Val Ala Ala Leu Thr Val Ala
1               5

<210> SEQ ID NO 30
<211> LENGTH: 6
<212> TYPE: PRT
<213> ORGANISM: Artificial Sequence
<220> FEATURE:
<223> OTHER INFORMATION: S100A1 protein derived domain variant

<400> SEQUENCE: 30

Val Ala Ala Leu Thr Val
1               5

<210> SEQ ID NO 31
<211> LENGTH: 5
<212> TYPE: PRT
<213> ORGANISM: Artificial Sequence

```
<220> FEATURE:
<223> OTHER INFORMATION: S100A1 protein derived domain variant

<400> SEQUENCE: 31

Val Ala Ala Leu Thr
1               5

<210> SEQ ID NO 32
<211> LENGTH: 15
<212> TYPE: PRT
<213> ORGANISM: Artificial Sequence
<220> FEATURE:
<223> OTHER INFORMATION: Functional peptide (Fig. 26)

<400> SEQUENCE: 32

Asp Lys Asp Asp Pro Pro Val Leu Val Ala Ala Leu Thr Val Ala
1               5                   10                  15

<210> SEQ ID NO 33
<211> LENGTH: 14
<212> TYPE: PRT
<213> ORGANISM: Artificial Sequence
<220> FEATURE:
<223> OTHER INFORMATION: Functional peptide (Fig. 26)

<400> SEQUENCE: 33

Asp Lys Asp Asp Pro Pro Leu Val Ala Ala Leu Thr Val Ala
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Functional peptide (Fig. 26)

<400> SEQUENCE: 34

Asp Lys Asp Asp Pro Pro Val Ala Ala Leu Thr Val Ala
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Functional peptide (Fig. 26)

<400> SEQUENCE: 35

Asp Lys Asp Asp Pro Pro Val Val Leu Val Ala Ala Leu Thr Val
1               5                   10                  15

<210> SEQ ID NO 36
<211> LENGTH: 14
<212> TYPE: PRT
<213> ORGANISM: Artificial Sequence
<220> FEATURE:
<223> OTHER INFORMATION: Functional peptide (Fig. 26)

<400> SEQUENCE: 36

Asp Lys Asp Asp Pro Pro Val Val Leu Val Ala Ala Leu Thr
1               5                   10

<210> SEQ ID NO 37
<211> LENGTH: 13
<212> TYPE: PRT
<213> ORGANISM: Artificial Sequence
<220> FEATURE:
```

<223> OTHER INFORMATION: Functional peptide (Fig. 26)

<400> SEQUENCE: 37

Asp Lys Asp Asp Pro Pro Val Val Leu Val Ala Ala Leu
1               5                   10

<210> SEQ ID NO 38
<211> LENGTH: 94
<212> TYPE: PRT
<213> ORGANISM: Homo sapiens

<400> SEQUENCE: 38

Met Gly Ser Glu Leu Glu Thr Ala Met Glu Thr Leu Ile Asn Val Phe
1               5                   10                  15

His Ala His Ser Gly Lys Glu Gly Asp Lys Tyr Lys Leu Ser Lys Lys
            20                  25                  30

Glu Leu Lys Glu Leu Leu Gln Thr Glu Leu Ser Gly Phe Leu Asp Ala
        35                  40                  45

Gln Lys Asp Val Asp Ala Val Asp Lys Val Met Lys Glu Leu Asp Glu
    50                  55                  60

Asn Gly Asp Gly Glu Val Asp Phe Gln Glu Tyr Val Val Leu Val Ala
65                  70                  75                  80

Ala Leu Thr Val Ala Cys Asn Asn Phe Phe Trp Glu Asn Ser
                85                  90

<210> SEQ ID NO 39
<211> LENGTH: 20
<212> TYPE: PRT
<213> ORGANISM: Artificial
<220> FEATURE:
<223> OTHER INFORMATION: amino acids 75 to 94 of human S100A1

<400> SEQUENCE: 39

Tyr Val Val Leu Val Ala Ala Leu Thr Val Ala Cys Asn Asn Phe Phe
1               5                   10                  15

Trp Glu Asn Ser
            20

<210> SEQ ID NO 40
<211> LENGTH: 15
<212> TYPE: PRT
<213> ORGANISM: Artificial
<220> FEATURE:
<223> OTHER INFORMATION: amino acids 2 to 16 of human S100A1

<400> SEQUENCE: 40

Gly Ser Glu Leu Glu Thr Ala Met Glu Thr Leu Ile Asn Val Phe
1               5                   10                  15

<210> SEQ ID NO 41
<211> LENGTH: 13
<212> TYPE: PRT
<213> ORGANISM: Artificial
<220> FEATURE:
<223> OTHER INFORMATION: amino acids 42 to 54 of human S100A1

<400> SEQUENCE: 41

Leu Ser Gly Phe Leu Asp Ala Gln Lys Asp Val Asp Ala
1               5                   10

<210> SEQ ID NO 42
<211> LENGTH: 17
<212> TYPE: PRT

-continued

```
<213> ORGANISM: Artificial
<220> FEATURE:
<223> OTHER INFORMATION: amino acids 75 to 85 of human S100A1 fused to a
      hydrophilic motif

<400> SEQUENCE: 42

Asp Lys Asp Asp Pro Pro Tyr Val Val Leu Val Ala Ala Leu Thr Val
1               5                   10                  15
Ala

<210> SEQ ID NO 43
<211> LENGTH: 11
<212> TYPE: PRT
<213> ORGANISM: Artificial
<220> FEATURE:
<223> OTHER INFORMATION: amino acids 75 to 85 of human S100A1

<400> SEQUENCE: 43

Tyr Val Val Leu Val Ala Ala Leu Thr Val Ala
1               5                   10

<210> SEQ ID NO 44
<211> LENGTH: 12
<212> TYPE: PRT
<213> ORGANISM: Artificial
<220> FEATURE:
<223> OTHER INFORMATION: amino acids 75 to 80 of human S100A1 fused to a
      hydrophilic motif

<400> SEQUENCE: 44

Asp Lys Asp Asp Pro Pro Tyr Val Val Leu Val Ala
1               5                   10

<210> SEQ ID NO 45
<211> LENGTH: 12
<212> TYPE: PRT
<213> ORGANISM: Artificial
<220> FEATURE:
<223> OTHER INFORMATION: amino acids 80 to 85 of human S100A1 protein
      fused to a hydrophilic motif

<400> SEQUENCE: 45

Asp Lys Asp Asp Pro Pro Ala Ala Leu Thr Val Ala
1               5                   10

<210> SEQ ID NO 46
<211> LENGTH: 17
<212> TYPE: PRT
<213> ORGANISM: Artificial
<220> FEATURE:
<223> OTHER INFORMATION: amino acids 75 to 85 of S100A4 fused to a
      hydrophilic motif

<400> SEQUENCE: 46

Asp Lys Asp Asp Pro Pro Tyr Cys Val Phe Leu Ser Cys Ile Ala Met
1               5                   10                  15
Met

<210> SEQ ID NO 47
<211> LENGTH: 17
<212> TYPE: PRT
<213> ORGANISM: Artificial
<220> FEATURE:
<223> OTHER INFORMATION: amino acids 75 to 85 of S100B fused to a
      hydrophilic motif

<400> SEQUENCE: 47
```

Asp Lys Asp Asp Pro Pro Phe Met Ala Phe Val Ala Met Val Thr Thr
1               5                   10                  15

Ala

<210> SEQ ID NO 48
<211> LENGTH: 6
<212> TYPE: PRT
<213> ORGANISM: Artificial
<220> FEATURE:
<223> OTHER INFORMATION: hydrophilic motif

<400> SEQUENCE: 48

Glu Lys Asp Asp Pro Pro
1               5

<210> SEQ ID NO 49
<211> LENGTH: 6
<212> TYPE: PRT
<213> ORGANISM: Artificial
<220> FEATURE:
<223> OTHER INFORMATION: hydrophilic motif

<400> SEQUENCE: 49

Asp Arg Asp Asp Pro Pro
1               5

<210> SEQ ID NO 50
<211> LENGTH: 6
<212> TYPE: PRT
<213> ORGANISM: Artificial
<220> FEATURE:
<223> OTHER INFORMATION: hydrophilic motif

<400> SEQUENCE: 50

Asp Lys Glu Asp Pro Pro
1               5

<210> SEQ ID NO 51
<211> LENGTH: 6
<212> TYPE: PRT
<213> ORGANISM: Artificial
<220> FEATURE:
<223> OTHER INFORMATION: hydrophilic motif

<400> SEQUENCE: 51

Asp Lys Asp Glu Pro Pro
1               5

<210> SEQ ID NO 52
<211> LENGTH: 6
<212> TYPE: PRT
<213> ORGANISM: Artificial
<220> FEATURE:
<223> OTHER INFORMATION: hydrophilic motif

<400> SEQUENCE: 52

Glu Arg Asp Asp Pro Pro
1               5

<210> SEQ ID NO 53
<211> LENGTH: 6
<212> TYPE: PRT
<213> ORGANISM: Artificial
<220> FEATURE:
<223> OTHER INFORMATION: hydrophilic motif

```
<400> SEQUENCE: 53

Glu Lys Glu Asp Pro Pro
1               5

<210> SEQ ID NO 54
<211> LENGTH: 6
<212> TYPE: PRT
<213> ORGANISM: Artificial
<220> FEATURE:
<223> OTHER INFORMATION: hydrophilic motif

<400> SEQUENCE: 54

Glu Lys Asp Glu Pro Pro
1               5

<210> SEQ ID NO 55
<211> LENGTH: 6
<212> TYPE: PRT
<213> ORGANISM: Artificial
<220> FEATURE:
<223> OTHER INFORMATION: hydrophilic motif

<400> SEQUENCE: 55

Asp Arg Glu Asp Pro Pro
1               5

<210> SEQ ID NO 56
<211> LENGTH: 6
<212> TYPE: PRT
<213> ORGANISM: Artificial
<220> FEATURE:
<223> OTHER INFORMATION: hydrophilic motif

<400> SEQUENCE: 56

Asp Arg Asp Glu Pro Pro
1               5

<210> SEQ ID NO 57
<211> LENGTH: 6
<212> TYPE: PRT
<213> ORGANISM: Artificial
<220> FEATURE:
<223> OTHER INFORMATION: hydrophilic motif

<400> SEQUENCE: 57

Asp Lys Glu Glu Pro Pro
1               5

<210> SEQ ID NO 58
<211> LENGTH: 6
<212> TYPE: PRT
<213> ORGANISM: Artificial
<220> FEATURE:
<223> OTHER INFORMATION: hydrophilic motif

<400> SEQUENCE: 58

Glu Arg Glu Asp Pro Pro
1               5

<210> SEQ ID NO 59
<211> LENGTH: 6
<212> TYPE: PRT
<213> ORGANISM: Artificial
<220> FEATURE:
<223> OTHER INFORMATION: hydrophilic motif

<400> SEQUENCE: 59
```

```
Glu Arg Asp Glu Pro Pro
1               5

<210> SEQ ID NO 60
<211> LENGTH: 6
<212> TYPE: PRT
<213> ORGANISM: Artificial
<220> FEATURE:
<223> OTHER INFORMATION: hydrophilic motif

<400> SEQUENCE: 60

Asp Arg Glu Glu Pro Pro
1               5

<210> SEQ ID NO 61
<211> LENGTH: 6
<212> TYPE: PRT
<213> ORGANISM: Artificial
<220> FEATURE:
<223> OTHER INFORMATION: hydrophilic motif

<400> SEQUENCE: 61

Glu Lys Glu Glu Pro Pro
1               5

<210> SEQ ID NO 62
<211> LENGTH: 6
<212> TYPE: PRT
<213> ORGANISM: Artificial
<220> FEATURE:
<223> OTHER INFORMATION: hydrophilic motif

<400> SEQUENCE: 62

Glu Arg Glu Glu Pro Pro
1               5

<210> SEQ ID NO 63
<211> LENGTH: 10
<212> TYPE: PRT
<213> ORGANISM: Artificial
<220> FEATURE:
<223> OTHER INFORMATION: HIV Tat peptide

<400> SEQUENCE: 63

Gly Arg Lys Lys Arg Arg Gln Arg Arg Arg
1               5                   10

<210> SEQ ID NO 64
<211> LENGTH: 16
<212> TYPE: PRT
<213> ORGANISM: Artificial
<220> FEATURE:
<223> OTHER INFORMATION: penetratin peptide

<400> SEQUENCE: 64

Arg Gln Ile Lys Ile Trp Phe Gln Asn Arg Arg Met Lys Trp Lys Lys
1               5                   10                  15

<210> SEQ ID NO 65
<211> LENGTH: 17
<212> TYPE: PRT
<213> ORGANISM: Artificial
<220> FEATURE:
<223> OTHER INFORMATION: penetratin peptide

<400> SEQUENCE: 65
```

```
Lys Lys Trp Lys Met Arg Arg Asn Gln Phe Trp Val Lys Val Gln Arg
1               5                   10                  15

Gly

<210> SEQ ID NO 66
<211> LENGTH: 27
<212> TYPE: PRT
<213> ORGANISM: Artificial
<220> FEATURE:
<223> OTHER INFORMATION: transportan peptide

<400> SEQUENCE: 66

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 67
<211> LENGTH: 27
<212> TYPE: PRT
<213> ORGANISM: Artificial
<220> FEATURE:
<223> OTHER INFORMATION: MPG/Pep family member peptide

<400> SEQUENCE: 67

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 68
<211> LENGTH: 21
<212> TYPE: PRT
<213> ORGANISM: Artificial
<220> FEATURE:
<223> OTHER INFORMATION: MPG/Pep family member peptide

<400> SEQUENCE: 68

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 69
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 69

Val Val Leu Ile Ala Ala Leu Thr Val Ala
1               5                   10

<210> SEQ ID NO 70
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 70

Val Val Leu Met Ala Ala Leu Thr Val Ala
```

<210> SEQ ID NO 71
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 71

Val Val Leu Val Gly Ala Leu Thr Val Ala
1               5                   10

<210> SEQ ID NO 72
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 72

Val Val Leu Val Ser Ala Leu Thr Val Ala
1               5                   10

<210> SEQ ID NO 73
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 73

Val Val Leu Val Ala Val Leu Thr Val Ala
1               5                   10

<210> SEQ ID NO 74
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 74

Val Val Leu Val Ala Ala Leu Ala Val Ala
1               5                   10

<210> SEQ ID NO 75
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 75

Val Val Leu Val Ala Ala Leu Thr Ala Ala
1               5                   10

<210> SEQ ID NO 76
<211> LENGTH: 10
<212> TYPE: PRT
<213> ORGANISM: Artificial
<220> FEATURE:
<223> OTHER INFORMATION: peptide variant based on amino acids 76 to 85 of human S100A1

<400> SEQUENCE: 76

Val Val Leu Val Ala Ala Leu Thr Ile Ala
1               5                   10

<210> SEQ ID NO 77
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 77

Val Val Leu Val Ala Ala Leu Thr Val Met
1               5                   10

<210> SEQ ID NO 78
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 78

Val Val Leu Val Ala Ala Leu Thr Val Val
1               5                   10

<210> SEQ ID NO 79
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 79

Ile Ile Leu Val Ala Ala Leu Thr Val Ala
1               5                   10

<210> SEQ ID NO 80
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 80

Ile Val Met Val Ala Ala Leu Thr Val Ala
1               5                   10

<210> SEQ ID NO 81
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 81

Ile Val Leu Ile Ala Ala Leu Thr Val Ala
1               5                   10

<210> SEQ ID NO 82

```
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 82

Ile Val Leu Met Ala Ala Leu Thr Val Ala
1               5                   10

<210> SEQ ID NO 83
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 83

Ile Val Leu Val Gly Ala Leu Thr Val Ala
1               5                   10

<210> SEQ ID NO 84
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 84

Ile Val Leu Val Ser Ala Leu Thr Val Ala
1               5                   10

<210> SEQ ID NO 85
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 85

Ile Val Leu Val Ala Val Leu Thr Val Ala
1               5                   10

<210> SEQ ID NO 86
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 86

Ile Val Leu Val Ala Ala Leu Ala Val Ala
1               5                   10

<210> SEQ ID NO 87
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 87
```

```
Ile Val Leu Val Ala Ala Leu Thr Ala Ala
1               5                   10

<210> SEQ ID NO 88
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 88

Ile Val Leu Val Ala Ala Leu Thr Ile Ala
1               5                   10

<210> SEQ ID NO 89
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 89

Ile Val Leu Val Ala Ala Leu Thr Val Met
1               5                   10

<210> SEQ ID NO 90
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 90

Ile Val Leu Val Ala Ala Leu Thr Val Val
1               5                   10

<210> SEQ ID NO 91
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 91

Val Ile Met Val Ala Ala Leu Thr Val Ala
1               5                   10

<210> SEQ ID NO 92
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 92

Val Ile Leu Ile Ala Ala Leu Thr Val Ala
1               5                   10

<210> SEQ ID NO 93
<211> LENGTH: 10
<212> TYPE: PRT
<213> ORGANISM: Artificial
<220> FEATURE:
```

```
<223> OTHER INFORMATION: peptide variant based on amino acids 76 to 85
      of human S100A1

<400> SEQUENCE: 93

Val Ile Leu Met Ala Ala Leu Thr Val Ala
1               5                   10

<210> SEQ ID NO 94
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 94

Val Ile Leu Val Gly Ala Leu Thr Val Ala
1               5                   10

<210> SEQ ID NO 95
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 95

Val Ile Leu Val Ser Ala Leu Thr Val Ala
1               5                   10

<210> SEQ ID NO 96
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 96

Val Ile Leu Val Ala Val Leu Thr Val Ala
1               5                   10

<210> SEQ ID NO 97
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 97

Val Ile Leu Val Ala Ala Leu Ala Val Ala
1               5                   10

<210> SEQ ID NO 98
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 98

Val Ile Leu Val Ala Ala Leu Thr Ala Ala
1               5                   10
```

```
<210> SEQ ID NO 99
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 99

Val Ile Leu Val Ala Ala Leu Thr Ile Ala
1               5                   10

<210> SEQ ID NO 100
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 100

Val Ile Leu Val Ala Ala Leu Thr Val Met
1               5                   10

<210> SEQ ID NO 101
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 101

Val Ile Leu Val Ala Ala Leu Thr Val Val
1               5                   10

<210> SEQ ID NO 102
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 102

Val Val Met Ile Ala Ala Leu Thr Val Ala
1               5                   10

<210> SEQ ID NO 103
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 103

Val Val Met Met Ala Ala Leu Thr Val Ala
1               5                   10

<210> SEQ ID NO 104
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 104
```

Val Val Met Val Gly Ala Leu Thr Val Ala
1               5                   10

<210> SEQ ID NO 105
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 105

Val Val Met Val Ser Ala Leu Thr Val Ala
1               5                   10

<210> SEQ ID NO 106
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 106

Val Val Met Val Ala Val Leu Thr Val Ala
1               5                   10

<210> SEQ ID NO 107
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 107

Val Val Met Val Ala Ala Leu Ala Val Ala
1               5                   10

<210> SEQ ID NO 108
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 108

Val Val Met Val Ala Ala Leu Thr Ala Ala
1               5                   10

<210> SEQ ID NO 109
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 109

Val Val Met Val Ala Ala Leu Thr Ile Ala
1               5                   10

<210> SEQ ID NO 110
<211> LENGTH: 10
<212> TYPE: PRT
<213> ORGANISM: Artificial

```
<220> FEATURE:
<223> OTHER INFORMATION: peptide variant based on amino acids 76 to 85
      of human S100A1

<400> SEQUENCE: 110

Val Val Met Val Ala Ala Leu Thr Val Met
1               5                   10

<210> SEQ ID NO 111
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 111

Val Val Leu Ile Gly Ala Leu Thr Val Ala
1               5                   10

<210> SEQ ID NO 112
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 112

Val Val Leu Ile Ser Ala Leu Thr Val Ala
1               5                   10

<210> SEQ ID NO 113
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 113

Val Val Leu Ile Ala Val Leu Thr Val Ala
1               5                   10

<210> SEQ ID NO 114
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 114

Val Val Leu Ile Ala Ala Leu Ala Val Ala
1               5                   10

<210> SEQ ID NO 115
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 115

Val Val Leu Ile Ala Ala Leu Thr Ala Ala
1               5                   10
```

<210> SEQ ID NO 116
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 116

Val Val Leu Ile Ala Ala Leu Thr Ile Ala
1               5                   10

<210> SEQ ID NO 117
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 117

Val Val Leu Ile Ala Ala Leu Thr Val Met
1               5                   10

<210> SEQ ID NO 118
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 118

Val Val Leu Ile Ala Ala Leu Thr Val Val
1               5                   10

<210> SEQ ID NO 119
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 119

Val Val Leu Met Gly Ala Leu Thr Val Ala
1               5                   10

<210> SEQ ID NO 120
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 120

Val Val Leu Met Ser Ala Leu Thr Val Ala
1               5                   10

<210> SEQ ID NO 121
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

```
<400> SEQUENCE: 121

Val Val Leu Met Ala Val Leu Thr Val Ala
1               5                   10

<210> SEQ ID NO 122
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 122

Val Val Leu Met Ala Ala Leu Ala Val Ala
1               5                   10

<210> SEQ ID NO 123
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 123

Val Val Leu Met Ala Ala Leu Thr Ala Ala
1               5                   10

<210> SEQ ID NO 124
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 124

Val Val Leu Met Ala Ala Leu Thr Ile Ala
1               5                   10

<210> SEQ ID NO 125
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 125

Val Val Leu Met Ala Ala Leu Thr Val Met
1               5                   10

<210> SEQ ID NO 126
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 126

Val Val Leu Met Ala Ala Leu Thr Val Val
1               5                   10

<210> SEQ ID NO 127
<211> LENGTH: 10
<212> TYPE: PRT
```

<213> ORGANISM: Artificial
<220> FEATURE:
<223> OTHER INFORMATION: peptide variant based on amino acids 76 to 85
      of human S100A1

<400> SEQUENCE: 127

Val Val Leu Val Gly Val Leu Thr Val Ala
1               5                   10

<210> SEQ ID NO 128
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 128

Val Val Leu Val Gly Ala Leu Ala Val Ala
1               5                   10

<210> SEQ ID NO 129
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 129

Val Val Leu Val Gly Ala Leu Thr Ala Ala
1               5                   10

<210> SEQ ID NO 130
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 130

Val Val Leu Val Gly Ala Leu Thr Ile Ala
1               5                   10

<210> SEQ ID NO 131
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 131

Val Val Leu Val Gly Ala Leu Thr Val Met
1               5                   10

<210> SEQ ID NO 132
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 132

Val Val Leu Val Gly Ala Leu Thr Val Val
1               5                   10

```
<210> SEQ ID NO 133
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 133

Val Val Leu Val Ser Val Leu Thr Val Ala
1               5                   10

<210> SEQ ID NO 134
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 134

Val Val Leu Val Ser Ala Leu Ala Val Ala
1               5                   10

<210> SEQ ID NO 135
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 135

Val Val Leu Val Ser Ala Leu Thr Ala Ala
1               5                   10

<210> SEQ ID NO 136
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 136

Val Val Leu Val Ser Ala Leu Thr Ile Ala
1               5                   10

<210> SEQ ID NO 137
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 137

Val Val Leu Val Ser Ala Leu Thr Val Met
1               5                   10

<210> SEQ ID NO 138
<211> LENGTH: 10
<212> TYPE: PRT
<213> ORGANISM: Artificial
<220> FEATURE:
<223> OTHER INFORMATION: peptide variant based on amino acids 76 to 85
      of human S100A1
```

<400> SEQUENCE: 138

Val Val Leu Val Ser Ala Leu Thr Val Val
1               5                   10

<210> SEQ ID NO 139
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 139

Val Val Leu Val Ala Val Leu Ala Val Ala
1               5                   10

<210> SEQ ID NO 140
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 140

Val Val Leu Val Ala Val Leu Thr Ala Ala
1               5                   10

<210> SEQ ID NO 141
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 141

Val Val Leu Val Ala Val Leu Thr Ile Ala
1               5                   10

<210> SEQ ID NO 142
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 142

Val Val Leu Val Ala Val Leu Thr Val Met
1               5                   10

<210> SEQ ID NO 143
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 143

Val Val Leu Val Ala Val Leu Thr Val Val
1               5                   10

<210> SEQ ID NO 144
<211> LENGTH: 10

```
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 144

Val Val Leu Val Ala Ala Leu Ala Ala Ala
1               5                   10

<210> SEQ ID NO 145
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 145

Val Val Leu Val Ala Ala Leu Ala Ile Ala
1               5                   10

<210> SEQ ID NO 146
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 146

Val Val Leu Val Ala Ala Leu Ala Val Met
1               5                   10

<210> SEQ ID NO 147
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 147

Val Val Leu Val Ala Ala Leu Ala Val Val
1               5                   10

<210> SEQ ID NO 148
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 148

Val Val Leu Val Ala Ala Leu Thr Ala Met
1               5                   10

<210> SEQ ID NO 149
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 149

Val Val Leu Val Ala Ala Leu Thr Ala Val
```

<210> SEQ ID NO 150
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 150

Val Val Leu Val Ala Ala Leu Thr Ile Met
1               5                   10

<210> SEQ ID NO 151
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 151

Val Val Leu Val Ala Ala Leu Thr Ile Val
1               5                   10

<210> SEQ ID NO 152
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 152

Ile Ile Met Val Ala Ala Leu Thr Val Ala
1               5                   10

<210> SEQ ID NO 153
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 153

Ile Ile Leu Ile Ala Ala Leu Thr Val Ala
1               5                   10

<210> SEQ ID NO 154
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 154

Ile Ile Leu Met Ala Ala Leu Thr Val Ala
1               5                   10

<210> SEQ ID NO 155
<211> LENGTH: 10
<212> TYPE: PRT
<213> ORGANISM: Artificial
<220> FEATURE:
<223> OTHER INFORMATION: peptide variant based on amino acids 76 to 85 of human S100A1

<400> SEQUENCE: 155

Ile Ile Leu Val Ser Ala Leu Thr Val Ala
1               5                   10

<210> SEQ ID NO 156
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 156

Ile Ile Leu Val Ala Val Leu Thr Val Ala
1               5                   10

<210> SEQ ID NO 157
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 157

Ile Ile Leu Val Ala Ala Leu Ala Val Ala
1               5                   10

<210> SEQ ID NO 158
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 158

Ile Ile Leu Val Ala Ala Leu Thr Ala Ala
1               5                   10

<210> SEQ ID NO 159
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 159

Ile Ile Leu Val Ala Ala Leu Thr Ile Ala
1               5                   10

<210> SEQ ID NO 160
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 160

Ile Ile Leu Val Ala Ala Leu Thr Val Met
1               5                   10

<210> SEQ ID NO 161

```
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 161

Ile Ile Leu Val Ala Ala Leu Thr Val Val
1               5                   10

<210> SEQ ID NO 162
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 162

Ile Val Met Ile Ala Ala Leu Thr Val Ala
1               5                   10

<210> SEQ ID NO 163
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 163

Ile Val Met Met Ala Ala Leu Thr Val Ala
1               5                   10

<210> SEQ ID NO 164
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 164

Ile Val Met Val Gly Ala Leu Thr Val Ala
1               5                   10

<210> SEQ ID NO 165
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 165

Ile Val Met Val Ser Ala Leu Thr Val Ala
1               5                   10

<210> SEQ ID NO 166
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 166
```

```
Ile Val Met Val Ala Val Leu Thr Val Ala
1               5                   10

<210> SEQ ID NO 167
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 167

Ile Val Met Val Ala Ala Leu Ala Val Ala
1               5                   10

<210> SEQ ID NO 168
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 168

Ile Val Met Val Ala Ala Leu Thr Ala Ala
1               5                   10

<210> SEQ ID NO 169
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 169

Ile Val Met Val Ala Ala Leu Thr Ile Ala
1               5                   10

<210> SEQ ID NO 170
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 170

Ile Val Met Val Ala Ala Leu Thr Val Met
1               5                   10

<210> SEQ ID NO 171
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 171

Ile Val Met Val Ala Ala Leu Thr Val Val
1               5                   10

<210> SEQ ID NO 172
<211> LENGTH: 10
<212> TYPE: PRT
<213> ORGANISM: Artificial
<220> FEATURE:
```

```
<223> OTHER INFORMATION: peptide variant based on amino acids 76 to 85
      of human S100A1

<400> SEQUENCE: 172

Ile Val Leu Ile Gly Ala Leu Thr Val Ala
1               5                   10

<210> SEQ ID NO 173
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 173

Ile Val Leu Ile Ser Ala Leu Thr Val Ala
1               5                   10

<210> SEQ ID NO 174
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 174

Ile Val Leu Ile Ala Val Leu Thr Val Ala
1               5                   10

<210> SEQ ID NO 175
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 175

Ile Val Leu Ile Ala Ala Leu Ala Val Ala
1               5                   10

<210> SEQ ID NO 176
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 176

Ile Val Leu Ile Ala Ala Leu Thr Ala Ala
1               5                   10

<210> SEQ ID NO 177
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 177

Ile Val Leu Ile Ala Ala Leu Thr Ile Ala
1               5                   10
```

```
<210> SEQ ID NO 178
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 178

Ile Val Leu Ile Ala Ala Leu Thr Val Met
1               5                   10

<210> SEQ ID NO 179
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 179

Ile Val Leu Ile Ala Ala Leu Thr Val Val
1               5                   10

<210> SEQ ID NO 180
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 180

Ile Val Leu Met Gly Ala Leu Thr Val Ala
1               5                   10

<210> SEQ ID NO 181
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 181

Ile Val Leu Met Ser Ala Leu Thr Val Ala
1               5                   10

<210> SEQ ID NO 182
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 182

Ile Val Leu Met Ala Val Leu Thr Val Ala
1               5                   10

<210> SEQ ID NO 183
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 183
```

Ile Val Leu Met Ala Ala Leu Ala Val Ala
1               5                   10

<210> SEQ ID NO 184
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 184

Ile Val Leu Met Ala Ala Leu Thr Ala Ala
1               5                   10

<210> SEQ ID NO 185
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 185

Ile Val Leu Met Ala Ala Leu Thr Ile Ala
1               5                   10

<210> SEQ ID NO 186
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 186

Ile Val Leu Met Ala Ala Leu Thr Val Met
1               5                   10

<210> SEQ ID NO 187
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 187

Ile Val Leu Met Ala Ala Leu Thr Val Val
1               5                   10

<210> SEQ ID NO 188
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 188

Ile Val Leu Val Gly Val Leu Thr Val Ala
1               5                   10

<210> SEQ ID NO 189
<211> LENGTH: 10
<212> TYPE: PRT
<213> ORGANISM: Artificial

```
<220> FEATURE:
<223> OTHER INFORMATION: peptide variant based on amino acids 76 to 85
      of human S100A1

<400> SEQUENCE: 189

Ile Val Leu Val Gly Ala Leu Ala Val Ala
1               5                   10

<210> SEQ ID NO 190
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 190

Ile Val Leu Val Gly Ala Leu Thr Ala Ala
1               5                   10

<210> SEQ ID NO 191
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 191

Ile Val Leu Val Gly Ala Leu Thr Ile Ala
1               5                   10

<210> SEQ ID NO 192
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 192

Ile Val Leu Val Gly Ala Leu Thr Val Met
1               5                   10

<210> SEQ ID NO 193
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 193

Ile Val Leu Val Gly Ala Leu Thr Val Val
1               5                   10

<210> SEQ ID NO 194
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 194

Ile Val Leu Val Ser Val Leu Thr Val Ala
1               5                   10
```

<210> SEQ ID NO 195
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 195

Ile Val Leu Val Ser Ala Leu Ala Val Ala
1               5                   10

<210> SEQ ID NO 196
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 196

Ile Val Leu Val Ser Ala Leu Thr Ala Ala
1               5                   10

<210> SEQ ID NO 197
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 197

Ile Val Leu Val Ser Ala Leu Thr Ile Ala
1               5                   10

<210> SEQ ID NO 198
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 198

Ile Val Leu Val Ser Ala Leu Thr Val Met
1               5                   10

<210> SEQ ID NO 199
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 199

Ile Val Leu Val Ser Ala Leu Thr Val Val
1               5                   10

<210> SEQ ID NO 200
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

```
<400> SEQUENCE: 200

Ile Val Leu Val Ala Val Leu Ala Val Ala
1               5                   10

<210> SEQ ID NO 201
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 201

Ile Val Leu Val Ala Val Leu Thr Ala Ala
1               5                   10

<210> SEQ ID NO 202
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 202

Ile Val Leu Val Ala Val Leu Thr Ile Ala
1               5                   10

<210> SEQ ID NO 203
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 203

Ile Val Leu Val Ala Val Leu Thr Val Met
1               5                   10

<210> SEQ ID NO 204
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 204

Ile Val Leu Val Ala Val Leu Thr Val Val
1               5                   10

<210> SEQ ID NO 205
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 205

Ile Val Leu Val Ala Ala Leu Ala Ala Ala
1               5                   10

<210> SEQ ID NO 206
<211> LENGTH: 10
<212> TYPE: PRT
```

```
<213> ORGANISM: Artificial
<220> FEATURE:
<223> OTHER INFORMATION: peptide variant based on amino acids 76 to 85
      of human S100A1

<400> SEQUENCE: 206

Ile Val Leu Val Ala Ala Leu Ala Ile Ala
1               5                   10

<210> SEQ ID NO 207
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 207

Ile Val Leu Val Ala Ala Leu Ala Val Met
1               5                   10

<210> SEQ ID NO 208
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 208

Ile Val Leu Val Ala Ala Leu Ala Val Val
1               5                   10

<210> SEQ ID NO 209
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 209

Ile Val Leu Val Ala Ala Leu Thr Ala Met
1               5                   10

<210> SEQ ID NO 210
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 210

Ile Val Leu Val Ala Ala Leu Thr Ala Val
1               5                   10

<210> SEQ ID NO 211
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 211

Ile Val Leu Val Ala Ala Leu Thr Ile Met
1               5                   10
```

<210> SEQ ID NO 212
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 212

Ile Val Leu Val Ala Ala Leu Thr Ile Val
1               5                   10

<210> SEQ ID NO 213
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 213

Val Ile Met Ile Ala Ala Leu Thr Val Ala
1               5                   10

<210> SEQ ID NO 214
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 214

Val Ile Met Met Ala Ala Leu Thr Val Ala
1               5                   10

<210> SEQ ID NO 215
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 215

Val Ile Met Val Gly Ala Leu Thr Val Ala
1               5                   10

<210> SEQ ID NO 216
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 216

Val Ile Met Val Ser Ala Leu Thr Val Ala
1               5                   10

<210> SEQ ID NO 217
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 217

Val Ile Met Val Ala Val Leu Thr Val Ala
1               5                   10

<210> SEQ ID NO 218
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 218

Val Ile Met Val Ala Ala Leu Ala Val Ala
1               5                   10

<210> SEQ ID NO 219
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 219

Val Ile Met Val Ala Ala Leu Thr Ala Ala
1               5                   10

<210> SEQ ID NO 220
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 220

Val Ile Met Val Ala Ala Leu Thr Ile Ala
1               5                   10

<210> SEQ ID NO 221
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 221

Val Ile Met Val Ala Ala Leu Thr Val Met
1               5                   10

<210> SEQ ID NO 222
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 222

Val Ile Met Val Ala Ala Leu Thr Val Val
1               5                   10

<210> SEQ ID NO 223
<211> LENGTH: 10

-continued

```
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 223

Val Ile Leu Ile Gly Ala Leu Thr Val Ala
1               5                   10

<210> SEQ ID NO 224
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 224

Val Ile Leu Ile Ser Ala Leu Thr Val Ala
1               5                   10

<210> SEQ ID NO 225
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 225

Val Ile Leu Ile Ala Val Leu Thr Val Ala
1               5                   10

<210> SEQ ID NO 226
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 226

Val Ile Leu Ile Ala Ala Leu Ala Val Ala
1               5                   10

<210> SEQ ID NO 227
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 227

Val Ile Leu Ile Ala Ala Leu Thr Ala Ala
1               5                   10

<210> SEQ ID NO 228
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 228

Val Ile Leu Ile Ala Ala Leu Thr Ile Ala
```

<210> SEQ ID NO 229
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 229

Val Ile Leu Ile Ala Ala Leu Thr Val Met
1               5                   10

<210> SEQ ID NO 230
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 230

Val Ile Leu Ile Ala Ala Leu Thr Val Val
1               5                   10

<210> SEQ ID NO 231
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 231

Val Ile Leu Met Gly Ala Leu Thr Val Ala
1               5                   10

<210> SEQ ID NO 232
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 232

Val Ile Leu Met Ser Ala Leu Thr Val Ala
1               5                   10

<210> SEQ ID NO 233
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 233

Val Ile Leu Met Ala Val Leu Thr Val Ala
1               5                   10

<210> SEQ ID NO 234
<211> LENGTH: 10
<212> TYPE: PRT
<213> ORGANISM: Artificial
<220> FEATURE:
<223> OTHER INFORMATION: peptide variant based on amino acids 76 to 85 of human S100A1

<400> SEQUENCE: 234

Val Ile Leu Met Ala Ala Leu Ala Val Ala
1               5                   10

<210> SEQ ID NO 235
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 235

Val Ile Leu Met Ala Ala Leu Thr Ala Ala
1               5                   10

<210> SEQ ID NO 236
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 236

Val Ile Leu Met Ala Ala Leu Thr Ile Ala
1               5                   10

<210> SEQ ID NO 237
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 237

Val Ile Leu Met Ala Ala Leu Thr Val Met
1               5                   10

<210> SEQ ID NO 238
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 238

Val Ile Leu Met Ala Ala Leu Thr Val Val
1               5                   10

<210> SEQ ID NO 239
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 239

Val Ile Leu Val Gly Val Leu Thr Val Ala
1               5                   10

<210> SEQ ID NO 240

```
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 240

Val Ile Leu Val Gly Ala Leu Ala Val Ala
1               5                   10

<210> SEQ ID NO 241
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 241

Val Ile Leu Val Gly Ala Leu Thr Ala Ala
1               5                   10

<210> SEQ ID NO 242
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 242

Val Ile Leu Val Gly Ala Leu Thr Ile Ala
1               5                   10

<210> SEQ ID NO 243
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 243

Val Ile Leu Val Gly Ala Leu Thr Val Met
1               5                   10

<210> SEQ ID NO 244
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 244

Val Ile Leu Val Gly Ala Leu Thr Val Val
1               5                   10

<210> SEQ ID NO 245
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 245
```

Val Ile Leu Val Ser Ala Leu Ala Val Ala
1               5                   10

<210> SEQ ID NO 246
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 246

Val Ile Leu Val Ser Ala Leu Thr Ala Ala
1               5                   10

<210> SEQ ID NO 247
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 247

Val Ile Leu Val Ser Ala Leu Thr Ile Ala
1               5                   10

<210> SEQ ID NO 248
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 248

Val Ile Leu Val Ser Ala Leu Thr Val Met
1               5                   10

<210> SEQ ID NO 249
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 249

Val Ile Leu Val Ser Ala Leu Thr Val Val
1               5                   10

<210> SEQ ID NO 250
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 250

Val Ile Leu Val Ala Val Leu Ala Val Ala
1               5                   10

<210> SEQ ID NO 251
<211> LENGTH: 10
<212> TYPE: PRT
<213> ORGANISM: Artificial
<220> FEATURE:

```
<223> OTHER INFORMATION: peptide variant based on amino acids 76 to 85
      of human S100A1

<400> SEQUENCE: 251

Val Ile Leu Val Ala Val Leu Thr Ala Ala
1               5                   10

<210> SEQ ID NO 252
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 252

Val Ile Leu Val Ala Val Leu Thr Ile Ala
1               5                   10

<210> SEQ ID NO 253
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 253

Val Ile Leu Val Ala Val Leu Thr Val Met
1               5                   10

<210> SEQ ID NO 254
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 254

Val Ile Leu Val Ala Val Leu Thr Val Val
1               5                   10

<210> SEQ ID NO 255
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 255

Val Ile Leu Val Ala Ala Leu Ala Ala Ala
1               5                   10

<210> SEQ ID NO 256
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 256

Val Ile Leu Val Ala Ala Leu Ala Ile Ala
1               5                   10
```

```
<210> SEQ ID NO 257
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 257

Val Ile Leu Val Ala Ala Leu Ala Val Met
1               5                   10

<210> SEQ ID NO 258
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 258

Val Ile Leu Val Ala Ala Leu Ala Val Val
1               5                   10

<210> SEQ ID NO 259
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 259

Val Ile Leu Val Ala Ala Leu Thr Ala Met
1               5                   10

<210> SEQ ID NO 260
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 260

Val Ile Leu Val Ala Ala Leu Thr Ala Val
1               5                   10

<210> SEQ ID NO 261
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 261

Val Ile Leu Val Ala Ala Leu Thr Ile Met
1               5                   10

<210> SEQ ID NO 262
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 262
```

Val Ile Leu Val Ala Ala Leu Thr Ile Val
1               5                   10

<210> SEQ ID NO 263
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 263

Val Val Met Ile Gly Ala Leu Thr Val Ala
1               5                   10

<210> SEQ ID NO 264
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 264

Val Val Met Ile Ser Ala Leu Thr Val Ala
1               5                   10

<210> SEQ ID NO 265
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 265

Val Val Met Ile Ala Val Leu Thr Val Ala
1               5                   10

<210> SEQ ID NO 266
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 266

Val Val Met Ile Ala Ala Leu Ala Val Ala
1               5                   10

<210> SEQ ID NO 267
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 267

Val Val Met Ile Ala Ala Leu Thr Ala Ala
1               5                   10

<210> SEQ ID NO 268
<211> LENGTH: 10
<212> TYPE: PRT
<213> ORGANISM: Artificial

```
<220> FEATURE:
<223> OTHER INFORMATION: peptide variant based on amino acids 76 to 85
      of human S100A1

<400> SEQUENCE: 268

Val Val Met Ile Ala Ala Leu Thr Ile Ala
1               5                   10

<210> SEQ ID NO 269
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 269

Val Val Met Ile Ala Ala Leu Thr Val Met
1               5                   10

<210> SEQ ID NO 270
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 270

Val Val Met Ile Ala Ala Leu Thr Val Val
1               5                   10

<210> SEQ ID NO 271
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 271

Val Val Met Met Gly Ala Leu Thr Val Ala
1               5                   10

<210> SEQ ID NO 272
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 272

Val Val Met Met Ser Ala Leu Thr Val Ala
1               5                   10

<210> SEQ ID NO 273
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 273

Val Val Met Met Ala Val Leu Thr Val Ala
1               5                   10
```

<210> SEQ ID NO 274
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 274

Val Val Met Met Ala Ala Leu Ala Val Ala
1               5                   10

<210> SEQ ID NO 275
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 275

Val Val Met Met Ala Ala Leu Thr Ala Ala
1               5                   10

<210> SEQ ID NO 276
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 276

Val Val Met Met Ala Ala Leu Thr Ile Ala
1               5                   10

<210> SEQ ID NO 277
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 277

Val Val Met Met Ala Ala Leu Thr Val Met
1               5                   10

<210> SEQ ID NO 278
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 278

Val Val Met Met Ala Ala Leu Thr Val Val
1               5                   10

<210> SEQ ID NO 279
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 279

Val Val Met Val Gly Val Leu Thr Val Ala
1               5                   10

<210> SEQ ID NO 280
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 280

Val Val Met Val Gly Ala Leu Ala Val Ala
1               5                   10

<210> SEQ ID NO 281
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 281

Val Val Met Val Gly Ala Leu Thr Ala Ala
1               5                   10

<210> SEQ ID NO 282
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 282

Val Val Met Val Gly Ala Leu Thr Ile Ala
1               5                   10

<210> SEQ ID NO 283
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 283

Val Val Met Val Gly Ala Leu Thr Val Met
1               5                   10

<210> SEQ ID NO 284
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 284

Val Val Met Val Gly Ala Leu Thr Val Val
1               5                   10

<210> SEQ ID NO 285
<211> LENGTH: 10
<212> TYPE: PRT

```
<213> ORGANISM: Artificial
<220> FEATURE:
<223> OTHER INFORMATION: peptide variant based on amino acids 76 to 85
      of human S100A1

<400> SEQUENCE: 285

Val Val Met Val Ser Val Leu Thr Val Ala
1               5                   10

<210> SEQ ID NO 286
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 286

Val Val Met Val Ser Ala Leu Ala Val Ala
1               5                   10

<210> SEQ ID NO 287
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 287

Val Val Met Val Ser Ala Leu Thr Ala Ala
1               5                   10

<210> SEQ ID NO 288
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 288

Val Val Met Val Ser Ala Leu Thr Ile Ala
1               5                   10

<210> SEQ ID NO 289
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 289

Val Val Met Val Ser Ala Leu Thr Val Met
1               5                   10

<210> SEQ ID NO 290
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 290

Val Val Met Val Ser Ala Leu Thr Val Val
1               5                   10
```

```
<210> SEQ ID NO 291
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 291

Val Val Met Val Ala Val Leu Ala Val Ala
1               5                   10

<210> SEQ ID NO 292
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 292

Val Val Met Val Ala Val Leu Thr Ala Ala
1               5                   10

<210> SEQ ID NO 293
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 293

Val Val Met Val Ala Val Leu Thr Ile Ala
1               5                   10

<210> SEQ ID NO 294
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 294

Val Val Met Val Ala Val Leu Thr Val Met
1               5                   10

<210> SEQ ID NO 295
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 295

Val Val Met Val Ala Val Leu Thr Val Val
1               5                   10

<210> SEQ ID NO 296
<211> LENGTH: 10
<212> TYPE: PRT
<213> ORGANISM: Artificial
<220> FEATURE:
<223> OTHER INFORMATION: peptide variant based on amino acids 76 to 85
      of human S100A1
```

```
<400> SEQUENCE: 296

Val Val Met Val Ala Ala Leu Ala Ala Ala
1               5                   10

<210> SEQ ID NO 297
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 297

Val Val Met Val Ala Ala Leu Ala Ile Ala
1               5                   10

<210> SEQ ID NO 298
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 298

Val Val Met Val Ala Ala Leu Ala Val Met
1               5                   10

<210> SEQ ID NO 299
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 299

Val Val Met Val Ala Ala Leu Ala Val Val
1               5                   10

<210> SEQ ID NO 300
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 300

Val Val Met Val Ala Ala Leu Thr Ala Met
1               5                   10

<210> SEQ ID NO 301
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 301

Val Val Met Val Ala Ala Leu Thr Ala Val
1               5                   10

<210> SEQ ID NO 302
<211> LENGTH: 10
```

```
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 302

Val Val Met Val Ala Ala Leu Thr Ile Met
1               5                   10

<210> SEQ ID NO 303
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 303

Val Val Met Val Ala Ala Leu Thr Ile Val
1               5                   10

<210> SEQ ID NO 304
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 304

Val Val Leu Ile Gly Val Leu Thr Val Ala
1               5                   10

<210> SEQ ID NO 305
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 305

Val Val Leu Ile Gly Ala Leu Ala Val Ala
1               5                   10

<210> SEQ ID NO 306
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 306

Val Val Leu Ile Gly Ala Leu Thr Ala Ala
1               5                   10

<210> SEQ ID NO 307
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 307

Val Val Leu Ile Gly Ala Leu Thr Ile Ala
```

```
1               5                   10

<210> SEQ ID NO 308
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 308

Val Val Leu Ile Gly Ala Leu Thr Val Met
1               5                   10

<210> SEQ ID NO 309
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 309

Val Val Leu Ile Gly Ala Leu Thr Val Val
1               5                   10

<210> SEQ ID NO 310
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 310

Val Val Leu Ile Ser Val Leu Thr Val Ala
1               5                   10

<210> SEQ ID NO 311
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 311

Val Val Leu Ile Ser Ala Leu Ala Val Ala
1               5                   10

<210> SEQ ID NO 312
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 312

Val Val Leu Ile Ser Ala Leu Thr Ala Ala
1               5                   10

<210> SEQ ID NO 313
<211> LENGTH: 10
<212> TYPE: PRT
<213> ORGANISM: Artificial
<220> FEATURE:
<223> OTHER INFORMATION: peptide variant based on amino acids 76 to 85
```

-continued of human S100A1

<400> SEQUENCE: 313

Val Val Leu Ile Ser Ala Leu Thr Ile Ala
1               5                   10

<210> SEQ ID NO 314
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 314

Val Val Leu Ile Ser Ala Leu Thr Val Met
1               5                   10

<210> SEQ ID NO 315
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 315

Val Val Leu Ile Ser Ala Leu Thr Val Val
1               5                   10

<210> SEQ ID NO 316
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 316

Val Val Leu Ile Ala Val Leu Ala Val Ala
1               5                   10

<210> SEQ ID NO 317
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 317

Val Val Leu Ile Ala Val Leu Thr Ala Ala
1               5                   10

<210> SEQ ID NO 318
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 318

Val Val Leu Ile Ala Val Leu Thr Ile Ala
1               5                   10

<210> SEQ ID NO 319

```
<210> SEQ ID NO 319
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 319

Val Val Leu Ile Ala Val Leu Thr Val Met
1               5                   10

<210> SEQ ID NO 320
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 320

Val Val Leu Ile Ala Val Leu Thr Val Val
1               5                   10

<210> SEQ ID NO 321
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 321

Val Val Leu Ile Ala Ala Leu Ala Ile Ala
1               5                   10

<210> SEQ ID NO 322
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 322

Val Val Leu Ile Ala Ala Leu Ala Val Met
1               5                   10

<210> SEQ ID NO 323
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 323

Val Val Leu Ile Ala Ala Leu Ala Val Val
1               5                   10

<210> SEQ ID NO 324
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 324
```

Val Val Leu Ile Ala Ala Leu Thr Ala Met
1               5                   10

<210> SEQ ID NO 325
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 325

Val Val Leu Ile Ala Ala Leu Thr Ala Val
1               5                   10

<210> SEQ ID NO 326
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 326

Val Val Leu Ile Ala Ala Leu Thr Ile Met
1               5                   10

<210> SEQ ID NO 327
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 327

Val Val Leu Ile Ala Ala Leu Thr Ile Val
1               5                   10

<210> SEQ ID NO 328
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 328

Val Val Leu Met Gly Val Leu Thr Val Ala
1               5                   10

<210> SEQ ID NO 329
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 329

Val Val Leu Met Gly Ala Leu Ala Val Ala
1               5                   10

<210> SEQ ID NO 330
<211> LENGTH: 10
<212> TYPE: PRT
<213> ORGANISM: Artificial
<220> FEATURE:

```
<223> OTHER INFORMATION: peptide variant based on amino acids 76 to 85
      of human S100A1

<400> SEQUENCE: 330

Val Val Leu Met Gly Ala Leu Thr Ala Ala
1               5                   10

<210> SEQ ID NO 331
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 331

Val Val Leu Met Gly Ala Leu Thr Ile Ala
1               5                   10

<210> SEQ ID NO 332
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 332

Val Val Leu Met Gly Ala Leu Thr Val Met
1               5                   10

<210> SEQ ID NO 333
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 333

Val Val Leu Met Gly Ala Leu Thr Val Val
1               5                   10

<210> SEQ ID NO 334
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 334

Val Val Leu Met Ser Val Leu Thr Val Ala
1               5                   10

<210> SEQ ID NO 335
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 335

Val Val Leu Met Ser Ala Leu Ala Val Ala
1               5                   10
```

```
<210> SEQ ID NO 336
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 336

Val Val Leu Met Ser Ala Leu Thr Ala Ala
1               5                   10

<210> SEQ ID NO 337
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 337

Val Val Leu Met Ser Ala Leu Thr Ile Ala
1               5                   10

<210> SEQ ID NO 338
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 338

Val Val Leu Met Ser Ala Leu Thr Val Met
1               5                   10

<210> SEQ ID NO 339
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 339

Val Val Leu Met Ser Ala Leu Thr Val Val
1               5                   10

<210> SEQ ID NO 340
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 340

Val Val Leu Met Ala Val Leu Ala Val Ala
1               5                   10

<210> SEQ ID NO 341
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 341
```

Val Val Leu Met Ala Val Leu Thr Ala Ala
1               5                   10

<210> SEQ ID NO 342
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 342

Val Val Leu Met Ala Val Leu Thr Ile Ala
1               5                   10

<210> SEQ ID NO 343
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 343

Val Val Leu Met Ala Val Leu Thr Val Met
1               5                   10

<210> SEQ ID NO 344
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 344

Val Val Leu Met Ala Val Leu Thr Val Val
1               5                   10

<210> SEQ ID NO 345
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 345

Val Val Leu Met Ala Ala Leu Ala Ala Ala
1               5                   10

<210> SEQ ID NO 346
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 346

Val Val Leu Met Ala Ala Leu Ala Ile Ala
1               5                   10

<210> SEQ ID NO 347
<211> LENGTH: 10
<212> TYPE: PRT
<213> ORGANISM: Artificial

```
<220> FEATURE:
<223> OTHER INFORMATION: peptide variant based on amino acids 76 to 85
      of human S100A1

<400> SEQUENCE: 347

Val Val Leu Met Ala Ala Leu Ala Val Met
1               5                   10

<210> SEQ ID NO 348
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 348

Val Val Leu Met Ala Ala Leu Ala Val Val
1               5                   10

<210> SEQ ID NO 349
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 349

Val Val Leu Val Gly Val Leu Ala Val Ala
1               5                   10

<210> SEQ ID NO 350
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 350

Val Val Leu Val Gly Val Leu Thr Ala Ala
1               5                   10

<210> SEQ ID NO 351
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 351

Val Val Leu Val Gly Val Leu Thr Ile Ala
1               5                   10

<210> SEQ ID NO 352
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 352

Val Val Leu Val Gly Val Leu Thr Val Met
1               5                   10
```

<210> SEQ ID NO 353
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 353

Val Val Leu Val Gly Val Leu Thr Val Val
1               5                   10

<210> SEQ ID NO 354
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 354

Val Val Leu Val Gly Ala Leu Ala Ala Ala
1               5                   10

<210> SEQ ID NO 355
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 355

Val Val Leu Val Gly Ala Leu Ala Ile Ala
1               5                   10

<210> SEQ ID NO 356
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 356

Val Val Leu Val Gly Ala Leu Ala Val Met
1               5                   10

<210> SEQ ID NO 357
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 357

Val Val Leu Val Gly Ala Leu Ala Val Val
1               5                   10

<210> SEQ ID NO 358
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

```
<400> SEQUENCE: 358

Val Val Leu Val Gly Ala Leu Thr Ala Met
1               5                   10

<210> SEQ ID NO 359
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 359

Val Val Leu Val Gly Ala Leu Thr Ala Val
1               5                   10

<210> SEQ ID NO 360
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 360

Val Val Leu Val Gly Ala Leu Thr Ile Met
1               5                   10

<210> SEQ ID NO 361
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 361

Val Val Leu Val Gly Ala Leu Thr Ile Val
1               5                   10

<210> SEQ ID NO 362
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 362

Val Val Leu Val Ser Val Leu Ala Val Ala
1               5                   10

<210> SEQ ID NO 363
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 363

Val Val Leu Val Ser Val Leu Thr Ala Ala
1               5                   10

<210> SEQ ID NO 364
<211> LENGTH: 10
<212> TYPE: PRT
```

```
<213> ORGANISM: Artificial
<220> FEATURE:
<223> OTHER INFORMATION: peptide variant based on amino acids 76 to 85
      of human S100A1

<400> SEQUENCE: 364

Val Val Leu Val Ser Val Leu Thr Ile Ala
1               5                   10

<210> SEQ ID NO 365
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 365

Val Val Leu Val Ser Val Leu Thr Val Met
1               5                   10

<210> SEQ ID NO 366
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 366

Val Val Leu Val Ser Val Leu Thr Val Val
1               5                   10

<210> SEQ ID NO 367
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 367

Val Val Leu Val Ser Ala Leu Ala Ala Ala
1               5                   10

<210> SEQ ID NO 368
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 368

Val Val Leu Val Ser Ala Leu Ala Ile Ala
1               5                   10

<210> SEQ ID NO 369
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 369

Val Val Leu Val Ser Ala Leu Ala Val Met
1               5                   10
```

```
<210> SEQ ID NO 370
<211> LENGTH: 11
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 370

Val Val Leu Val Ser Ala Leu Ala Val Ala Val
1               5                   10

<210> SEQ ID NO 371
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 371

Val Val Leu Val Ser Ala Leu Thr Ala Met
1               5                   10

<210> SEQ ID NO 372
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 372

Val Val Leu Val Ser Ala Leu Thr Ala Val
1               5                   10

<210> SEQ ID NO 373
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 373

Val Val Leu Val Ser Ala Leu Thr Ile Met
1               5                   10

<210> SEQ ID NO 374
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 374

Val Val Leu Val Ser Ala Leu Thr Ile Val
1               5                   10

<210> SEQ ID NO 375
<211> LENGTH: 10
<212> TYPE: PRT
<213> ORGANISM: Artificial
<220> FEATURE:
<223> OTHER INFORMATION: peptide variant based on amino acids 76 to 85
      of human S100A1
```

```
<400> SEQUENCE: 375

Val Val Leu Val Ala Val Leu Ala Ala Ala
1               5                   10

<210> SEQ ID NO 376
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 376

Val Val Leu Val Ala Val Leu Ala Ile Ala
1               5                   10

<210> SEQ ID NO 377
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 377

Val Val Leu Val Ala Val Leu Ala Val Met
1               5                   10

<210> SEQ ID NO 378
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 378

Val Val Leu Val Ala Val Leu Ala Val Val
1               5                   10

<210> SEQ ID NO 379
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 379

Val Val Leu Val Ala Val Leu Thr Ala Met
1               5                   10

<210> SEQ ID NO 380
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 380

Val Val Leu Val Ala Val Leu Thr Ala Val
1               5                   10

<210> SEQ ID NO 381
<211> LENGTH: 10
```

```
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 381

Val Val Leu Val Ala Val Leu Thr Ile Met
1               5                   10

<210> SEQ ID NO 382
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 382

Val Val Leu Val Ala Val Leu Thr Ile Val
1               5                   10

<210> SEQ ID NO 383
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 383

Val Val Leu Val Ala Ala Leu Ala Ala Met
1               5                   10

<210> SEQ ID NO 384
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 384

Val Val Leu Val Ala Ala Leu Ala Ala Val
1               5                   10

<210> SEQ ID NO 385
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 385

Val Val Leu Val Ala Ala Leu Ala Ile Met
1               5                   10

<210> SEQ ID NO 386
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 386

Val Val Leu Val Ala Ala Leu Ala Ile Val
```

```
<210> SEQ ID NO 387
<211> LENGTH: 10
<212> TYPE: PRT
<213> ORGANISM: Artificial
<220> FEATURE:
<223> OTHER INFORMATION: variable peptide based on amino acids 76 to 85
      of human S100A1
<220> FEATURE:
<221> NAME/KEY: VARIANT
<222> LOCATION: (2)..(2)
<223> OTHER INFORMATION: residue 2 may be valine or isoleucine
<220> FEATURE:
<221> NAME/KEY: VARIANT
<222> LOCATION: (4)..(4)
<223> OTHER INFORMATION: residue 4 may be valine or isoleucine
<220> FEATURE:
<221> NAME/KEY: VARIANT
<222> LOCATION: (5)..(5)
<223> OTHER INFORMATION: residue 5 may be alanine or serine
<220> FEATURE:
<221> NAME/KEY: VARIANT
<222> LOCATION: (6)..(6)
<223> OTHER INFORMATION: residue 6 may be alanine or valine
<220> FEATURE:
<221> NAME/KEY: VARIANT
<222> LOCATION: (8)..(8)
<223> OTHER INFORMATION: residue 8 may be threonine or alanine
<220> FEATURE:
<221> NAME/KEY: VARIANT
<222> LOCATION: (9)..(9)
<223> OTHER INFORMATION: residue 9 may be valine or alanine

<400> SEQUENCE: 387

Val Xaa Leu Xaa Xaa Xaa Leu Xaa Xaa Ala
1               5                   10

<210> SEQ ID NO 388
<211> LENGTH: 6
<212> TYPE: PRT
<213> ORGANISM: Artificial
<220> FEATURE:
<223> OTHER INFORMATION: amino acids 75 to 80 of human S100A1

<400> SEQUENCE: 388

Tyr Val Val Leu Val Ala
1               5

<210> SEQ ID NO 389
<211> LENGTH: 6
<212> TYPE: PRT
<213> ORGANISM: Artificial
<220> FEATURE:
<223> OTHER INFORMATION: amino acids 80 to 85 of human S100A1

<400> SEQUENCE: 389

Ala Ala Leu Thr Val Ala
1               5

<210> SEQ ID NO 390
<211> LENGTH: 10
<212> TYPE: PRT
<213> ORGANISM: Artificial
<220> FEATURE:
```

<223> OTHER INFORMATION: peptide variant based on amino acids 76 to 85
      of human S100A1

<400> SEQUENCE: 390

Val Val Leu Met Ala Ala Leu Thr Ala Met
1               5                   10

<210> SEQ ID NO 391
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 391

Val Val Leu Met Ala Ala Leu Thr Ala Val
1               5                   10

<210> SEQ ID NO 392
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 392

Val Val Leu Met Ala Ala Leu Thr Ile Met
1               5                   10

<210> SEQ ID NO 393
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 393

Val Val Leu Met Ala Ala Leu Thr Ile Val
1               5                   10

<210> SEQ ID NO 394
<211> LENGTH: 10
<212> TYPE: PRT
<213> ORGANISM: Artificial
<220> FEATURE:
<223> OTHER INFORMATION: peptide variant based on amino acids 76 to 85
      of human S100A1

<400> SEQUENCE: 394

Ile Val Leu Val Ala Ala Leu Thr Val Ala
1               5                   10

S100 BASED TREATMENT OF CARDIAC POWER FAILURE

CROSS-REFERENCE TO RELATED APPLICATION

This application is a U.S. national phase of International Application No. PCT/EP2014/071024, filed Oct. 1, 2014, which claims priority to European Patent Application No. 13186913.3, filed Oct. 1, 2013, the disclosures of which are hereby incorporated by reference in their entirety.

The present invention relates to S100 protein and nuclei acids encoding S100 protein for enhancing the cardiac power, vectors and pharmaceuticals comprising the same, and uses thereof.

BACKGROUND OF THE INVENTION

Muscle tissue is subdivided into skeletal muscle, cardiac muscle, and smooth muscle tissue and can be considered the biggest organ of a vertebrate. For example, an average adult human male is made up of 40 to 50% skeletal muscle. Skeletal muscle and cardiac muscle belong to the striated muscle tissue and share many functional aspects. For example, the process of excitation-contraction coupling in skeletal muscle cells and cardiac muscle cells (cardiomyocytes) is very similar. Membrane depolarization of the myocytes causes calcium influx via activated voltage-gated L-type calcium channels into the cytoplasm (sarcoplasm) of the myocyte. The rise of the cytoplasmic calcium concentration leads to calcium release from the sarcoplasmic reticulum (SR) by activation of ryanodine receptors (RyR) through the calcium-induced calcium release (CICR) mechanism, and thus, to a further rapid rise of the cytoplasmic calcium concentration. Calcium molecules diffuse through the cytoplasm and bind to the contractile proteins such as troponin C which causes contraction of the myocytes. After contraction, calcium is cleared from the cytoplasm by re-uptake of calcium into the sarcoplasmic reticulum mainly by the action of a sarcoplasmic/endoplasmic reticulum calcium ATPase (SERCA). These events are essentially identical in skeletal muscle cells and cardiac muscle cells with minor differences in the isoforms of the involved proteins. For example, while RyR1 is the predominant sarcoplasmic reticulum calcium release channel in skeletal muscle cells, RyR2 is predominant in cardiomyocyte. Similarly, the skeletal muscle sarcoplasmic/endoplasmic reticulum calcium ATPase is SERCA1a, whereas SERCA2a is cardiomyocyte-specific.

Calcium cycling in myocytes is regulated by a plethora of proteins. For example, S100A1 belonging to the S100 protein family (the largest EF-hand calcium-binding protein subfamily) has been reported to interact with both the RyR calcium release channel and SERCA. S100A1 stabilizes RyR in diastole reducing the frequency of calcium sparks and augments calcium release during systole. Furthermore, S100A1 increases SERCA activity during the relaxation phase and it was found to increase contractile function in cardiac muscle as well as skeletal muscle cells. It has been shown that a carboxy-terminal peptide derived from the S100A1 protein mimics the inotropic effect of the full-length S100A1 protein (Most P. et al., 2007, Am. J. Physiol. Regul. Integr. Comp. Physiol. 293:R568-577; Voelkers M. et al., 2007, Cell Calcium 41:135-143).

Defective calcium cycling in myocytes, for example, reduced calcium release from the sarcoplasmic reticulum during contraction, aberrant calcium release events, calcium leakage from the sarcoplasmic reticulum, or slowed calcium clearance from the cytoplasm, results in a variety of myopathies, i.e., diseases associated with muscular malfunction. For example, cardiac insufficiency, contractile ventricular dysfunction, arrhythmias, heart failure, cardiogenic shock, myocardial infarction, and dysfunction of heart valves have been associated with dysregulation of calcium handling in cardiomyocytes. Analogously, defective calcium cycling in skeletal muscle fibers has been linked with muscular dystrophy (Hopf F. W. et al., 2007, Subcell. Biochem. 45:429-64). Furthermore, mutations in the RyR calcium release channels causing disruption of calcium signaling in muscle cells have been associated with myopathies. In particular, more than 80 mutations have been identified in the skeletal muscle RyR1 calcium release channel and have been linked to malignant hyperthermia, central core disease, or multiminicore disease. Furthermore, more than 40 mutations in the cardiac RyR2 calcium release channel leading to ventricular arrhythmias and sudden cardiac death have been reported (Dulhunty A. F. et al., 2006, J. Muscle Res. Cell Motil. 27:351-365).

At present, there are no clinical inotropic therapies available for skeletal muscle disorders. Approved therapeutics currently available for the inotropic treatment of cardiomyopathies, such as glycoside derivatives, catecholamines, and phosphodiesterase inhibitors, are afflicted with severe side effects such as increased heart rate and life threatening proarrhythmogenic potential. Besides these approved therapeutics, the S100A1 protein has been suggested as therapeutic in cardiomyopathies, since it was shown that myocardial levels of S100A1 are decreased in heart failure and that S100A1 delivery to cardiomyocytes results in an increase of isometric contraction followed by an increase in the amount of calcium pumped into the sarcoplasmic reticulum.

However, so far it was unknown that the amount of S100 protein present in the myocardium has to be within a specific dosage range for it to be therapeutically effective in treating cardiomyopathies.

The present inventors surprisingly found that the S100A1 protein only exhibits its therapeutic effects if it is present in the myocardium in a certain dosage range. It was found that S100 protein present in amounts above or below said range does not result in the same beneficial effect in treating cardiomyopathies. Previously observed therapeutic effects of S100 happened to be within the therapeutic range by chance only as could be shown by the present inventors. Based on small- and large-animal models the present inventors could show that the therapeutic effect of the S100 protein is necessarily based on a specific amount of the S100 protein present within the myocardium which has to be within the specified dosage range. The therapeutic effect of the S100 protein is independent of the specific form of administration or formulation and is also independent of means to constitutively or conditionally manipulate expression levels such as by vector-based cardiac delivery of S100 cDNA or any other chemical, pharmaceutical or physical means to variably regulate or modulate cardiac S100 expression.

SUMMARY OF THE INVENTION

In a first aspect, the present invention relates to a S100 protein or a nucleic acid encoding said S100 protein for use in treating a cardiac disease by enhancing the cardiac power in an individual suffering from or at risk of developing said cardiac disease, wherein the concentration of the S100 protein in the myocardium of said individual is increased to no more than the 50 fold concentration in a healthy individual.

In a second aspect, the present invention relates to a S100 protein or a nucleic acid encoding said S100 protein for use in treating a cardiac disease by enhancing the cardiac power in an individual suffering from or at risk of developing said cardiac disease, wherein the concentration in the myocardium of said individual is increased to 0.5-42 µg per g of wet weight myocardium.

In a third aspect, the present invention relates to a pharmaceutical composition comprising at least one S100 protein or nucleic acid according to the first or second aspect and optionally a pharmaceutically acceptable excipient, carrier, and/or diluent.

In a fourth aspect, the present invention relates to Adeno-associated virus 6 or 9 comprising a nucleic acid encoding a S100 protein for use in treating a cardiac disease by enhancing cardiac power in a subject, which is administered to an individual.

In a fifth aspect, the present invention relates to the use of the S100 protein or a nucleic acid encoding said S100 protein for increasing the concentration of said S100 protein in the myocardium of an individual suffering from or at risk of developing a cardiac disorder, to be within the therapeutic window.

In a sixth aspect, the present invention relates to a method of increasing the concentration of the S100 protein in the myocardium of an individual suffering from or at risk of developing a cardiac disorder to be within the therapeutic window by administering a vector, comprising a nucleic acid encoding said S100 protein or an inotropic peptide thereof.

In a seventh aspect, the present invention relates to a method of treating an individual suffering from or at risk of developing a cardiac disorder by increasing the concentration of the S100 protein in the myocardium of said individual to be within the therapeutic window.

LIST OF FIGURES

FIG. 1: Left ventricular ejection fraction (LV EF %) in mice assessed by WB and ELISA. n=15 animals per group; data given as mean±SEM; *$P<0.05$ vs. normal; 2 way ANOVA FIG. 2: S100A1 re-expression and over-expression in failing mouse hearts assessed by LV EF %. Values reflect the relative range from re-expression to normal and up to 50 fold relative increase in S100A1 protein levels. n=12 animals per group; data given as mean±SEM; *$P<0.05$ vs. failing; 2 way ANOVA FIG. 3: S100A1 re-expression and over-expression in failing mouse hearts assessed left ventricular catheterization with maximal LV pressure rise increase (LV+dp/dt max) Values reflect the relative range from re-expression to normal and up to 50 fold relative increase in S100A1 protein levels. n=12 animals per group; data given as mean±SEM; *$P<0.05$ vs. failing; 2 way ANOVA FIG. 4: S100A1 re-expression and over-expression in failing mouse hearts prevents β-adrenergically triggered ventricular tachyarrhythmias including re-expression to normal and up to a 50 fold increase in S100A1 protein levels. Values reflect the relative range from re-expression to normal and up to 50 fold relative increase in myocardial S100A1 protein levels. n=12 animals per group; data given as mean±SEM; *$P<0.05$ vs. failing; 2 way ANOVA FIG. 5: S100A1 re-expression and over-expression in failing mouse hearts improves the CrP/ATP ratio as surrogate for cardiac metabolism restoration including re-expression to normal and up to a 50 fold increase in S100A1 protein levels. Values reflect the relative range from re-expression to normal and up to 50 fold relative increase in S100A1 protein levels. n=12 animals per group; data given as mean±SEM; *$P<0.05$ vs. failing; 2 way ANOVA FIG. 6: S100A1 re-expression and over-expression in failing pig hearts restores and improves cardiac function assessed by LV EF % as surrogate for invasive hemodynamic including re-expression to normal and up to a 50 fold increase in S100A1 protein levels. Values reflect the relative range from re-expression to normal and up to 50 fold relative increase in S100A1 protein levels. n=10 animals per group; data given as mean±SEM; *$P<0.05$ vs. failing; 2 way ANOVA FIG. 7: S100A1 re-expression and over-expression in failing pig hearts restores and improves cardiac function assessed by left ventricular catheterization with LV+dp/dt max as surrogate for invasive hemodynamic including re-expression to normal and up to a 50 fold increase in S100A1 protein levels. Values reflect the relative range from re-expression to normal and up to 50 fold relative increase in S100A1 protein levels. n=10 animals per group; data given as mean±SEM; *$P<0.05$ vs. failing; 2 way ANOVA FIG. 8: S100A1 re-expression and over-expression in failing mouse hearts prevents β-adrenergically triggered ventricular tachyarrhythmias including re-expression to normal and up to a 50 fold increase in S100A1 protein levels. Values reflect the relative range from re-expression to normal and up to 50 fold relative increase in S100A1 protein levels. n=10 animals per group; data given as mean±SEM; *$P<0.05$ vs. failing; 2 way ANOVA FIG. 9: that S100A1 re-expression and over-expression in failing pig myocardium improves the CrP/ATP as a surrogate for cardiac metabolism restoration including re-expression to normal and up to a 50 fold increase in S100A1 protein levels. Values reflect the relative range from re-expression to normal and up to 50 fold relative increase in S100A1 protein levels. n=10 animals per group; data given as mean±SEM; *$P<0.05$ vs. failing; 2 way ANOVA

DETAILED DESCRIPTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Definitions

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, cell biology, and recombinant DNA techniques are employed which are explained in the literature in the field (cf., e.g., *Molecular Cloning: A Laboratory Manual*, 2$^{nd}$ Edition, J. Sambrook et al. eds., Cold Spring Harbor Laboratory Press, Cold Spring Harbor 1989). Furthermore, conventional methods of clinical cardiology are employed which are also explained in the literature in the field (cf., e.g., *Practical Methods in Cardiovascular Research*, S. Dhein et al. eds., Springer Verlag Berlin Heidelberg, 2005).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise. The term "about" when used in connection with a numerical value is meant to encompass numerical values within a range having a lower limit that is 5% smaller than the indicated numerical value and having an upper limit that is 5% larger than the indicated numerical value.

In the context of the different aspects of present invention, the term "peptide" refers to a short polymer of amino acids linked by peptide bonds. It has the same chemical (peptide) bonds as proteins, but is commonly shorter in length. The shortest peptide is a dipeptide, consisting of two amino acids joined by a single peptide bond. There can also be a tripeptide, tetrapeptide, pentapeptide, etc. Preferably, the peptide has a length of up to 8, 10, 12, 15, 18 or 20 amino acids. A peptide has an amino end and a carboxyl end, unless it is a cyclic peptide.

In the context of the different aspects of present invention, the term "polypeptide" refers to a single linear chain of amino acids bonded together by peptide bonds and preferably comprises at least about 21 amino acids. A polypeptide can be one chain of a protein that is composed of more than one chain or it can be the protein itself if the protein is composed of one chain.

In the context of the different aspects of present invention, the term "protein" refers to a molecule comprising one or more polypeptides that resume a secondary and tertiary structure and additionally refers to a protein that is made up of several polypeptides, i.e. several subunits, forming quaternary structures. The protein has sometimes non-peptide groups attached, which can be called prosthetic groups or cofactors.

In the context of present invention, the primary structure of a protein or polypeptide is the sequence of amino acids in the polypeptide chain. The secondary structure in a protein is the general three-dimensional form of local segments of the protein. It does not, however, describe specific atomic positions in three-dimensional space, which are considered to be tertiary structure. In proteins, the secondary structure is defined by patterns of hydrogen bonds between backbone amide and carboxyl groups. The tertiary structure of a protein is the three-dimensional structure of the protein determined by the atomic coordinates. The quaternary structure is the arrangement of multiple folded or coiled protein or polypeptide molecules in a multi-subunit complex. The terms "amino acid chain" and "polypeptide chain" are used synonymously in the context of present invention.

The term "post-translational" used herein refers to events that occur after the translation of a nucleotide triplet into an amino acid and the formation of a peptide bond to the proceeding amino acid in the sequence. Such post-translational events may occur after the entire polypeptide was formed or already during the translation process on those parts of the polypeptide that have already been translated. Post-translational events typically alter or modify the chemical or structural properties of the resultant polypeptide. Examples of post-translational events include but are not limited to events such as glycosylation or phosphorylation of amino acids, or cleavage of the peptide chain, e.g. by an endopeptidase.

The term "co-translational" used herein refers to events that occur during the translation process of a nucleotide triplet into an amino acid chain. Those events typically alter or modify the chemical or structural properties of the resultant amino acid chain. Examples of co-translational events include but are not limited to events that may stop the translation process entirely or interrupted the peptide bond formation resulting in two discreet translation products.

The terms "polynucleotide" and "nucleic acid" are used synonymously and are understood as single or double-stranded oligo- or polymers of deoxyribonucleotide or ribonucleotide bases or both. The depiction of a single strand of a nucleic acid also defines (at least partially) the sequence of the complementary strand. The nucleic acid may be single or double stranded, or may contain portions of both double and single stranded sequences. In the context of the different aspects of present invention, the term nucleic acid comprises cDNA, genomic DNA, recombinant DNA, cRNA and mRNA. A nucleic acid may consist of an entire gene, or a portion thereof, the nucleic acid may also be a microRNA (miRNA) or small interfering RNA (siRNA). The term "oligonucleotide" when used in the context of one of the different aspects of present invention, refers to a nucleic acid of up to about 50 nucleotides, e.g. 2 to about 50 nucleotides in length. "Nucleic acid" molecules are understood as a polymeric or oligomeric macromolecule made from nucleotide monomers. Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. In the context of the present invention referred to nucleic acid molecules include but are not limited to ribonucleic acid (RNA), deoxyribonucleic acid (DNA), and mixtures thereof such as e.g. RNA-DNA hybrids. The nucleic acid may be obtained by biological, biochemical or chemical synthesis methods or any of the methods known in the art. The nucleic acids, can e.g. be synthesized chemically, e.g. in accordance with the phosphotriester method (see, for example, Uhlmann, E. & Peyman, A. (1990) Chemical Reviews, 90, 543-584). "Aptamers" are nucleic acids which bind with high affinity to a polypeptide. Aptamers can be isolated by selection methods from a large pool of different single-stranded RNA molecules (see e.g. Jayasena (1999) Clin. Chem., 45, 1628-50; Klug and Famulok (1994) M. Mol. Biol. Rep., 20, 97-107; U.S. Pat. No. 5,582,981). Aptamers can also be synthesized and selected in their mirror-image form, for example as the L-ribonucleotide (Nolte et al. (1996) Nat. Biotechnol., 14, 1116-9; Klussmann et al. (1996) Nat. Biotechnol., 14, 1112-5). Forms which have been isolated in this way enjoy the advantage that they are not degraded by naturally occurring ribonucleases and, therefore, possess greater stability. Nucleic acids may be degraded by endonucleases or exonucleases, in particular by DNases and RNases which can be found in the cell. It is, therefore, advantageous to modify the nucleic acids in order to stabilize them against degradation, thereby ensuring that a high concentration of the nucleic acid is maintained in the cell over a long period of time (Beigelman et al. (1995) Nucleic Acids Res. 23:3989-94; WO 95/11910; WO 98/37240; WO 97/29116). Typically, such stabilization can be obtained by introducing one or more internucleotide phosphorus groups or by introducing one or more non-phosphorus internucleotides. Suitable modified internucleotides are compiled in Uhlmann and Peyman (1990), supra (see also Beigelman et al. (1995) Nucleic Acids Res. 23:3989-94; WO 95/11910; WO 98/37240; WO 97/29116). Modified internucleotide phosphate radicals and/or non-phosphorus bridges in a nucleic acid which can be employed in one of the uses according to the invention contain, for example, methyl phosphonate, phosphorothioate, phosphoramidate, phosphorodithioate and/or phosphate esters, whereas non-phosphorus internucleotide analogues contain, for example, siloxane bridges, carbonate bridges, carboxymethyl esters, acetamidate bridges and/or thioether bridges. It is also the intention that this modification should improve the durability of a pharmaceutical composition which can be employed in one of the uses according to the invention.

As used herein, the term "vector" refers to a protein or a polynucleotide or a mixture thereof which is capable of being introduced or of introducing the proteins and/or nucleic acid comprised therein into a cell. In the context of the present invention it is preferred that the genes of interest encoded by the introduced polynucleotide are expressed within the cell upon introduction of the vector or vectors. Examples of suitable vectors include but are not limited to plasmids, cosmids, phages, viruses or artificial chromosomes.

The term "open reading frame" (ORF) refers to a sequence of nucleotides, that can be translated into amino acids. Typically, such an ORF contains a start codon, a subsequent region usually having a length which is a multiple of 3 nucleotides, but does not contain a stop codon (TAG, TAA, TGA, UAG, UAA, or UGA) in the given reading frame. Typically, ORFs occur naturally or are constructed artificially, i.e. by gene-technological means. An ORF codes for a protein where the amino acids into which it can be translated form a peptide-linked chain.

As used herein, the term "variant" is to be understood as a polynucleotide or protein which differs in comparison to the polynucleotide or protein from which it is derived by one or more changes in its length or sequence. The polypeptide or polynucleotide from which a protein or nucleic acid variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Typically, a variant is constructed artificially, preferably by gene-technological means whilst the parent polypeptide or polynucleotide is a wild-type protein or polynucleotide. However, also naturally occurring variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, i.e. is functionally active.

As used herein, the term protein or segment "variant" is to be understood as a polypeptide (or segment) which differs in comparison to the polypeptide (or segment, epitop, or domain) from which it is derived by one or more changes in the amino acid sequence. The polypeptide from which a protein variant is derived is also known as the parent polypeptide. Likewise, the segment from which a segment variant is derived from is known as the parent segment. Typically, a variant is constructed artificially, preferably by gene-technological means. Typically, the parent polypeptide is a wild-type protein or wild-type protein domain. In the context of the present invention it is further preferred that a parent polypeptide (or parent segment) is the consensus sequence of two or more wild-type polypeptides (or wild-type segments). Further, the variants usable in the present invention may also be derived from homologs, orthologs, or paralogs of the parent polypeptide or from artificially constructed variant, provided that the variant exhibits at least one biological activity of the parent polypeptide. The changes in the amino acid sequence may be amino acid exchanges, insertions, deletions, N-terminal truncations, or C-terminal truncations, or any combination of these changes, which may occur at one or several sites. In preferred embodiments, a variant usable in the present invention exhibits a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes in the amino acid sequence (i.e. exchanges, insertions, deletions, N-terminal truncations, and/or C-terminal truncations). The amino acid exchanges may be conservative and/or non-conservative.

Semi-conservative and especially conservative amino acid substitutions, wherein an amino acid is substituted with a chemically related amino acid are preferred. Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Typical semi-conservative and conservative substitutions are:

| Amino acid | Conservative substitution | Semi-conservative substitution |
|---|---|---|
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein which have an alpha-helical or a beta-sheet structure.

Alternatively or additionally, a "variant" as used herein, can be characterized by a certain degree of sequence identity to the parent polypeptide or parent polynucleotide from which it is derived. More precisely, a protein variant in the context of the present invention exhibits at least 80% sequence identity to its parent polypeptide. A polynucleotide variant in the context of the present invention exhibits at least 80% sequence identity to its parent polynucleotide. Preferably, the sequence identity of protein variants is over a continuous stretch of 20, 30, 40, 45, 50, 60, 70, 80, 90, 100 or more amino acids. Preferably, the sequence identity of polynucleotide variants is over a continuous stretch of 60, 90, 120, 135, 150, 180, 210, 240, 270, 300 or more nucleotides.

The term "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Preferably, the polypeptide in question and the reference polypeptide exhibit the indicated sequence identity over a continuous stretch of 20, 30, 40, 45, 50, 60, 70, 80, 90, 100 or more amino acids or over the entire length of the reference polypeptide. Preferably, the polynucleotide in question and the reference polynucleotide exhibit the indicated sequence identity over a continuous stretch of 60, 90, 120, 135, 150, 180, 210, 240, 270, 300 or more nucleotides or over the entire length of the reference polypeptide.

Variants may additionally or alternatively comprise deletions of amino acids, which may be N-terminal truncations, C-terminal truncations or internal deletions or any combination of these. Such variants comprising N-terminal truncations, C-terminal truncations and/or internal deletions are referred to as "deletion variant" or "fragments" in the context of the present application. The terms "deletion variant" and "fragment" are used interchangeably herein. A fragment may be naturally occurring (e.g. splice variants) or it may be constructed artificially, preferably by gene-technological means. Preferably, a fragment (or deletion variant) has a deletion of up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acids at its N-terminus and/or at its C-terminus and/or internally as compared to the parent polypeptide, preferably at its N-terminus, at its N- and C-terminus, or at its C-terminus. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise. The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) available e.g. on http://www.ebi.ac.uk/Tools/clustalw/ or on http://www.ebi.ac.uk/Tools/clustalw2/index.html or on http://npsa-pbil.ibcp.fr/cgi-bin/npsa_automat.pl?page=/NPSA/npsa_clustalw.html. Preferred parameters used are the default parameters as they are set on http://www.ebi.ac.uk/Tools/clustalw/ or http://www.ebi.ac.uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. BLAST polynucleotide searches are performed with the BLASTN program, score=100, word length=12, to obtain homologous polynucleotide sequences. BLAST protein searches are performed with the BLASTP program, score=50, word length=3, to obtain homologous amino acid sequences. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:I54-I62) or Markov random fields. When percentages of sequence identity are referred to in the present application, these percentages are calculated in relation to the full length of the longer sequence, if not specifically indicated otherwise.

"Hybridization" can also be used as a measure of sequence identity or homology between two nucleic acid sequences. A nucleic acid sequence encoding the S100 protein or a portion thereof can be used as a hybridization probe according to standard hybridization techniques. The hybridization of a S100 probe to DNA or RNA from a test source is an indication of the presence of the S100 DNA or RNA in the test source. Hybridization conditions are known to those skilled in the art and can be found, for example, in Current Protocols in Molecular Biology, John Wiley & Sons, N.Y., 6.3.1-6.3.6, 1991. "Moderate hybridization conditions" are defined as equivalent to hybridization in 2× sodium chloride/sodium citrate (SSC) at 30° C., followed by a wash in 1×SSC, 0.1% SDS at 50° C. "Highly stringent conditions" are defined as equivalent to hybridization in 6× sodium chloride/sodium citrate (SSC) at 45° C., followed by a wash in 0.2×SSC, 0.1% SDS at 65° C.

Additionally or alternatively a deletion variant may occur not due to structural deletions of the respective amino acids as described above, but due to these amino acids being inhibited or otherwise not able to fulfill their biological function. Typically, such functional deletion occurs due to the insertions to or exchanges in the amino acid sequence that changes the functional properties of the resultant protein, such as but not limited to alterations in the chemical properties of the resultant protein (i.e. exchange of hydrophobic amino acids to hydrophilic amino acids), alterations in the post-translational modifications of the resultant protein (e.g. post-translational cleavage or glycosylation pattern), or alterations in the secondary or tertiary protein structure. Additionally or alternatively, a functional deletion may also occur due to transcriptional or post-transcriptional gene silencing (e.g. via siRNA) or the presence or absence of inhibitory molecules such as but not limited to protein inhibitors or inhibitory antibodies.

In the context of the present invention it is preferred that a protein (or a segment or a domain or an epitope) being "functionally deleted" refers to the fact that the amino acids or nucleotides of the corresponding sequence are either deleted or present but not fulfilling their biological function.

The term "expression level" (of a gene) refers to the amount of gene product present in the body or a sample at a certain point of time. The expression level can e.g. be measured/quantified/detected by means of the protein or mRNA expressed from the gene. The expression level can for example be quantified by normalizing the amount of gene product of interest present in a sample with the total amount of gene product of the same category (total protein or mRNA) in the same sample or a reference sample (e.g. a sample taken at the same time from the same individual or a part of identical size (weight, volume) of the same sample) or by identifying the amount of gene product of interest per defined sample size (weight, volume, etc.). The expression level can be measured or detected by means of any method as known in the art, e.g. methods for the direct detection and quantification of the gene product of interest (such as mass spectrometry) or methods for the indirect detection and measurement of the gene product of interest that usually work via binding of the gene product of interest with one or more different molecules or detection means (e.g. primer(s), probes, antibodies, protein scaffolds) specific for the gene product of interest. The determination of the level of gene copies comprising also the determination of the absence or presence of one or more fragments (e.g. via nucleic acid probes or primers, e.g. quantitative PCR, Multiplex ligation-dependent probe amplification (MLPA) PCR) is also within the knowledge of the skilled artisan.

As used herein, an "individual" means any mammal, reptile or bird that may benefit from the present invention. Preferably, an individual is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. It is particularly preferred that the "individual" is a human being.

The terms "diseased individual", "µl individual" "individual suffering from a disease" or "patient" are used interchangeably and refer to any mammal, reptile or bird that may benefit from a prognosis, diagnosis, identification or treatment of a disease or disorder. Preferably, a "patient" is selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, gorillas and human beings. It is particularly preferred that the "patient" is a human being.

The term "healthy individual", as used herein, refers to any mammal, reptile or bird not suffering from a certain disease. However, such healthy individual may possibly suffer from another disease not tested or known. Accordingly, in the context of the present invention a healthy individual does not have a cardiac disorder but may still suffer from a different disease such as e.g. a cold.

The terms "disease" and "disorder" are used interchangeably herein, referring to an abnormal condition, especially an abnormal medical condition such as an illness or injury, wherein a tissue, an organ or an individual is not able to efficiently fulfil its function anymore. Typically, but not necessarily, a disease is associated with specific symptoms or signs indicating the presence of such disease. The presence of such symptoms or signs may thus, be indicative for a tissue, an organ or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a tissue, organ or organism to fulfil its function efficiently, whereas the "bettering" of a disease is typically characterised by an increase in the ability of a tissue, an organ or an individual to fulfil its function efficiently. A tissue, an organ or an individual being at "risk of developing" a disease is in a healthy state but shows potential of a disease emerging. Typically, the risk of developing a disease is associated with early or weak signs or symptoms of such disease. In such case, the onset of the disease may still be prevented by treatment. Examples of a disease include but are not limited to traumatic diseases, inflammatory diseases, infectious diseases, cardiac disorders, cutaneous conditions, endocrine diseases, intestinal diseases, neurological disorders, joint diseases, genetic disorders, autoimmune diseases, and various types of cancer. Example as of cardiac disorders include but are not limited to postischemic contractile dysfunction, congestive heart failure, cardiogenic shock, septic shock, myocardial infarction, primary or secondary cardiomyopathy, dysfunction of heart valves, and ventricular disorder. Primary cardiomyopathy includes inherited cardiomyopathy and cardiomyopathy caused by spontaneous mutations. The secondary cardiomyopathy includes ischemic cardiomyopathy caused by arteriosclerosis, dilated cardiomyopathy caused by infection or intoxication of the myocard, hypertensive heart disease caused by pulmonary arterial und/or arterial hypertension and diseases of the heart valves.

"Symptoms" of a disease are implication of the disease noticeable by the tissue, organ or organism having such disease and include but are not limited to pain, weakness, tenderness, strain, stiffness, and spasm of the tissue, an organ or an individual. "Signs" or "signals" of a disease include but are not limited to the change or alteration such as the presence, absence, increase or elevation, decrease or decline, of specific indicators such as biomarkers or molecular markers, or the development, presence, or worsening of symptoms.

A disorder may be acquired or congenital. In this context, the term "acquired" means that the medical condition, i.e., the disorder, developed post-fetally. Such an acquired disorder in the context of the present invention may be a myocardial infarction. Congenital disorders involve defects to a developing fetus which may be the result of genetic abnormalities, errors of morphogenesis, or chromosomal abnormalities. Genetic diseases or disorders are all congenital, though they may not be expressed or recognized until later in life. Congenital disorders in the context of the present invention are, for example, Nemaline myopathy, Myotubular myopathy, or Centronuclear myopathy. Furthermore, in the context of the present invention, the cardiac disorder may be acute or chronic. For example, an acute cardiac disorder is acute heart failure, an acute skeletal muscle disorder is Rhabdomyolysis. A chronic cardiac muscle disease is, for example, chronic heart failure. The cardiac disorder may be due to the muscular malfunction which may be associated with defective calcium cycling and/or defective contractile performance in the muscle cells, preferably the cardiomyocytes. Defective calcium cycling in myocytes may be a result of reduced calcium content in the sarcoplasmic reticulum, reduced release of calcium from the sarcoplasmic reticulum during excitation-contraction coupling, calcium leakage from the sarcoplasmic reticulum, for example, due to a leaky RyR sarcoplasmic reticulum calcium release channel, increased calcium spark frequency, or reduced or slowed re-uptake of calcium into the sarcoplasmic reticulum and/or the mitochondria after contraction, for example, due to a malfunctioning or non-functioning sarcoplasmic/endoplasmic reticulum calcium ATPase (SERCA). Without being bound to this theory, it is assumed that a defective calcium cycling is one of the major reasons for defective contractile performance, e.g., contractile dysfunction, of muscle cells. Thus, it is assumed that enhancing or restoring calcium cycling also enhances and/or restores contractile performance. Almost all cardiac disorders/diseases are a result of contractile dysfunction of the respective muscle cells. For example, in cardiac arrhythmias, the cardiac muscle contraction is not precisely timed. This may have lethal consequences.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in an individual that have previously had the disorder(s); and (e) limiting or preventing recurrence of symptoms in individuals that were previously symptomatic for the disorder(s).

As used herein, "prevent", "preventing", "prevention", or "prophylaxis" of a disease or disorder means preventing that such disease or disorder occurs in patient.

The term "enhancing" in the context of the present invention means that the particular function is improved independently of whether the function is normal or defective, i.e., the muscle cell is healthy or diseased. Preferably, "enhancing" means that the particular function is enhanced by at least 15%, preferably by at least 25%, preferably by at least 35%, more preferably by at least 45%, and most preferably by at least 50% compared to a control setting. The term "enhancing the cardiac power" specifically refers to enhancing the function of the heart, e.g. by increasing the muscle function, contractile performance, and/or calcium handling of the heart. Preferably, the control setting is the muscle function, contractile performance, and/or calcium handling of a healthy patient or the average of a group of healthy patients.

As used herein, "administering" includes in vivo administration, as well as administration directly to tissue ex vivo, such as vein grafts.

An "effective amount" or "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Herein "therapeutic window" refers to the range of a drug dosage which is suitable to treat a specific disease effectively whilst staying within the safety range, i.e. the dosages of a pharmaceutical which is between the amount that provides therapeutical effects (effective dose) and the amount that results in more adverse effects than desired effects. Preferably, a therapeutic window refers to the range of manipulated myocardial S100A1 protein levels that either result in a biologically or therapeutically relevant performance enhancing effect independent of means to constitutively or conditionally manipulate expression levels such as by vector-based cardiac delivery of S100A1 cDNA or any other chemical, pharmaceutical or physical means to variably regulate or modulate cardiac S100A1 expression.

The term "inotropic action" with respect to an agent means that said agent affects the force of muscle contraction irrespective of the muscle type. "Positive inotropic action" means that the force of muscle contraction is increased, wherein "negative inotropic action" means that the force of muscle contraction is decreased. A positive inotropic fragment or variant of the present invention exhibits a positive inotropic action, preferably in vitro as well as in vivo. The inotropic effect of an agent, e.g., of the fragment or variant of the present invention, can be readily determined in vitro, for example, by determining calcium transients in stimulated myocytes with and without the agent/peptide to be tested. For example, calcium transients can be assessed in FURA2-AM field-stimulated cardiomyocytes employing epifluorescence digitalized microscopy (Most et al., 2004, J. Clin. Invest. 114: 1550-1563, page 1561). Any fluorescent calcium indicator can be used instead of FURA-2AM such as a member of the Fluo calcium indicator family or Rhod-2AM. The underlying principal remains the same. Alternatively, calcium transient measurements in patch-clamped isolated cardiomyocytes (Kettlewell/Most et al., 2005, J. Mol. Cell. Cardiol., 200: 900-910, page 901) may also be used. The positive inotropic effect of a fragment or variant can also be tested in vivo, for example, by determining the contractile performance by left ventricular catherization in anesthetized mice with and without administration of the peptide. Usually, in this experiment, contractility is described as the first derivative of maximal left ventricular pressure rise (+dp/dt max) (Most et al., 2004, J. Clin. Invest. 114: 1550-1563; Most et al., 2006, Circulation 114; 1258-1268) Alternatively, echocardiography (Most et al., 2006, Circulation 114; 1258-1268) can be used.

The terms "pharmaceutical", "medicament" and "thug" are used interchangeably herein referring to a substance and/or a combination of substances being used for the identification, prevention or treatment of a tissue status or disease.

"Pharmaceutically acceptable" means approved by a regulatory agency of the Federal or a state government or listed in the U.S. Pharmacopeia or other generally recognized pharmacopeia for use in animals, and more particularly in humans. The term "pharmaceutically acceptable salt" refers to a salt of the protein or peptide of the present invention. Suitable pharmaceutically acceptable salts include acid addition salts which may, for example, be formed by mixing a solution of the peptide of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the peptide carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

The term "active ingredient" refers to the substance in a pharmaceutical composition or formulation that is biologically active, i.e. that provides pharmaceutical value. A pharmaceutical composition may comprise one or more active ingredients which may act in conjunction with or independently of each other. The active ingredient can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as but not limited to those derived from sodium, potassium, ammonium, calcium, ferric hydroxides, isopropylamine, triethylamine, 2-ethylamino ethanol, histidine, procaine, and the like.

The terms "preparation" and "composition" are intended to include the formulation of the active compound with encapsulating material as a carrier providing a capsule in which the active component with or without other carriers, is surrounded by a carrier, which is thus in association with it.

The term "carrier", as used herein, refers to a pharmacologically inactive substance such as but not limited to a diluent, excipient, or vehicle with which the therapeutically active ingredient is administered. Such pharmaceutical carriers can be liquid or solid. Liquid carrier include but are not limited to sterile liquids, such as saline solutions in water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

Suitable pharmaceutical "excipients" include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The term "adjuvant" refers to agents that augment, stimulate, activate, potentiate, or modulate the immune response to the active ingredient of the composition at either the cellular or humoral level, e g immunologic adjuvants stimulate the response of the immune system to the actual antigen, but have no immunological effect themselves. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g polyarginine or polylysine).

Embodiments

In a first aspect, the present invention relates to a S100 protein or a nucleic acid encoding said S100 protein for use in treating a cardiac disease by enhancing the cardiac power in an individual suffering from or at risk of developing said cardiac disease, wherein the concentration of the S100 protein in the myocardium of said individual is increased to be within the therapeutic window. Accordingly, the concentration of the S100 protein in the myocardium of said individual is increased to be within the range of manipulated myocardial S100 protein levels that either result in a biologically or therapeutically relevant performance enhancing effect.

Preferably, the cardiac power is enhanced by improving the muscle function, contractile performance, and/or calcium handling of the cardiomyocytes. Preferably, the force of muscle contraction is increased. In preferred embodiments, the cardiac power is enhanced by at least 15%, preferably by at least 25%, more preferably by at least 35%, most preferably by at least 45%, and most preferably by at least 50% compared to a control setting. Preferably, the control setting is the muscle function, contractile performance, and/or calcium handling of a healthy patient or the average of a group of healthy patients.

In preferred embodiments, the cardiac power is enhanced by the S100 protein or the nucleic acid encoding said S100 protein, which exhibits one or more of the functions selected from the list consisting of an anti-arrhythmic potential, anti-apoptotic potential, the ability to reduce calcium spark frequency, the ability to prevent and/or reduce calcium leakage from the sarcoplasmic reticulum, and the ability to restore hemodynamic function preferably in an individual suffering from heart failure.

Preferably, the S100 protein or the nucleic acid encoding said S100 protein, exhibits an anti-arrhythmic potential on cardiomyocytes, and thus, is preferably capable of protecting cardiomyocytes and heart tissue from arrhythmias, preferably from catecholamine triggered arrhythmias, preferably from ventricular arrhythmias which frequently are the cause of sudden cardiac death. Preferably, the S100 protein or the nucleic acid encoding said S100 protein, exhibit the ability of protecting an individual from lethal ventricular tachyarrhythmias, preferably from (β-adrenergic receptor (βAR) triggered lethal ventricular tachyarrhythmias, preferably from catecholamine triggered lethal ventricular tachyarrhythmias.

In further preferred embodiments, the S100 protein or the nucleic acid encoding said S100 protein, has the ability to reduce calcium spark frequency in cardiomyocytes. Preferably the calcium spark frequency in cardiomyocytes is reduced by at least 15%, preferably at least 25%, more preferably at least 30%, and most preferably at least 40% compared to control cardiomyocytes not in contact with said peptides.

In further embodiments, the S100 protein or the nucleic acid encoding said S100 protein, protects cardiomyocytes from apoptotic cell death, preferably from calcium-induced apoptotic cell death, preferably from sarcoplasmic reticulum calcium leakage triggered apoptotic cell death. Thus, preferably, the S100 protein or the nucleic acid encoding said S100 protein, exhibits anti-apoptotic potential. Preferably, the S100 protein or the nucleic acid encoding said S100 protein, prevent apoptotic cell death in failing myocardium in vivo, i.e., protect cardiomyocytes in failing myocardium from apoptotic cell death in vivo. Preferably the extent of apoptotic cell death is reduced in the cells treated with the peptide according to the present invention compared to a control group by at least 20%, preferably by at least 30%, more preferably by at least 40%, and even more preferably by at least 50%, and most preferably by at least 60%.

In another preferred embodiment, the S100 protein or the nucleic acid encoding said S100 protein, has the ability to prevent and/or reduce calcium leakage from the sarcoplasmic reticulum, preferably in quiescent myocytes such as skeletal muscle cells and cardiomyocytes. In a particularly preferred embodiment, the S100 protein or the nucleic acid encoding said S100 protein, exhibits anti-arrhythmic potential and prevent and/or reduces calcium leakage as described above.

In another preferred embodiment, the S100 protein or the nucleic acid encoding said S100 protein, exhibits the ability of restoring hemodynamic function in vivo. Preferably, the S100 protein or the nucleic acid encoding said S100 protein, restores hemodynamic function in an individual suffering from heart failure such as during or after myocardial infarction. Preferably, the peptides of the present invention exhibit anti-arrhythmic potency and the ability of restoring hemodynamic function in vivo.

In a particularly preferred embodiment, the S100 protein or the nucleic acid encoding said S100 protein, exhibits one or more, e.g. 1, 2, 3, 4, or 5, preferably all of the above functions, i.e., anti-arrhythmic potential, anti-apoptotic potential, the ability to reduce calcium spark frequency, the ability to prevent and/or reduce calcium leakage from the sarcoplasmic reticulum, the ability to restore hemodynamic function preferably in an individual suffering from heart failure.

In preferred embodiments, the concentration of the S100 protein in the myocardium of said individual is increased to no more than the 50 fold concentration in a healthy individual. Thus, preferably, the concentration of the S100 protein within the myocardium is increased to the 2 fold, 3 fold, 4 fold, 5 fold, 6 fold, 7 fold, 8 fold, 9 fold, 10 fold, 11 fold, 12 fold, 13 fold, 14 fold, 15 fold, 20 fold, 25 fold, 30 fold, 35 fold, 40 fold, 45 fold, or 50 fold, of the concentration in a healthy individual. Preferably, the concentration of the S100 protein in the myocardium of said individual is increased to no more than the 20 fold, more preferably the 8 fold, most preferably the 4 fold, concentration in a healthy individual. In preferred embodiments of the first aspect the S100 protein or the nucleic acid encoding said S100 according to claim 1, wherein the concentration of the S100 protein in the myocardium of an individual is increased 2-50 fold, preferably 2-20 fold, more preferably 4-8 fold, more preferably 4 fold.

Preferably, the concentration of the S100 protein within the myocardium is increased to be below the 55 fold, 60 fold, 65 fold, 70 fold, 75 fold, 80 fold, 85 fold, 90 fold, 95 fold, 100 fold, 150 fold, 200 fold, 300 fold, 400 fold, or 500 fold, concentration in a healthy individual.

In embodiments of the first aspect, the S100 protein is the naturally occurring S100 protein which is preferably selected from the group consisting of S100β, S100A1, S100A2, S100A4 and S100A6. S100A1 is particularly preferred.

In embodiments of the first aspect of the present invention, the S100 protein is a fragment or variant of a naturally occurring S100 protein, which exhibits a positive inotropic action, i.e. a fragment or variant of a naturally occurring S100 protein which increases the force of muscle contraction. In preferred embodiments of the present invention said fragment or variant is a positive inotropic peptide which preferably exhibits the ability to enhance contractile performance and/or calcium cycling in cardiomyocytes.

In preferred embodiments, the cardiac power is enhanced by said fragment or variant which exhibits one or more of the functions described in detail above, selected from the list consisting of an anti-arrhythmic potential, anti-apoptotic potential, the ability to reduce calcium spark frequency, the ability to prevent and/or reduce calcium leakage from the sarcoplasmic reticulum, and the ability to restore hemodynamic function preferably in an individual suffering from heart failure. In a particularly preferred embodiment, the fragment or variant exhibits one or more, e.g. 1, 2, 3, 4, or 5, preferably all of the above detailed functions, i.e., anti-arrhythmic potential, anti-apoptotic potential, the ability to reduce calcium spark frequency, the ability to prevent and/or reduce calcium leakage from the sarcoplasmic reticulum, the ability to restore hemodynamic function preferably in an individual suffering from heart failure.

In preferred embodiments of the present invention, said fragment or variant is a positive inotropic peptide comprising or consisting of a hydrophilic domain and/or one or more membrane penetration enhancing domains, and an S100A1 protein derived domain, wherein said S100A1 protein derived domain consists of 4 to 9 consecutive amino acids of the inotropic motif:

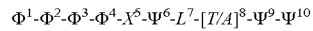

and comprises at least the core motif $\Phi^4\text{-}X^5\text{-}\Psi^6\text{-}L^7$, wherein $\Phi$ and $\Psi$ are in each instance an independently selected hydrophobic non-aromatic amino acid, and X is any amino acid, and wherein said peptide has a total length of maximally 100 amino acids and the peptide exhibits a positive inotropic action, preferably of maximally 10, 11, 12, 13, 14, 15, 16, 17, 18, 19, 20, 21, 22, 23, 24, 25, 30, 35, 40, 45, 50, 55, 60, 65, 70, 75, 80, 85, 90, or 95 amino acids.

In a preferred embodiment, the inotropic peptide has a length of between 10 and 80 amino acids, more preferably of between 10 and 70 amino acids, more preferably of between 10 and 60 amino acids, more preferably between 10 and 50 amino acids, even more preferably between 10 and 40 amino acids, even more preferably between 10 and 30 amino acids, most preferably the peptide has a length of between 10 and 15 amino acids. In a preferred embodiment, the peptide is 13, 14 or 15 amino acids long. Preferably, the peptide with the exception of the S100A1 protein derived domain as specified above significantly differs from the carboxy-terminal amino acids of an S100 calcium binding protein A1, preferably from an S100 calcium binding protein selected from the group consisting of S100 calcium binding protein A1, S100 calcium binding protein Z, S100 calcium binding protein T, S100 calcium binding protein S, and S100 protein α-chain, and most preferably significantly differs from the carboxy-terminus of any S100 calcium binding protein. More preferably, the peptide with the exception S100A1 protein derived domain significantly differs from the amino acid sequence of an S100 calcium binding protein A1, preferably from an S100 calcium binding protein selected from the group consisting of S100 calcium binding protein A1, S100 calcium binding protein Z, S100 calcium binding protein T, S100 calcium binding protein S, and S100 protein α-chain, and most preferably significantly differs from the amino acid sequence of any S100 calcium binding protein. Preferably, the amino acid sequences are at least 80% different, more preferably at least 85%, more preferably at least 90%, even more preferably at least 95%, and most preferably 100% different. The difference in the sequences may be assessed by aligning the polypeptide sequences.

In a preferred embodiment the peptide further comprises one or more of the elements selected from the group consisting of one or more epitope-tag(s), and a peptide targeting domain. It is also preferred that the peptide further comprises a hydrophilic domain, if it already comprised a membrane penetration enhancing domain or further comprises a membrane penetration enhancing domain, if it already comprised a hydrophilic domain. These further elements may be linked directly or indirectly to N- or C-terminally to the other elements of the peptide, preferably to the N-terminus of the hydrophilic domain or one or more membrane penetration enhancing domain. In further embodiments of the present invention said fragment or variant is a positive inotropic peptide comprising or consisting of an S100A1 protein derived domain, wherein said S100A1 protein derived domain consists of 7 to 9 consecutive amino acids of the inotropic motif:

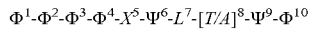

and comprises at least the core motif $\Phi^4$-$X^5$-$\Psi^6$-$L^7$, wherein $\Phi$ and $\Psi$ are in each instance an independently selected hydrophobic non-aromatic amino acid, and X is any amino acid, under the proviso that the N-terminal amino acid of said S100A protein derived domain consisting of 9 consecutive amino acids is $\Phi^1$, and wherein said peptide has a total length of maximally 100, preferably of maximally 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, or 95 amino acids. The positive inotropic peptide preferably exhibits a positive inotropic action. Furthermore, in the embodiment, wherein the S100A1 protein derived domain consists of 9 consecutive amino acids the amino acids are the following: $\Phi^1$-$\Phi^2$-$\Phi^3$-$\Phi^4$-$X^5$-$\Psi^6$-$L^7$-$[T/A]^8$-$\Psi^9$. In a further preferred embodiments the N-terminal amino acid of said S100A protein derived domain consisting of 7 or 8 consecutive amino acids is $\Phi^1$; i.e. the S100A1 protein derived domain consists of $\Phi^1$-$\Phi^2$-$\Phi^3$-$\Phi^4$-$X^5$-$\Psi^6$-$L^7$-$[T/A]^8$ or $\Phi^1$-$\Phi^2$-$\Phi^3$-$\Phi^4$-$X^5$-$\Psi^6$-$L^7$. Thus, it is preferred that the proviso applies to S100A1 protein derived domain consisting of 7 to 9 consecutive amino acids. In a preferred embodiment, the peptide has a length of between 7 and 80 amino acids, more preferably of between 7 and 70 amino acids, more preferably of between 7 and 60 amino acids, more preferably between 7 and 50 amino acids, even more preferably between 7 and 40 amino acids, even more preferably between 7 and 30 amino acids, most preferably the peptide has a length of between 7 and 15 amino acids. In a preferred embodiment, the peptide is 7 to 9 or 7, 8, or 9 amino acids long. Preferably, the peptide with the exception of the S100A1 protein derived domain as specified above significantly differs from the carboxy-terminal amino acids of an S100 calcium binding protein A1, preferably from an S100 calcium binding protein selected from the group consisting of S100 calcium binding protein A1, S100 calcium binding protein Z, S100 calcium binding protein T, S100 calcium binding protein S, and S100 protein α-chain, and most preferably significantly differs from the carboxy-terminus of any S100 calcium binding protein. More preferably, the peptide with the exception S100A1 protein derived domain significantly differs from the amino acid sequence of an S100 calcium binding protein A1, preferably from an S100 calcium binding protein selected from the group consisting of S100 calcium binding protein A1, S100 calcium binding protein Z, S100 calcium binding protein T, S100 calcium binding protein S, and S100 protein α-chain, and most preferably significantly differs from the amino acid sequence of any S100 calcium binding protein. Preferably, the amino acid sequences are at least 80% different, more preferably at least 85%, more preferably at least 90%, even more preferably at least 95%, and most preferably 100% different. The difference in the sequences may be assessed by aligning the polypeptide sequences.

In a preferred embodiment the peptide further comprises one or more of the elements selected from the group consisting of a hydrophilic domain, a membrane penetration enhancing domain, one or more epitope-tag(s), and a peptide targeting domain, preferably a hydrophilic domain, a membrane penetration enhancing domain or a hydrophilic domain and a membrane penetration enhancing domain. These elements may be linked directly or indirectly to the N- or C-terminus of S100A1 protein derived domain. Preferably, to the N-terminus as described in more detail below.

For the purpose of the present invention two elements comprised in the positive inotropic peptides of the invention are "directly linked" if there is a peptide bond between an amino acid at the N-terminus of one element and an amino acid at the C-terminus of the other element. The term "indirectly linked" implies that there are one or more additional elements, preferably one or more amino acids between the respective N- and C-terminus of two elements. Such one, two, three, four or more amino acids are preferably linker. The term linker is used in the art to refer to a stretch of amino acids conferring flexibility. The skilled person is aware of a large number of linkers, which may be used in this context. Preferably, the length of the linker does not exceed 1, 2, 3, 4, or 5 amino acids to keep the overall length of the positive inotropic peptide of the invention at a minimum.

Said hydrophilic domain preferably comprises acidic, basic, and/or otherwise negatively or positively charged amino acids. In a particular preferred, the hydrophilic domain comprises or consists of the amino acid motif $\Lambda_4$-$\Theta_2$, wherein $\Lambda$ is in each instance independently selected from aspartate, glutamate, lysine, and arginine and $\Theta$ is an α-helix interrupter, preferably proline or glycine. Preferably, the hydrophilic domain comprises or consists of an amino acid sequence selected from the group consisting of [D/E]-[D/E]-[D/E]-[D/E]-[P/G]-[P/G], [K/R]-[D/E]-[D/E]-[D/E]-[P/G]-[P/G], [D/E]-[K/R]-[D/E]-[D/E]-[P/G]-[P/G], [D/E]-[D/E]-[K/R]-[D/E]-[P/G]-[P/G], [D/E]-[D/E]-[D/E]-[K/R]-[P/G]-[P/G], [K/R]-[K/R]-[D/E]-[D/E]-[P/G]-[P/G], [K/R]-[D/E]-[K/R]-[D/E]-[P/G]-[P/G], [K/R]-[D/E]-[D/E]-[K/R]-[P/G]-[P/G], [D/E]-[K/R]-[K/R]-[D/E]-[P/G]-[P/G], [D/E]-[K/R]-[D/E]-[K/R]-[P/G]-[P/G], [D/E]-[D/E]-[K/R]-[K/R]-[P/G]-[P/G], [K/R]-[K/R]-[K/R]-[D/E]-[P/G]-[P/G], [K/R]-[K/R]-[D/E]-[K/R]-[P/G]-[P/G], [K/R]-[D/E]-[K/R]-[K/R]-[P/G]-[P/G], [D/E]-[K/R]-[K/R]-[K/R]-[P/G]-[P/G], and [K/R]-[K/R]-[K/R]-[K/R]-[P/G]-[P/G]. Preferably, the hydrophilic domain comprises or consists of the amino acid sequence [D/E]-[K/R]-[D/E]-[D/E]-[P/G]-[P/G] (SEQ ID NO: 3). More preferably, the hydrophilic domain comprises or consists of an amino acid sequence selected from the group consisting of D-K-D-D-P-P (SEQ ID NO: 17), E-K-D-D-P-P (SEQ ID NO: 48), D-R-D-D-P-P (SEQ ID NO: 49), D-K-E-D-P-P (SEQ ID NO: 50), D-K-D-E-P-P (SEQ ID NO: 51), E-R-D-D-P-P (SEQ ID NO: 52), E-K-E-D-P-P (SEQ ID NO: 53), E-K-D-E-P-P (SEQ ID NO: 54), D-R-E-D-P-P (SEQ ID NO: 55), D-R-D-E-P-P (SEQ ID NO: 56), D-K-E-E-P-P (SEQ ID NO: 57), E-R-E-D-P-P (SEQ ID NO: 58), E-R-D-E-P-P (SEQ ID NO: 59), D-R-E-E-P-P (SEQ ID NO: 60), E-K-E-E-P-P (SEQ ID NO: 61), and E-R-E-E-P-P (SEQ ID NO: 62), wherein P-P in said sequences may be exchanged for G-G. Most preferably, the hydrophilic domain comprises or consists of the amino acid sequence D-K-D-D-P-P (SEQ ID NO: 17), wherein P-P in said sequences may also be G-G. Preferably, the hydrophilic domain is located within a peptide according to the present invention amino-terminally to the muscle function enhancing amino acid sequence, but could also be located carboxy-terminally to the muscle function enhancing amino acid sequence. In a particularly preferred embodiment, the C-terminus of said hydrophilic domain is directly or indirectly linked to the N-terminus of said inotropic domain and preferably the amino acid linked to said N-terminus is no hydrophobic non-aromatic amino acid.

Said membrane penetration enhancing domain may be any amino acid sequence that is capable of penetrating membranes as specified above, e.g., a cell-penetrating peptide (CCP). Such a domain may enable other macromolecules, such as peptides, proteins or nucleic acids, which normally do not possess the ability to traverse cell membranes, to penetrate intact cell membranes when said membrane penetration enhancing domain is attached to said macromolecule. Such membrane penetration enhancing domains may be derived from protein transduction domains, may be amphipathic peptides, or may be any other penetrating peptide. For example, the membrane penetration enhancing domain may be derived from the HIV Tat peptide, e.g. G-R-K-K-R-R-Q-R-R-R (SEQ ID NO: 63), the penetratin peptide, e.g. R-Q-I-K-I-W-F-Q-N-R-R-M-K-W-K-K (SEQ ID NO: 64) or K-K-W-K-M-R-R-N-Q-F-W-V-K-V-Q-R-G (SEQ ID NO: 65), the transportan peptide, e.g. G-W-T-L-N-S-A-G-Y-L-L-G-K-I-N-L-K-A-L-A-A-L-A-K-K-I-L (SEQ ID NO: 66), an MPG/Pep family member peptide, e.g. G-A-L-F-L-G-F-L-G-A-A-G-S-T-M-G-A-W-S-QP-K-K-K-R-K-V (SEQ ID NO: 67) or K-E-T-W-W-E-T-W-W-T-E-W-S-Q-P-K-K-K-R-K-V (SEQ ID NO: 68), or arginine rich peptides etc. (Deshayes et al., 2005, Cell. Mol. Life Sci. 62:1839-1849). Such a membrane penetration enhancing domain may be located amino-terminally or carboxy-terminally to the muscle function enhancing amino acid sequence within a peptide according to the present invention. Furthermore, a peptide according to the present invention may comprise more than one membrane penetration enhancing domain, for example, a peptide according to the present invention may contain 2, 3, 4, or 5 such domains.

In one embodiment, the peptide further comprises epitope-tag(s), and/or a peptide targeting domain. In another embodiment, the peptide further comprises one or more, e.g. one, two, three, or four of the elements selected from the group consisting of a hydrophilic domain, a membrane penetration enhancing domain, one or more epitope-tag(s), and a peptide targeting domain.

An epitope is a portion of a molecule to which an antibody binds. In the context of the present invention, an epitope is preferably a peptide-tag, for example, hemagglutinin-(HA-), FLAG-, myc-, or a poly-His-tag. Such an epitope tag may be used to locate the peptide of the present invention within a cell, for example, for determining whether the peptide penetrates, i.e., traverses, cell membranes and can be found inside an intact cell incubated with said peptide.

A peptide targeting domain in the context of the present invention may be any moiety that is suitable for targeting a peptide in vivo to a specific organ or specific cells. For example, a peptide targeting domain may be a peptide that specifically binds to a particular receptor which is specific for certain cells or a certain organ. Preferably, the presence of a peptide targeting domain within the peptide according to the present invention allows for specific targeting of cells or organs in a patient to which the peptide was administered systemically.

In a preferred embodiment, the core motif of the peptide is [V/I/M]-[A/G/S]-[A/V]-L (SEQ ID NO: 1). Preferably, said core motif is selected from the group consisting of the amino acid sequences V-G-A-L (SEQ ID NO: 4), I-A-A-L (SEQ ID NO: 5), V-S-V-L (SEQ ID NO: 6), M-G-A-L (SEQ ID NO: 7), V-A-A-L (SEQ ID NO: 8), and preferably is V-A-A-L (SEQ ID NO: 8).

In another preferred embodiment, the inotropic motif of the peptide is [V/I]-[V/I]-[L/M]-[V/I/M]-[A/G/S]-[A/V]-L-[T/A]-[V/A/I]-[A/M/V] (SEQ ID NO: 2). Preferably, said inotropic motif is selected from the group consisting of the amino acid sequences V-V-L-V-A-A-L-T-V-A (SEQ ID NO: 9), V-I-L-V-A-A-L-T-V-A (SEQ ID NO: 10), V-V-M-V-A-A-L-T-V-A (SEQ ID NO: 11), I-I-L-V-G-A-L-T-V-A (SEQ ID NO: 12), V-V-L-I-A-A-L-A-A-A (SEQ ID NO: 13), V-I-L-V-S-V-L-T-V-A (SEQ ID NO: 14), I-I-L-M-G-A-L-T-V-A (SEQ ID NO: 15), and V-V-M-V-A-A-L-T-V-V (SEQ ID NO: 16). Most preferably, said inotropic motif is V-V-L-V-A-A-L-T-V-A (SEQ ID NO: 9).

Ψ of the inotropic motif of the peptide is preferably in each instance independently selected from the group consisting of alanine, methionine, isoleucine, leucine, and valine, preferably alanine, methionine, isoleucine, and valine. Φ of the inotropic motif of the peptide of the first or second aspect is preferably in each instance independently selected from the group consisting of alanine, methionine, isoleucine, leucine, and valine, preferably methionine, isoleucine, leucine, and valine. In a particularly preferred embodiment of the peptide of the first or second aspect, Φ is in each instance independently selected from methionine, isoleucine, leucine, and valine, and Ψ is in each instance independently selected from alanine, methionine, isoleucine, and valine.

In another preferred embodiment, X is a small amino acid, wherein the small amino acid is preferably not proline. Preferably, X is selected from the group of amino acids consisting of glycine, alanine, serine, cysteine, threonine, and valine, more preferably X is selected from the group consisting of glycine, alanine, and serine. In a particularly preferred embodiment of the peptide of the first or second aspect, Φ is in each instance independently selected from methionine, isoleucine, leucine, and valine, Ψ is in each instance independently selected from alanine, methionine, isoleucine, and valine, and X is selected from glycine, alanine, serine, cysteine, threonine, and valine, preferably from glycine, alanine, and serine.

In a preferred embodiment, the inotropic motif of the peptide comprises or consists of an amino acid sequence selected from the group consisting of V-V-L-V-A-A-L-T-V-A (SEQ ID NO: 9), V-I-L-V-A-A-L-T-V-A (SEQ ID NO: 10), V-V-M-V-A-A-L-T-V-A (SEQ ID NO: 11), I-I-L-V-G-A-L-T-V-A (SEQ ID NO: 12), V-I-L-V-S-V-L-T-V-A (SEQ ID NO: 14), V-V-M-V-A-A-L-T-V-V (SEQ ID NO: 16), V-V-L-I-A-A-L-T-V-A (SEQ ID NO: 69), V-V-L-M-A-A-L-T-V-A (SEQ ID NO: 70), V-V-L-V-G-A-L-T-V-A (SEQ ID NO: 71), V-V-L-V-S-A-L-T-V-A (SEQ ID NO: 72), V-V-L-V-A-V-L-T-V-A (SEQ ID NO: 73), V-V-L-V-A-A-L-A-V-A (SEQ ID NO: 74), V-V-L-V-A-A-L-T-A-A (SEQ ID NO: 75), V-V-L-V-A-A-L-T-I-A (SEQ ID NO: 76), V-V-L-V-A-A-L-T-V-M (SEQ ID NO: 77), V-V-L-V-A-A-L-T-V-V (SEQ ID NO: 78), I-I-L-V-A-A-L-T-V-A (SEQ ID NO: 79), I-V-M-V-A-A-L-T-V-A (SEQ ID NO: 80), I-V-L-I-A-A-L-T-V-A (SEQ ID NO: 81), I-V-L-M-A-A-L-T-V-A (SEQ ID NO: 82), I-V-L-V-G-A-L-T-V-A (SEQ ID NO: 83), I-V-L-V-S-A-L-T-V-A (SEQ ID NO: 84), I-V-L-V-A-V-L-T-V-A (SEQ ID NO: 85), I-V-L-V-A-A-L-A-V-A (SEQ ID NO: 86), I-V-L-V-A-A-L-T-A-A (SEQ ID NO: 87), I-V-L-V-A-A-L-T-I-A (SEQ ID NO: 88), I-V-L-V-A-A-L-T-V-M (SEQ ID NO: 89), I-V-L-V-A-A-L-T-V-V (SEQ ID NO: 90), V-I-M-V-A-A-L-T-V-A (SEQ ID NO: 91), V-I-L-I-A-A-L-T-V-A (SEQ ID NO: 92), V-I-L-M-A-A-L-T-V-A (SEQ ID NO: 93), V-I-L-V-G-A-L-T-V-A (SEQ ID NO: 94), V-I-L-V-S-A-L-T-V-A (SEQ ID NO: 95), V-I-L-V-A-V-L-T-V-A (SEQ ID NO: 96), V-I-L-V-A-A-L-A-V-A (SEQ ID NO: 97), V-I-L-V-A-A-L-T-A-A (SEQ ID NO: 98), V-I-L-V-A-A-L-T-I-A (SEQ ID NO: 99), V-I-L-V-A-A-L-T-V-M (SEQ ID NO: 100), V-I-L-V-A-A-L-T-V-V (SEQ ID NO: 101), V-V-M-I-A-A-L-T-V-A (SEQ ID NO: 102), V-V-M-M-A-A-L-T-V-A (SEQ ID NO: 103), V-V-M-V-G-A-L-T-V-A (SEQ ID NO: 104), V-V-M-V-S-A-L-T-V-A (SEQ ID NO: 105), V-V-M-V-A-V-L-T-V-A (SEQ ID NO: 106), V-V-M-V-A-A-L-A-V-A (SEQ ID NO: 107), V-V-M-V-A-A-L-T-A-A (SEQ ID NO: 108), V-V-M-V-A-A-L-T-I-A (SEQ ID NO: 109), V-V-M-V-A-A-L-T-V-M (SEQ ID NO: 110), V-V-L-I-G-A-L-T-V-A (SEQ ID NO: 111), V-V-L-I-S-A-L-T-V-A (SEQ ID NO: 112), V-V-L-I-A-V-L-T-V-A (SEQ ID NO: 113), V-V-L-I-A-A-L-A-V-A (SEQ ID NO: 114), V-V-L-I-A-A-L-T-A-A (SEQ ID NO: 115), V-V-L-I-A-A-L-T-I-A (SEQ ID NO: 116), V-V-L-I-A-A-L-T-V-M (SEQ ID NO: 117), V-V-L-I-A-A-L-T-V-V (SEQ ID NO: 118), V-V-L-M-G-A-L-T-V-A (SEQ ID NO: 119), V-V-L-M-S-A-L-T-V-A (SEQ ID NO: 120), V-V-L-M-A-V-L-T-V-A (SEQ ID NO: 121), V-V-L-M-A-A-L-A-V-A (SEQ ID NO: 122), V-V-L-M-A-A-L-T-A-A (SEQ ID NO: 123), V-V-L-M-A-A-L-T-I-A (SEQ ID NO: 124), V-V-L-M-A-A-L-T-V-M (SEQ ID NO: 125), V-V-L-M-A-A-L-T-V-V (SEQ ID NO: 126), V-V-L-V-G-V-L-T-V-A (SEQ ID NO: 127), V-V-L-V-G-A-L-A-V-A (SEQ ID NO: 128), V-V-L-V-G-A-L-T-A-A (SEQ ID NO: 129), V-V-L-V-G-A-L-T-I-A (SEQ ID NO: 130), V-V-L-V-G-A-L-T-V-M (SEQ ID NO: 131), V-V-L-V-G-A-L-T-V-V (SEQ ID NO: 132), V-V-L-V-S-V-L-T-V-A (SEQ ID NO: 133), V-V-L-V-S-A-L-A-V-A (SEQ ID NO: 134), V-V-L-V-S-A-L-T-A-A (SEQ ID NO: 135), V-V-L-V-S-A-L-T-I-A (SEQ ID NO: 136), V-V-L-V-S-A-L-T-V-M (SEQ ID NO: 137), V-V-L-V-S-A-L-T-V-V (SEQ ID NO: 138), V-V-L-V-A-V-L-A-V-A (SEQ ID NO: 139), V-V-L-V-A-V-L-T-A-A (SEQ ID NO: 140), V-V-L-V-A-V-L-T-I-A (SEQ ID NO: 141), V-V-L-V-A-V-L-T-V-M (SEQ ID NO: 142), V-V-L-V-A-V-L-T-V-V (SEQ ID NO: 143), V-V-L-V-A-A-L-A-A-A (SEQ ID NO: 144), V-V-L-V-A-A-L-A-I-A (SEQ ID NO: 145), V-V-L-V-A-A-L-A-V-M (SEQ ID NO: 146), V-V-L-V-A-A-L-A-V-V (SEQ ID NO: 147), V-V-L-V-A-A-L-T-A-M (SEQ ID NO: 148), V-V-L-V-A-A-L-T-A-V (SEQ ID NO: 149), V-V-L-V-A-A-L-T-I-M (SEQ ID NO: 150), V-V-L-V-A-A-L-T-I-V (SEQ ID NO: 151), I-I-M-V-A-A-L-T-V-A (SEQ ID NO: 152), I-I-L-I-A-A-L-T-V-A (SEQ ID NO: 153), I-I-L-M-A-A-L-T-V-A (SEQ ID NO: 154), I-I-L-V-S-A-L-T-V-A (SEQ ID NO: 155), I-I-L-V-A-V-L-T-V-A (SEQ ID NO: 156), I-I-L-V-A-A-L-A-V-A (SEQ ID NO: 157), I-I-L-V-A-A-L-T-A-A (SEQ ID NO: 158), I-I-L-V-A-A-L-T-I-A (SEQ ID NO: 159), I-I-L-V-A-A-L-T-V-M (SEQ ID NO: 160), I-I-L-V-A-A-L-T-V-V (SEQ ID NO: 161), I-V-M-I-A-A-L-T-V-A (SEQ ID NO: 162), I-V-M-M-A-A-L-T-V-A (SEQ ID NO: 163), I-V-M-V-G-A-L-T-V-A (SEQ ID NO: 164), I-V-M-V-S-A-L-T-V-A (SEQ ID NO: 165), I-V-M-V-A-V-L-T-V-A (SEQ ID NO: 166), I-V-M-V-A-A-L-A-V-A (SEQ ID NO: 167), I-V-M-V-A-A-L-T-A-A (SEQ ID NO: 168), I-V-M-V-A-A-L-T-I-A (SEQ ID NO: 169), I-V-M-V-A-A-L-T-V-M (SEQ ID NO: 170), I-V-M-V-A-A-L-T-V-V (SEQ ID NO: 171), I-V-L-I-G-A-L-T-V-A (SEQ ID NO: 172), I-V-L-I-S-A-L-T-V-A (SEQ ID NO: 173), I-V-L-I-A-V-L-T-V-A (SEQ ID NO: 174), I-V-L-I-A-A-L-A-V-A (SEQ ID NO: 175), I-V-L-I-A-A-L-T-A-A (SEQ ID NO: 176), I-V-L-I-A-A-L-T-I-A (SEQ ID NO: 177), I-V-L-I-A-A-L-T-V-M (SEQ ID NO: 178), I-V-L-I-A-A-L-T-V-V (SEQ ID NO: 179), I-V-L-M-G-A-L-T-V-A (SEQ ID NO: 180), I-V-L-M-S-A-L-T-V-A (SEQ ID NO: 181), I-V-L-M-A-V-L-T-V-A (SEQ ID NO: 182), I-V-L-M-A-A-L-A-V-A (SEQ ID NO: 183), I-V-L-M-A-A-L-T-A-A (SEQ ID NO: 184), I-V-L-M-A-A-L-T-I-A (SEQ ID NO: 185), I-V-L-M-A-A-L-T-V-M (SEQ ID NO: 186), I-V-L-M-A-A-L-T-V-V (SEQ ID NO: 187), I-V-L-V-G-V-L-T-V-A (SEQ ID NO: 188), I-V-L-V-G-A-L-A-V-A (SEQ ID NO: 189), I-V-L-V-G-A-L-T-A-A (SEQ ID NO: 190), I-V-L-V-G-A-L-T-I-A (SEQ ID NO: 191), I-V-L-V-G-A-L-T-V-M (SEQ ID NO: 192), I-V-L-V-G-A-L-T-V-V (SEQ ID NO: 193), I-V-L-V-S-V-L-T-V-A (SEQ ID NO: 194), I-V-L-V-S-A-L-A-V-A (SEQ ID NO: 195), I-V-L-V-S-A-L-T-A-A (SEQ ID NO: 196), I-V-L-V-S-A-L-T-I-A (SEQ ID NO: 197), I-V-L-V-S-A-L-T-V-M (SEQ ID NO: 198), I-V-L-V-S-A-L-T-V-V (SEQ ID NO: 199), I-V-L-V-A-V-L-A-V-A (SEQ ID NO: 200), I-V-L-V-A-V-L-T-A-A (SEQ ID NO: 201), I-V-L-V-A-V-L-T-I-A (SEQ ID NO: 202), I-V-L-V-A-V-L-T-V-M (SEQ ID NO: 203), I-V-L-V-A-V-L-T-V-V (SEQ ID NO: 204), I-V-L-V-A-A-L-A-A-A (SEQ ID NO: 205), I-V-L-V-A-A-L-A-I-A (SEQ ID NO: 206), I-V-L-V-A-A-L-A-V-M (SEQ ID NO: 207), I-V-L-V-A-A-L-A-V-V (SEQ ID NO: 208), I-V-L-V-A-A-L-T-A-M (SEQ ID NO: 209), I-V-L-V-A-A-L-T-A-V (SEQ ID NO: 210), I-V-L-V-A-A-L-T-I-M (SEQ ID NO: 211), I-V-L-V-A-A-L-T-I-V (SEQ ID NO: 212), V-I-M-I-A-A-L-T-V-A (SEQ ID NO: 213), V-I-M-M-A-A-L-T-V-A (SEQ ID NO: 214), V-I-M-V-G-A-L-T-V-A (SEQ ID NO: 215), V-I-M-V-S-A-L-T-V-A (SEQ ID NO: 216), V-I-M-V-A-V-L-T-V-A (SEQ ID NO: 217), V-I-M-V-A-A-L-A-V-A (SEQ ID NO: 218), V-I-M-V-A-A-L-T-A-A (SEQ ID NO: 219), V-I-M-V-A-A-L-T-I-A (SEQ ID NO: 220), V-I-M-V-A-A-L-T-V-M (SEQ ID NO: 221), V-I-M-V-A-A-L-T-V-V (SEQ ID NO: 222), V-I-L-I-G-A-L-T-V-A (SEQ ID NO: 223), V-I-L-I-S-A-L-T-V-A (SEQ ID NO: 224), V-I-L-I-A-V-L-T-V-A (SEQ ID NO: 225), V-I-L-I-A-A-L-A-V-A (SEQ ID NO: 226), V-I-L-I-A-A-L-T-A-A (SEQ ID NO: 227), V-I-L-I-A-A-L-T-I-A (SEQ ID NO: 228), V-I-L-I-A-A-L-T-V-M (SEQ ID NO: 229), V-I-L-I-A-A-L-T-V-V (SEQ ID NO: 230), V-I-L-M-G-A-L-T-V-A (SEQ ID NO: 231), V-I-L-M-S-A-L-T-V-A (SEQ ID NO: 232), V-I-L-M-A-V-L-T-V-A (SEQ ID NO: 233), V-I-L-M-A-A-L-A-V-A (SEQ ID NO: 234), V-I-L-M-A-A-L-T-A-A (SEQ ID NO: 235), V-I-L-M-A-A-L-T-I-A (SEQ ID NO: 236), V-I-L-M-A-A-L-T-V-M (SEQ ID NO: 237), V-I-L-M-A-A-L-T-V-V (SEQ ID NO: 238), V-I-L-V-G-V-L-T-V-A (SEQ ID NO: 239), V-I-L-V-G-A-L-A-V-A (SEQ ID NO: 240), V-I-L-V-G-A-L-T-A-A (SEQ ID NO: 241), V-I-L-V-G-A-L-T-I-A (SEQ ID NO: 242), V-I-L-V-G-A-L-T-V-M (SEQ ID NO: 243), V-I-L-V-G-A-L-T-V-V (SEQ ID NO: 244), V-I-L-V-S-A-L-A-V-A (SEQ ID NO: 245), V-I-L-V-S-A-L-T-A-A (SEQ ID NO: 246), V-I-L-V-S-A-L-T-I-A (SEQ ID NO: 247), V-I-L-V-S-A-L-T-V-M (SEQ ID NO: 248), V-I-L-V-S-A-L-T-V-V (SEQ ID NO: 249), V-I-L-V-A-V-L-A-V-A (SEQ ID NO: 250), V-I-L-V-A-V-L-T-A-A (SEQ ID NO: 251), V-I-L-V-A-V-L-T-I-A (SEQ ID NO: 252), V-I-L-V-A-V-L-T-V-M (SEQ ID NO: 253), V-I-L-V-A-V-L-T-V-V (SEQ ID NO: 254), V-I-L-V-A-A-L-A-A-A (SEQ ID NO: 255), V-I-L-V-A-A-L-A-I-A (SEQ ID NO: 256), V-I-L-V-A-A-L-A-V-M (SEQ ID NO: 257), V-I-L-V-A-A-L-A-V-V (SEQ ID NO: 258), V-I-L-V-A-A-L-T-A-M (SEQ ID NO: 259), V-I-L-V-A-A-L-T-A-V (SEQ ID NO: 260), V-I-L-V-A-A-L-T-I-M (SEQ ID NO: 261), V-I-L-V-A-A-L-T-I-V (SEQ ID NO: 262), V-V-M-I-G-A-L-T-V-A (SEQ ID NO: 263), V-V-M-I-S-A-L-T-V-A (SEQ ID NO: 264), V-V-M-I-A-V-L-T-V-A (SEQ ID NO: 265), V-V-M-I-A-A-L-A-V-A (SEQ ID NO: 266), V-V-M-I-A-A-L-T-A-A (SEQ ID NO: 267), V-V-M-I-A-A-L-T-I-A (SEQ ID NO: 268), V-V-M-I-A-A-L-T-V-M (SEQ ID NO: 269), V-V-M-I-A-A-L-T-V-V (SEQ ID NO: 270), V-V-M-M-G-A-L-T-V-A (SEQ ID NO: 271), V-V-M-M-S-A-L-T-V-A (SEQ ID NO: 272), V-V-M-M-A-V-L-T-V-A (SEQ ID NO: 273), V-V-M-M-A-A-L-A-V-A (SEQ ID NO: 274), V-V-M-M-A-A-L-T-A-A (SEQ ID NO: 275), V-V-M-M-A-A-L-T-I-A (SEQ ID NO: 276), V-V-M-M-A-A-L-T-V-M (SEQ ID NO: 277), V-V-M-M-A-A-L-T-V-V (SEQ ID NO: 278), V-V-M-V-G-V-L-T-V-A (SEQ ID NO: 279), V-V-M-V-G-A-L-A-V-A (SEQ ID NO: 280), V-V-M-V-G-A-L-T-A-A (SEQ ID NO: 281), V-V-M-V-G-A-L-T-I-A (SEQ ID NO: 282), V-V-M-V-G-A-L-T-V-M (SEQ ID NO: 283), V-V-M-V-G-A-L-T-V-V (SEQ ID NO: 284), V-V-M-V-S-V-L-T-V-A (SEQ ID NO: 285), V-V-M-V-S-A-L-A-V-A (SEQ ID NO: 286), V-V-M-V-S-A-L-T-A-A (SEQ ID NO: 287), V-V-M-V-S-A-L-T-I-A (SEQ ID NO: 288), V-V-M-V-S-A-L-T-V-M (SEQ ID NO: 289), V-V-M-V-S-A-L-T-V-V (SEQ ID NO: 290), V-V-M-V-A-V-L-A-V-A (SEQ ID NO: 291), V-V-M-V-A-V-L-T-A-A (SEQ ID NO: 292), V-V-M-V-A-V-L-T-I-A (SEQ ID NO: 293), V-V-M-V-A-V-L-T-V-M (SEQ ID NO: 294), V-V-M-V-A-V-L-T-V-V (SEQ ID NO: 295), V-V-M-V-A-A-L-A-A-A (SEQ ID NO: 296), V-V-M-V-A-A-L-A-I-A (SEQ ID NO: 297), V-V-M-V-A-A-L-A-V-M (SEQ ID NO: 298), V-V-M-V-A-A-L-A-V-V (SEQ ID NO: 299), V-V-M-V-A-A-L-T-A-M (SEQ ID NO: 300), V-V-M-V-A-A-L-T-A-V (SEQ ID NO: 301), V-V-M-V-A-A-L-T-I-M (SEQ ID NO: 302), V-V-M-V-A-A-L-T-I-V (SEQ ID NO: 303), V-V-L-I-G-V-L-T-V-A (SEQ ID NO: 304), V-V-L-I-G-A-L-A-V-A (SEQ ID NO: 305), V-V-L-I-G-A-L-T-A-A (SEQ ID NO: 306), V-V-L-I-G-A-L-T-I-A (SEQ ID NO: 307), V-V-L-I-G-A-L-T-V-M (SEQ ID NO: 308), V-V-L-I-G-A-L-T-V-V (SEQ ID NO: 309), V-V-L-I-S-V-L-T-V-A (SEQ ID NO: 310), V-V-L-I-S-A-L-A-V-A (SEQ ID NO: 311), V-V-L-I-S-A-L-T-A-A (SEQ ID NO: 312), V-V-L-I-S-A-L-T-I-A (SEQ ID NO: 313), V-V-L-I-S-A-L-T-V-M (SEQ ID NO: 314), V-V-L-I-S-A-L-T-V-V (SEQ ID NO: 315), V-V-L-I-A-V-L-A-V-A (SEQ ID NO: 316), V-V-L-I-A-V-L-T-A-A (SEQ ID NO: 317), V-V-L-I-A-V-L-T-I-A (SEQ ID NO: 318), V-V-L-I-A-V-L-T-V-M (SEQ ID NO: 319), V-V-L-I-A-V-L-T-V-V (SEQ ID NO: 320), V-V-L-I-A-A-L-A-A-A (SEQ ID NO: 13), V-V-L-I-A-A-L-A-I-A (SEQ ID NO: 321), V-V-L-I-A-A-L-A-V-M (SEQ ID NO: 322), V-V-L-I-A-A-L-A-V-V (SEQ ID NO: 323), V-V-L-I-A-A-L-T-A-M (SEQ ID NO: 324), V-V-L-I-A-A-L-T-A-V (SEQ ID NO: 325), V-V-L-I-A-A-L-T-I-M (SEQ ID NO: 326), V-V-L-I-A-A-L-T-I-V (SEQ ID NO: 327), V-V-L-M-G-V-L-T-V-A (SEQ ID NO: 328), V-V-L-M-G-A-L-A-V-A (SEQ ID NO: 329), V-V-L-M-G-A-L-T-A-A (SEQ ID NO: 330), V-V-L-M-G-A-L-T-I-A (SEQ ID NO: 331), V-V-L-M-G-A-L-T-V-M (SEQ ID NO: 332), V-V-L-M-G-A-L-T-V-V (SEQ ID NO: 333), V-V-L-M-S-V-L-T-V-A (SEQ ID NO: 334), V-V-L-M-S-A-L-A-V-A (SEQ ID NO: 335), V-V-L-M-S-A-L-T-A-A (SEQ ID NO: 336), V-V-L-M-S-A-L-T-I-A (SEQ ID NO: 337), V-V-L-M-S-A-L-T-V-M (SEQ ID NO: 338), V-V-L-M-S-A-L-T-V-V (SEQ ID NO: 339), V-V-L-M-A-V-L-A-V-A (SEQ ID NO: 340), V-V-L-M-A-V-L-T-A-A (SEQ ID NO: 341), V-V-L-M-A-V-L-T-I-A (SEQ ID NO: 342), V-V-L-M-A-V-L-T-V-M (SEQ ID NO: 343), V-V-L-M-A-V-L-T-V-V (SEQ ID NO: 344), V-V-L-M-A-A-L-A-A-A (SEQ ID NO: 345), V-V-L-M-A-A-L-A-I-A (SEQ ID NO: 346), V-V-L-M-A-A-L-A-V-M (SEQ ID NO: 347), V-V-L-M-A-A-L-A-V-V (SEQ ID NO: 348), V-V-L-V-G-V-L-A-V-A (SEQ ID NO: 349), V-V-L-V-G-V-L-T-A-A (SEQ ID NO: 350), V-V-L-V-G-V-L-T-I-A (SEQ ID NO: 351), V-V-L-V-G-V-L-T-V-M (SEQ ID NO: 352), V-V-L-V-G-V-L-T-V-V (SEQ ID NO: 353), V-V-L-V-G-A-L-A-A-A (SEQ ID NO: 354), V-V-L-V-G-A-L-A-I-A (SEQ ID NO: 355), V-V-L-V-G-A-L-A-V-M (SEQ ID NO: 356), V-V-L-V-G-A-L-A-V-V (SEQ ID NO: 357), V-V-L-V-G-A-L-T-A-M (SEQ ID NO: 358), V-V-L-V-G-A-L-T-A-V (SEQ ID NO: 359), V-V-L-V-G-A-L-T-I-M (SEQ ID NO: 360), V-V-L-V-G-A-L-T-I-V (SEQ ID NO: 361), V-V-L-V-S-V-L-A-V-A (SEQ ID NO: 362), V-V-L-V-S-V-L-T-A-A (SEQ ID NO: 363), V-V-L-V-S-V-L-T-I-A (SEQ ID NO: 364), V-V-L-V-S-V-L-T-V-M (SEQ ID NO: 365), V-V-L-V-S-V-L-T-V-V (SEQ ID NO: 366), V-V-L-V-S-A-L-A-A-A (SEQ ID NO: 367), V-V-L-V-S-A-L-A-I-A (SEQ ID NO: 368), V-V-L-V-S-A-L-A-V-M (SEQ ID NO: 369), V-V-L-V-S-A-L-A-V-V (SEQ ID NO: 370), V-V-L-V-S-A-L-T-A-M (SEQ ID NO: 371), V-V-L-V-S-A-L-T-A-V (SEQ ID NO: 372), V-V-L-V-S-A-L-T-I-M (SEQ ID NO: 373), V-V-L-V-S-A-L-T-I-V (SEQ ID NO: 374), V-V-L-V-A-V-L-A-A-A (SEQ ID NO: 375), V-V-L-V-A-V-L-A-I-A (SEQ ID NO: 376), V-V-L-V-A-V-L-A-V-M (SEQ ID NO: 377), V-V-L-V-A-V-L-A-V-V (SEQ ID NO: 378), V-V-L-V-A-V-L-T-A-M (SEQ ID NO: 379), V-V-L-V-A-V-L-T-A-V (SEQ ID NO: 380), V-V-L-V-A-V-L-T-I-M (SEQ ID NO: 381), V-V-L-V-A-V-L-T-I-V (SEQ ID NO: 382), V-V-L-V-A-A-L-A-A-M (SEQ ID NO: 383), V-V-L-V-A-A-L-A-A-V (SEQ ID NO: 384), V-V-L-V-A-A-L-A-I-M (SEQ ID NO: 385), V-V-L-V-A-A-L-A-I-V (SEQ ID NO: 386), V-V-L-M-A-A-L-T-A-M (SEQ ID NO: 390), V-V-L-M-A-A-L-T-A-V (SEQ ID NO: 391), V-V-L-M-A-A-L-T-I-M (SEQ ID NO: 392), V-V-L-M-A-A-L-T-I-V (SEQ ID NO: 393), and I-V-

L-V-A-A-L-T-V-A (SEQ ID NO: 394). These amino acid sequences are preferred specific embodiments of the inotropic motif comprised in a variant or fragment of the S100 protein according to the present invention.

In another preferred embodiment, the inotropic motif comprises or consists of the amino acid sequence V-[V/I]-L-[V/I]-[A/S]-[A/V]-L-[T/A]-[V/A]-A (SEQ ID NO: 387), wherein the preferred sequence is V-V-L-V-A-A-L-T-V-A (SEQ ID NO: 9), wherein preferably maximally 4, more preferably maximally 3, even more preferably maximally 2, and most preferably maximally 1 amino acid is replaced as specified above. Thus, in a particularly preferred embodiment, the inotropic motif consists of the amino acid sequence V-[V/I]-L-[V/I]-[A/S]-[A/V]-L-[T/A]-[V/A]-A (SEQ ID NO: 387), wherein the preferred sequence is V-V-L-V-A-A-L-T-V-A (SEQ ID NO: 9), wherein preferably maximally 4, more preferably maximally 3, even more preferably maximally 2, and most preferably maximally 1 amino acid is replaced with another amino acid as specified above.

In a preferred embodiment, the inotropic motif comprises or consists of an amino acid sequence selected from the group consisting of the amino acid sequences V-V-L-V-A-A-L-T-V-A (SEQ ID NO: 9), V-I-L-V-A-A-L-T-V-A (SEQ ID NO: 10), V-V-M-V-A-A-L-T-V-A (SEQ ID NO: 11), I-I-L-V-G-A-L-T-V-A (SEQ ID NO: 12), V-V-L-I-A-A-L-A-A-A (SEQ ID NO: 13), V-I-L-V—S-V-L-T-V-A (SEQ ID NO: 14), I-I-L-M-G-A-L-T-V-A (SEQ ID NO: 15), and V-V-M-V-A-A-L-T-V-V (SEQ ID NO: 16). These amino acid sequences are particularly preferred specific embodiments of the inotropic motif comprised in a peptide according to the present invention.

The S100A1 protein derived domain of the peptide of the first aspect is preferably selected from the group consisting of the amino acid sequences V-V-L-V-A-A-L-T-V (SEQ ID NO: 18), V-V-L-V-A-A-L-T (SEQ ID NO: 19), V-V-L-V-A-A-L (SEQ ID NO: 20), V-L-V-A-A-L-T-V-A (SEQ ID NO: 21), V-L-V-A-A-L-T-V (SEQ ID NO: 22), V-L-V-A-A-L-T (SEQ ID NO: 23), V-L-V-A-A-L (SEQ ID NO: 24), L-V-A-A-L-T-V-A (SEQ ID NO: 25), and L-V-A-A-L-T-V (SEQ ID NO: 26), L-V-A-A-L-T (SEQ ID NO: 27), L-V-A-A-L (SEQ ID NO: 28), V-A-A-L-T-V-A (SEQ ID NO: 29), V-A-A-L-T-V (SEQ ID NO: 30), V-A-A-L-T (SEQ ID NO: 31), and V-A-A-L (SEQ ID NO: 8).

In a most preferred embodiment, the peptide comprises or consists of an amino acid sequence selected from the group consisting of the amino acid sequences D-K-D-D-P-P-V-L-V-A-A-L-T-V-A (SEQ ID NO: 32), D-K-D-D-P-P-L-V-A-A-L-T-V-A (SEQ ID NO: 33), D-K-D-D-P-P-V-A-A-L-T-V-A (SEQ ID NO: 34), D-K-D-D-P-P-V-V-L-V-A-A-L-T-V (SEQ ID NO: 35), D-K-D-D-P-P-V-V-L-V-A-A-L-T (SEQ ID NO: 36), and D-K-D-D-P-P-V-V-L-V-A-A-L (SEQ ID NO: 37).

In another embodiment, the S100A1 protein derived domain of the peptide comprises or consists of an amino acid sequence selected from the group consisting of the amino acid sequences V-V-L-V-A-A-L-T-V (SEQ ID NO: 18), V-V-L-V-A-A-L-T (SEQ ID NO: 19), and V-V-L-V-A-A-L (SEQ ID NO: 20). Preferably, the peptide comprises or consists of an amino acid sequence selected from the group consisting of the amino acid sequences V-V-L-V-A-A-L-T-V (SEQ ID NO: 18), V-V-L-V-A-A-L-T (SEQ ID NO: 19), and V-V-L-V-A-A-L (SEQ ID NO: 20). Each of these peptides comprising or consisting of an amino acid sequence according to SEQ ID NOs 18 to 20 may further comprise the hydrophilic domain D-K-D-D-P-P linked to the N-terminal of said amino acid sequence.

The S100A1 protein derived domain of the peptides is preferably located at the C-terminus of the peptide of the first or second aspect. More preferably, said peptides do not contain more than 9 continuous amino acids comprised in the 20 amino acid C-terminus region of an S100A1 protein.

In another embodiment, the peptide further comprises a marker moiety. A marker moiety in the context of the present invention may be any moiety that allows for a straightforward detection of the peptide, such as a fluorescent label, e.g., fluorescein (for example, fluorescein isothiocyanate FITC), rhodamine (for example, tetramethylrhodamine TAMRA or its isothiocyanate derivative TRITC, sulforhodamine 101 and its sulfonylchloride form Texas Red™, and Rhodamine Red), or Alexa Fluor® dyes, a radioactive label, e.g., a radioactively labeled amino acid, or biotin. In one embodiment, the peptide of the present invention comprises a hydrophilic motif, preferably D-K-D-D-P-P (SEQ ID NO: 17), and a marker moiety, preferably FITC or rhodamine, wherein preferably the muscle function enhancing amino acid sequence is V-V-L-V-A-A-L-T-V-A (SEQ ID NO: 9), and preferably the hydrophilic motif is directly linked to the amino-terminus of the muscle function enhancing amino acid sequence.

In a preferred embodiment, the amino acid sequence of the peptides according to the present invention forms an α-helical structure.

In a particularly preferred embodiment, the peptides of the present invention are capable of penetrating cell membranes, preferably vertebrate cell membranes, even more preferably mammalian cell membranes, even more preferably mammalian muscle cell membranes, and most preferably mammalian skeletal muscle cell membranes and membranes of mammalian cardiomyocytes. Preferably, the peptides of the present invention are capable of penetrating cell membranes as defined above in a physiological environment such as in culture medium, for example, for mammalian tissue culture, and/or in body fluids such as in blood. Thus, most preferably, the peptides of the present invention are capable of penetrating cell membranes in vivo when it is administered by a parenteral administration route such as by intravenous injection.

In embodiments of the first aspect of the present invention, the nucleic acid encoding the S100 protein or the inotropic fragment or variant thereof, is comprised in a vector. Preferably, the vector is selected from the group consisting of plasmid vectors, cosmid vectors, phage vectors such as lambda phage, filamentous phage vectors, viral vectors, viral like particles, and bacterial spores. It is particularly preferred that the viral vector is selected from the group consisting of an adenoviral vector, adeno-associated viral (AAV) vector, alphaviral vector, herpes viral vector, measles viral vector, pox viral vector, vesicular stomatitis viral vector, retroviral vector and lentiviral vector. In preferred embodiments, the vector integrates into the genome, preferably into the genome of myocardial cells. In further preferred embodiments, the vector is an AAV selected from the group consisting of AAV6 and AAV9.

In preferred embodiments above described vector triggers the expression of the S100 protein or inotropic fragments or variants thereof in myocardial cells. In further preferred embodiments, the expression of the S100 protein is controlled by a heart tissue specific promoter, i.e. preferably the vector further comprises a heart tissue specific promoter. Preferably the heart tissue specific promoter is selected from the group consisting of but not limited to Cardiac Actin Enhancer/Elongation Factor 1 promoter, Cytomegolo-virus enhancer/Myosin light chain ventricle 2 promoter and Troponin.

In preferred embodiments, the vector is a viral vector which is preferably administered in a dosage of $5\times10^{10}$-$1\times10^{12}$ tvp, more preferably $1\times10^{11}$-$5\times10^{11}$ tvp, most preferably $2\times10^{11}$ tvp.

In preferred embodiments of the present invention, the intracellular level of said S100 protein is raised in at least 30% of the cells of the heart tissue of said individual. The size and amount of treated subsections and, thus the amount of heart cells expressing the S100 protein will depend on the underlying disease condition. However, it is preferred that within a treated heart region the intracellular level of S100 is raised as indicated above.

In embodiments of the present invention, the S100 protein or inotropic fragments or variants thereof, or the nucleic acid encoding said S100 protein or inotropic fragments or variants thereof, described above or below is administered through the oral, intravenous, intramucosal, intraarterial, intramusculuar or intracoronal route. Intravenous administration is preferred.

In further embodiments of the present invention, the intracellular level of said S100 protein is raised for a period of at least 7 days, more preferably of at least 10 days, and even more preferably for a period of at least 14 days. This result is preferably attained as a result of a single administration or repetitive administration.

In embodiments of the present invention, the individual is healthy or suffers from or is at risk of developing a cardiac disorder. Preferably, the cardiac disorder is associated with defective calcium cycling and/or defective contractile performance in muscle cells. In preferred embodiments the cardiac disorder is selected from the group consisting of postischemic contractile dysfunction, preferably postischemic contractile right and/or left ventricular dysfunction, congestive heart failure, preferably compensated and/or decompensated congestive heart failure, cardiogenic shock, septic shock, myocardial infarction, cardiomyopathy, dysfunction of heart valves, and ventricular disorder, such as acute or chronic right ventricular disorder. It is particularly preferred that the cardiac disorder is a primary or secondary cardiomyopathy. The primary cardiomyopathy is preferably selected from inherited cardiomyopathy and cardiomyopathy caused by spontaneous mutations. The secondary cardiomyopathy is preferably selected from ischemic cardiomyopathy caused by arteriosclerosis, dilated cardiomyopathy caused by infection or intoxication of the myocard, hypertensive heart disease caused by pulmonary arterial und/or arterial hypertension and diseases of the heart valves.

In a second aspect, the present invention relates to a S100 protein or a nucleic acid encoding said S100 protein for use in treating a cardiac disease by enhancing the cardiac power in an individual suffering from or at risk of developing said cardiac disease, wherein the concentration in the myocardium of said individual is increased to be within the therapeutic window, preferably increased to 0.5-42 µg per g of wet weight myocardium.

Preferably, the cardiac power is enhanced by improving the muscle function, contractile performance, and/or calcium handling of the heart. Preferably, the force of muscle contraction is increased. In preferred embodiments, the cardiac power is enhanced by at least 15%, preferably by at least 25%, more preferably by at least 35%, most preferably by at least 45%, and most preferably by at least 50% compared to a control setting. Preferably, the control setting is the muscle function, contractile performance, and/or calcium handling of a healthy patient or the average of a group of healthy patients. In preferred embodiments, the cardiac power is enhanced by the S100 protein or the nucleic acid encoding said S100 protein, which exhibits one or more of the functions disclosed in detail above with regard to the first aspect, selected from the list consisting of an anti-arrhythmic potential, anti-apoptotic potential, the ability to reduce calcium spark frequency, the ability to prevent and/or reduce calcium leakage from the sarcoplasmic reticulum, and the ability to restore hemodynamic function preferably in an individual suffering from heart failure.

In preferred embodiments of the second aspect, the concentration of the S100 protein in the myocardium of an individual is increased to 0.5 µg, 0.6 µg, 0.7 µg, 0.8 µg, 0.9 µg, 1 µg, 1.5 µg, 2 µg, 2.5 µg, 3 µg, 3.5 µg, 4 µg, 4.5 µg, 5 µg, 5.5 µg, 6 µg, 6.5 µg, 7 µg, 7.5 µg, 8 µg, 8.5 µg, 9 µg, 9.5 µg, 10 µg, 15 µg, 20 µg, 25 µg, 30 µg, 35 µg, 40 µg, 42 µg per g of wet weight myocardium. In preferred embodiments, the concentration in the myocardium of said individual is increased to 1-17 µg, preferably to 3-7 µg, more preferably 3.5 µg.

In further embodiments, the concentration of the S100 protein in the myocardium of an individual is increased to be below 100 µg, 90 µg, 80 µg, 70 µg, 60 µg, 50 µg, 45 µg per g of wet weight myocardium.

In embodiments of the second aspect, the S100 protein is the naturally occurring S100 protein which is preferably selected from the group consisting of S100β, S100A1, S100A2, S100A4 and S100A6. S100A1 is particularly preferred.

In embodiments of the second aspect of the present invention, the S100 protein is a fragment or variant of a naturally occurring S100 protein, which exhibits a positive inotropic action, i.e. a fragment or variant of a naturally occurring S100 protein which increases the force of muscle contraction. In preferred embodiments, the fragment or variant comprises an inotropic peptide, preferable a peptide as disclosed in detail above with regard to the first aspect of the present invention.

In embodiments of the second aspect of the present invention, the nucleic acid is comprised in a vector. Preferably, the vector is selected from the group consisting of plasmid vectors, cosmid vectors, phage vectors such as lambda phage, filamentous phage vectors, viral vectors, viral like particles, and bacterial spores. It is particularly preferred that the viral vector is selected from the group consisting of an adenoviral vector, adeno-associated viral (AAV) vector, alphaviral vector, herpes viral vector, measles viral vector, pox viral vector, vesicular stomatitis viral vector, retroviral vector and lentiviral vector. In preferred embodiments, the vector integrates into the genome, preferably into the genome of myocardial cells. In preferred embodiments, the vector is an AAV selected from the group consisting of AAV6 and AAV9.

In preferred embodiments, the expression of the S100 protein is controlled by a heart tissue specific promoter. Preferably the heart tissue specific promoter is selected from the group consisting of but not limited to Cardiac Actin Enhancer/Elongation Factor 1 promoter Cytomegolo-virus enhancer/Myosin light chain ventricle 2 promoter and Troponin.

In embodiments of the present invention, the protein or nucleic acid described above or below is administered through the oral, intravenous, intramucosal, intraarterial, intramusculuar or intracoronal route. Intravenous administration is preferred.

In preferred embodiments the vector is a viral vector which is preferably administered in a dosage of $5\times10^{10}$-$1\times10^{12}$ tvp, more preferably $1\times10^{11}$-$5\times10^{11}$ tvp, most preferably $2\times10^{11}$ tvp.

In embodiments of the present invention, the individual is healthy or suffers from or is at risk of developing a cardiac disorder. Preferably, the cardiac disorder is associated with defective calcium cycling and/or defective contractile performance in muscle cells. In preferred embodiments the cardiac disorder is selected from the group consisting of postischemic contractile dysfunction, preferably postischemic contractile right and/or left ventricular dysfunction, congestive heart failure, preferably compensated and/or decompensated congestive heart failure, cardiogenic shock, septic shock, myocardial infarction, cardiomyopathy, dysfunction of heart valves, and ventricular disorder, such as acute or chronic right ventricular disorder. It is particularly preferred that the cardiac disorder is a primary or secondary cardiomyopathy. The primary cardiomyopathy is preferably selected from inherited cardiomyopathy and cardiomyopathy caused by spontaneous mutations. The secondary cardiomyopathy is preferably selected from ischemic cardiomyopathy caused by arteriosclerosis, dilated cardiomyopathy caused by infection or intoxication of the myocard, hypertensive heart disease caused by pulmonary arterial und/or arterial hypertension and diseases of the heart valves.

In preferred embodiments of the present invention, the intracellular level of said S100 protein is raised in at least 30% of the cells of the heart tissue of said individual. The size and amount of treated subsections and, thus the amount of heart cells expressing the S100 protein will depend on the underlying disease condition. However, it is preferred that within a treated heart region the intracellular level of S100 is raised as indicated above.

In further embodiments of the present invention, the intracellular level of said S100 protein is raised for a period of at least 7 days irrespective, more preferably of at least 10 days, and even more preferably for a period of at least 14 days. This result is preferably attained as a result of a single administration or repetitive administration.

In a third aspect, the present invention relates to a pharmaceutical composition comprising at least one S100 protein or nucleic acid according to the first or second aspect of the present invention or a pharmaceutically acceptable salt thereof, and optionally a pharmaceutically acceptable excipient, carrier, and/or diluent.

In preferred embodiments, the pharmaceutical composition is for use in treating a cardiac disease by enhancing the cardiac power in an individual suffering from or at risk of developing said cardiac disease. Preferably, the cardiac power is enhanced by improving the muscle function, contractile performance, and/or calcium handling of the heart. Preferably, the force of muscle contraction is increased. In preferred embodiments, the cardiac power is enhanced by at least 15%, preferably by at least 25%, more preferably by at least 35%, most preferably by at least 45%, and most preferably by at least 50% compared to a control setting. Preferably, the control setting is the muscle function, contractile performance, and/or calcium handling of a healthy patient or the average of a group of healthy patients.

In preferred embodiments, the cardiac power is enhanced by the S100 protein or the nucleic acid encoding said S100 protein, which exhibits one or more of the functions as described in detail above, selected from the list consisting of an anti-arrhythmic potential, anti-apoptotic potential, the ability to reduce calcium spark frequency, the ability to prevent and/or reduce calcium leakage from the sarcoplasmic reticulum, and the ability to restore hemodynamic function preferably in an individual suffering from heart failure.

In embodiments of the third aspect, the S100 protein is the naturally occurring S100 protein which is preferably selected from the group consisting of S100β, S100A1, S100A2, S100A4 and S100A6. S100A1 is particularly preferred.

In embodiments of the third aspect of the present invention, the S100 protein is a fragment or variant of a naturally occurring S100 protein, which exhibits a positive inotropic action, i.e. a fragment or variant of a naturally occurring S100 protein which increases the force of muscle contraction. In preferred embodiments the fragment or variant comprises an inotropic peptide, preferable a peptide as disclosed in detail above with regard to the first aspect of the present invention.

In embodiments of the third aspect of the present invention, the nucleic acid is comprised in a vector. Preferably, the vector is selected from the group consisting of plasmid vectors, cosmid vectors, phage vectors such as lambda phage, filamentous phage vectors, viral vectors, viral like particles, and bacterial spores. It is particularly preferred that the viral vector is selected from the group consisting of an adenoviral vector, adeno-associated viral (AAV) vector, alphaviral vector, herpes viral vector, measles viral vector, pox viral vector, vesicular stomatitis viral vector, retroviral vector and lentiviral vector. In preferred embodiments, the vector integrates into the genome, preferably into the genome of myocardial cells. In preferred embodiments, the vector is an AAV selected from the group consisting of AAV6 and AAV9.

In preferred embodiments, the expression of the S100 protein is controlled by a heart tissue specific promoter. Preferably the heart tissue specific promoter is selected from the group consisting of but not limited to Cardiac Actin Enhancer/Elongation Factor 1 promoter Cytomegolo-virus enhancer/Myosin light chain ventricle 2 promoter and Troponin.

In preferred embodiments the vector is a viral vector which is preferably administered in a dosage of $5\times10^{10}$-$1\times10^{12}$ tvp, more preferably $1\times10^{11}$-$5\times10^{11}$ tvp, most preferably $2\times10^{11}$ tvp.

In embodiments of the present invention, the pharmaceutical composition is formulated as well-known to the skilled person to allow for administration via the oral, intravenous, intramucosal, intraarterial, intramusculuar or intracoronal route. Intravenous administration is preferred.

In a fourth aspect, the present invention relates to an Adeno-associated virus 6 or 9 comprising a nucleic acid encoding a S100 protein for use in treating a cardiac disease by enhancing the cardiac power in an individual, which is administered to said individual. Preferably, the cardiac power is enhanced by improving the muscle function, contractile performance, and/or calcium handling of the heart. Preferably, the force of muscle contraction is increased. In preferred embodiments, the cardiac power is enhanced by at least 15%, preferably by at least 25%, more preferably by at least 35%, most preferably by at least 45%, and most preferably by at least 50% compared to a control setting. Preferably, the control setting is the muscle function, contractile performance, and/or calcium handling of a healthy patient or the average of a group of healthy patients.

In preferred embodiments, the S100 protein is naturally occurring S100 protein is selected from the group consisting of S100β, S100A1, S100A2, S100A4 and S100A6. In further embodiments, the S100 protein is a fragment or variant of a naturally occurring S100 protein, which exhibits a positive inotropic action. In preferred embodiments the fragment or variant comprises an inotropic peptide, preferable a peptide as disclosed in detail above with regard to the first aspect of the present invention.

In preferred embodiments, the expression of the S100 protein is controlled by a heart tissue specific promoter. Preferably the heart tissue specific promoter is selected from the group consisting of but not limited to Cardiac Actin Enhancer/Elongation Factor 1 promoter Cytomegolo-virus enhancer/Myosin light chain ventricle 2 promoter and Troponin.

In a fifth aspect, the present invention relates to the use of the S100 protein or a nucleic acid encoding said S100 protein for increasing the concentration of said S100 protein in the myocardium of an individual suffering from or at risk of developing a cardiac disorder to be within the therapeutic window. In preferred embodiments, the cardiac power is enhanced by improving the muscle function, contractile performance, and/or calcium handling of the heart. Preferably, the force of muscle contraction is increased. In preferred embodiments, the cardiac power is enhanced by at least 15%, preferably by at least 25%, more preferably by at least 35%, most preferably by at least 45%, and most preferably by at least 50% compared to a control setting. Preferably, the control setting is the muscle function, contractile performance, and/or calcium handling of a healthy patient or the average of a group of healthy patients.

In preferred embodiments, the concentration in the myocardium is increased to no more than the 50 fold concentration in a healthy individual. Preferably, the concentration in the myocardium is increased to no more than the 20 fold, more preferably to no more than the 8 fold, most preferably to no more than the 4 fold concentration in a healthy individual. In preferred embodiments, the concentration in the myocardium is increased 2-50 fold, preferably 2-20 fold, more preferably 4-8 fold, most preferably 4 fold.

In further embodiments of the fifth aspect, the concentration in the myocardium is increased to 0.5-42 µg per g of wet weight myocardium. Preferably, the concentration in the myocardium is increased to 1-17 µg, more preferably to 3-7 µg, most preferably to 3.5 µg per g of wet weight myocardium.

In preferred embodiments, the S100 protein is naturally occurring S100 protein is selected from the group consisting of S100β, S100A1, S100A2, S100A4 and S100A6. In further embodiments, the S100 protein is a fragment or variant of a naturally occurring S100 protein, which exhibits a positive inotropic action. In preferred embodiments the fragment or variant comprises an inotropic peptide, preferable a peptide as disclosed in detail above with regard to the first aspect of the present invention.

In preferred embodiments of the present invention, the intracellular level of said S100 protein is raised in at least 30% of the cells of the heart tissue of said individual. The size and amount of treated subsections and, thus the amount of heart cells expressing the S100 protein will depend on the underlying disease condition. However, it is preferred that within a treated heart region the intracellular level of S100 is raised as indicated above.

In further embodiments of the present invention, the intracellular level of said S100 protein is raised for a period of at least 7 days, more preferably of at least 10 days, and even more preferably for a period of at least 14 days. This result is preferably attained as a result of a single administration or repetitive administration. In preferred embodiments, the concentration in the myocardium is increased via the administration of the S100 protein or a nucleic acid encoding said S100 protein. In embodiments of the fifth aspect, the protein or nucleic acid described above or below is administered through the oral, intravenous, intramucosal, intraarterial, intramusculuar or intracoronal route. Intravenous administration is preferred.

In embodiments of the fifth aspect of the present invention, the nucleic acid is comprised in a vector. Preferably, the vector is selected from the group consisting of plasmid vectors, cosmid vectors, phage vectors such as lambda phage, filamentous phage vectors, viral vectors, viral like particles, and bacterial spores. It is particularly preferred that the viral vector is selected from the group consisting of an adenoviral vector, adeno-associated viral (AAV) vector, alphaviral vector, herpes viral vector, measles viral vector, pox viral vector, vesicular stomatitis viral vector, retroviral vector and lentiviral vector. In preferred embodiments, the vector integrates into the genome, preferably into the genome of myocardial cells. In preferred embodiments, the vector is an AAV selected from the group consisting of AAV6 and AAV9.

In preferred embodiments, the expression of the S100 protein is controlled by a heart tissue specific promoter. Preferably the heart tissue specific promoter is selected from the group consisting of but not limited to Cardiac Actin Enhancer/Elongation Factor 1 promoter Cytomegolo-virus enhancer/Myosin light chain ventricle 2 promoter and Troponin.

In preferred embodiments the vector is a viral vector which is preferably administered in a dosage of $5\times10^{10}$-$1\times10^{12}$ tvp, more preferably $1\times10^{11}$-$5\times10^{11}$ tvp, most preferably $2\times10^{11}$ tvp.

In a sixth aspect, the present invention relates to a method of increasing the concentration of the S100 protein in the myocardium of an individual suffering from or at risk of developing a cardiac disorder to be within the therapeutic window. In preferred embodiments, the method is for use in treating a cardiac disease by enhancing the cardiac power in an individual suffering from or at risk of developing said cardiac disease. Preferably the cardiac power is enhanced by improving the muscle function, contractile performance, and/or calcium handling of the heart. Preferably, the force of muscle contraction is increased. In preferred embodiments, the cardiac power is enhanced by at least 15%, preferably by at least 25%, more preferably by at least 35%, most preferably by at least 45%, and most preferably by at least 50% compared to a control setting. Preferably, the control setting is the muscle function, contractile performance, and/or calcium handling of a healthy patient or the average of a group of healthy patients.

In preferred embodiments, the S100 protein is naturally occurring S100 protein is selected from the group consisting of S100β, S100A1, S100A2, S100A4 and S100A6. In further embodiments, the S100 protein is a fragment or variant of a naturally occurring S100 protein, which exhibits a positive inotropic action. In preferred embodiments the fragment or variant comprises an inotropic peptide, preferable a peptide as disclosed in detail above with regard to the first aspect of the present invention.

In embodiments of the sixth aspect, the concentration of the S100 protein in the myocardium of said individual is increased to no more than 50 fold, by administering a vector, comprising a nucleic acid encoding said S100 protein or said inotropic peptide thereof. In preferred embodiments, the concentration of the S100 protein in the myocardium of said individual is increased 2-50 fold, preferably 2-20 fold, more preferably 4-8 fold, most preferably 4 fold. In further embodiments, the concentration of S100 or an inotropic peptide thereof in the myocardium of said individual is increased to 0.5-42 µg per g of wet weight myocardium. In preferred embodiments, the concentration of S100 or an inotropic peptide thereof in the myocardium of said individual is increased to 1-17 µg, preferably to 3-7 µg, more preferably 3.5 µg per g of wet weight myocardium.

In preferred embodiments the concentration is in the myocardium is increased via the administration of the S100 protein or a nucleic acid encoding said S100 protein to said individual. Thus, in preferred embodiments, the method of increasing the concentration of the S100 protein in the myocardium comprises the step of administering the protein or nucleic acid described above or below to said individual, preferably through the oral, intravenous, intramucosal, intraarterial, intramusculuar or intracoronal route. Intravenous administration is preferred.

Preferably, the vector is selected from the group consisting of plasmid vectors, cosmid vectors, phage vectors such as lambda phage, filamentous phage vectors, viral vectors, viral like particles, and bacterial spores. In preferred embodiments, the vector is a viral vector. It is particularly preferred that the viral vector is selected from the group consisting of an adenoviral vector, adeno-associated viral (AAV) vector, alphaviral vector, herpes viral vector, measles viral vector, pox viral vector, vesicular stomatitis viral vector, retroviral vector and lentiviral vector. In preferred embodiments, the vector integrates into the genome, preferably into the genome of myocardial cells. In preferred embodiments, the vector is an AAV selected from the group consisting of AAV6 and AAV9. In preferred embodiments, the expression of the S100 protein is controlled by a heart tissue specific promoter. Preferably the heart tissue specific promoter is selected from the group consisting of but not limited to Cardiac Actin Enhancer/Elongation Factor 1 promoter Cytomegolo-virus enhancer/Myosin light chain ventricle 2 promoter and Troponin.

In preferred embodiments, a vector is administered, preferably a viral vector which is preferably administered in a dosage of $5 \times 10^{10}$-$1 \times 10^{12}$ tvp, more preferably $1 \times 10^{11}$-$5 \times 10^{11}$ tvp, most preferably $2 \times 10^{11}$ tvp.

In preferred embodiments of the present invention, the intracellular level of said S100 protein is raised in at least 30% of the cells of the heart tissue of said individual. The size and amount of treated subsections and, thus the amount of heart cells expressing the S100 protein will depend on the underlying disease condition. However, it is preferred that within a treated heart region the intracellular level of S100 is raised as indicated above.

In a seventh aspect, the present invention relates to a method of treating an individual suffering from or at risk of developing a cardiac disorder by increasing the concentration of the S100 protein in the myocardium of said individual to be within the therapeutic window. In preferred embodiments, the cardiac power is enhanced in said individual. Preferably the cardiac power is enhanced by improving the muscle function, contractile performance, and/or calcium handling of the heart. Preferably, the force of muscle contraction is increased. In preferred embodiments, the cardiac power is enhanced by at least 15%, preferably by at least 25%, more preferably by at least 35%, most preferably by at least 45%, and most preferably by at least 50% compared to a control setting. Preferably, the control setting is the muscle function, contractile performance, and/or calcium handling of a healthy patient or the average of a group of healthy patients.

In preferred embodiments, the S100 protein is naturally occurring S100 protein is selected from the group consisting of S100β, S100A1, S100A2, S100A4 and S100A6. In further embodiments, the S100 protein is a fragment or variant of a naturally occurring S100 protein, which exhibits a positive inotropic action. In preferred embodiments the fragment or variant comprises an inotropic peptide, preferable a peptide as disclosed in detail above with regard to the first aspect of the present invention.

In embodiments of the seventh aspect, the concentration of the S100 protein in the myocardium of said individual is increased to no more than 50 fold, by administering a vector, comprising a nucleic acid encoding said S100 protein or said inotropic peptide thereof. In preferred embodiments, the concentration of the S100 protein in the myocardium of said individual is increased 2-50 fold, preferably 2-20 fold, more preferably 4-8 fold, most preferably 4 fold. In further embodiments, the concentration of S100 or an inotropic peptide thereof in the myocardium of said individual is increased to 0.5-42 µg per g of wet weight myocardium. In preferred embodiments, the concentration of S100 or an inotropic peptide thereof in the myocardium of said individual is increased to 1-17 µg, preferably to 3-7 µg, more preferably 3.5 µg per g of wet weight myocardium.

Preferably, the vector is selected from the group consisting of plasmid vectors, cosmid vectors, phage vectors such as lambda phage, filamentous phage vectors, viral vectors, viral like particles, and bacterial spores. In preferred embodiments, the vector is a viral vector. It is particularly preferred that the viral vector is selected from the group consisting of an adenoviral vector, adeno-associated viral (AAV) vector, alphaviral vector, herpes viral vector, measles viral vector, pox viral vector, vesicular stomatitis viral vector, retroviral vector and lentiviral vector. In preferred embodiments, the vector integrates into the genome, preferably into the genome of myocardial cells. In preferred embodiments, the vector is an AAV selected from the group consisting of AAV6 and AAV9.

In preferred embodiments, the expression of the S100 protein is controlled by a heart tissue specific promoter. Preferably the heart tissue specific promoter is selected from the group consisting of but not limited to Cardiac Actin Enhancer/Elongation Factor 1 promoter Cytomegolo-virus enhancer/Myosin light chain ventricle 2 promoter and Troponin.

In embodiments of the present invention, the protein or nucleic acid described above or below is administered through the oral, intravenous, intramucosal, intraarterial, intramusculuar or intracoronal route. Intravenous administration is preferred.

In preferred embodiments; the vector is a viral vector which is preferably administered in a dosage of $5 \times 10^{10}$-$1 \times 10^{12}$ tvp, more preferably $1 \times 10^{11}$-$5 \times 10^{11}$ tvp, most preferably $2 \times 10^{11}$ tvp.

EXAMPLES

The development of antibody-based detection methods such as Enzyme-linked immunosorbent assay (ELISA) for the S100 protein allows for the determination of the physiological as well as therapeutically active amounts of the S100 protein in the myocardium and thus, allows to determine the effective dosage regime for the S100 protein. The use of large animal models such as pigs (*Sus scrofa*), which exhibit equivalent parameters regarding the weight, size, anatomy and physiological cardiac function as humans, allows for a direct transferability of the therapeutic window and effects determined in these assays, to the clinical application in humans.

Example 1: Characterization of S100A1 Cardiac Expression Dose-Dependency in Normal Myocardium; Small Animal Models The range of myocardial S100A1 protein expression that conveys cardiac performance enhancement in mice with normal cardiac function is determined by the use of AAV9-mediated human S100A1 cDNA myocardial delivery. The cardiac performance with respect to gradually increasing myocardial S100A1 protein levels was assessed in normal 6 months old C57B/6 mice with the aim to determine the efficient dose range of S100A1 protein concentrations in normal myocardium for acute and sustained enhancement of cardiac function in vivo. Techniques used are described in detail in Voelkers et al. Circ Res (2011) 108; 27-39 employing intravenous application of AAV9 for a gradual increase in global myocardial transgene expression; in Most et al. JCI (2004) 114; 1550-1563 for echocardiography for cardiac function analysis. AAV9-S100A1 and corresponding control vector generation and use of the cardiac specific promoter element to drive expression of both transgenes is described in detail in Pleger et al. Science Translational Medicine (2011) 3, 92ra64. The S100A1 overexpression (2, 4, 8, 20 and 50 fold) corresponds to intravenous AAV9-S100A1 dosages (total virus particles; tvp) $5\times10^{10}$, $1\times10^{11}$, $2\times10^{11}$, $5\times10^{11}$, $1\times10^{12}$ respectively. Total S100A1 protein amount in murine myocardium was assessed by ELISA as described in detail in Example 4. S100A1 concentrations were measured by Western Blot as described by Most et al. JCI (2004) 114; 1550-1563 using a custom-made rabbit anti-S100A1 polyclonal IgG antibody (SA 5632). 0.83 µg S100A1 protein/g wet weight myocardium equals normal S100A1 values in healthy left ventricular myocardium and has been set as 1 for relative comparison. Conversion between n-fold relative changes assessed by WB and total myocardial S100A1 protein measured by ELISA is given by the second x-axis. FIG. 1 (left) shows that the left ventricular ejection fraction (LV EF %) in anesthetized mice peaks at an approximately 4-6 fold increase of cardiac S100A1 protein concentrations compared to normal S100A1 protein levels (assessed by WB). Further increase in cardiac S100A1 protein concentrations results in loss of the S100A1-mediated contractile performance enhancement. The biologically effective S100A1 dosages fall into the range between 0.83 to 41.5 µg S100A1 protein/g wet weight myocardium and peak actions relate to 3.32 µg S100A1 protein (assessed by ELISA).

Example 2: Characterization of S100A1 Cardiac Expression Dose-Dependency in DISEASED Myocardium; Small Animal Models The therapeutic window of viral-based re-expression and augmentation of myocardial S100A1 protein concentrations in mice with impaired cardiac function was then analysed. The results for S100A1 dose-dependency in normal mice provides the basis for determining the therapeutic window of S100A1 re-expression in C57B/6 mice with impaired cardiac function due to experimental myocardial infarction through temporary occlusion of the left anterior coronary artery as technically described in detail in Brinks et al. Circ Res (2010) 107; 1140-1149. Techniques for intravenous application of AAV9 for gradual increases in global myocardial transgene expression are described in detail in Voelkers et al. Circ Res (2011) 108; 27-39; in Most et al. JCI (2004) 114; 1550-1563 echocardiography for cardiac function analysis. AAV9-S100A1 and corresponding control vector generation and use the cardiac specific promoter element to drive expression of both transgenes is described in detail in Pleger et al. Science Translational Medicine (2011) 3, 92ra64. The S100A1 re-/overexpression 0.7, 2, 4, 8, 20 and 50 fold corresponds to intravenous AAV9-S100A1 dosages (total virus particles; tvp) $2\times10^{10}$', $5\times10^{10}$, $1\times10^{11}$, $2\times10^{11}$, $5\times10^{11}$, $1\times10^{12}$ respectively. Total S100A1 protein amount in murine myocardium was assessed by ELISA as described in detail in Example 4. S100A1 concentrations were measured by Western Blot as described by Most et al. JCI (2004) 114; 1550-1563 using a custom-made rabbit anti-S100A1 polyclonal IgG antibody (SA 5632). Total S100A1 protein amounts below 0.83 µg S100A1 protein/g wet weight myocardium characterizes failing left ventricular myocardium with impaired contractile function. Conversion between n-fold relative changes assessed by WB and total myocardial S100A1 protein measured by ELISA is given by the second x-axis.

Figure 2:
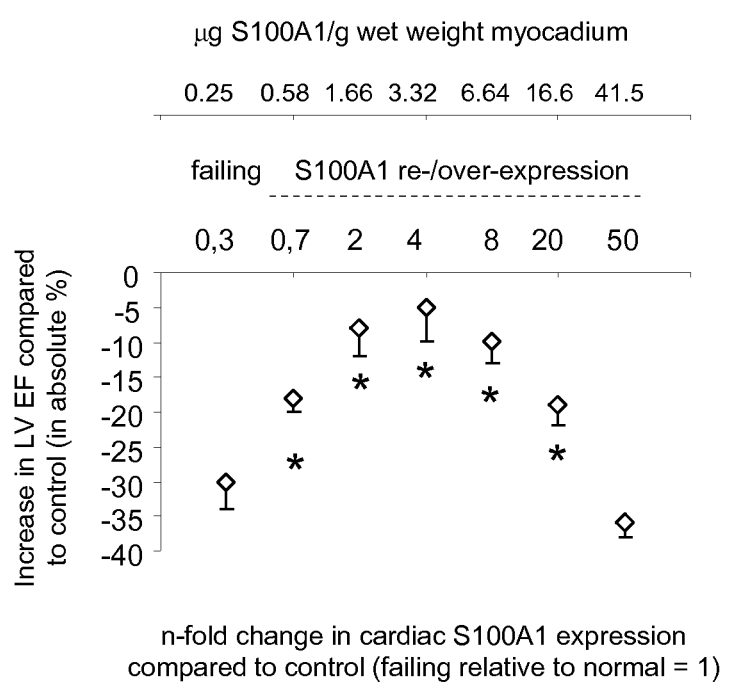
Figure 3:
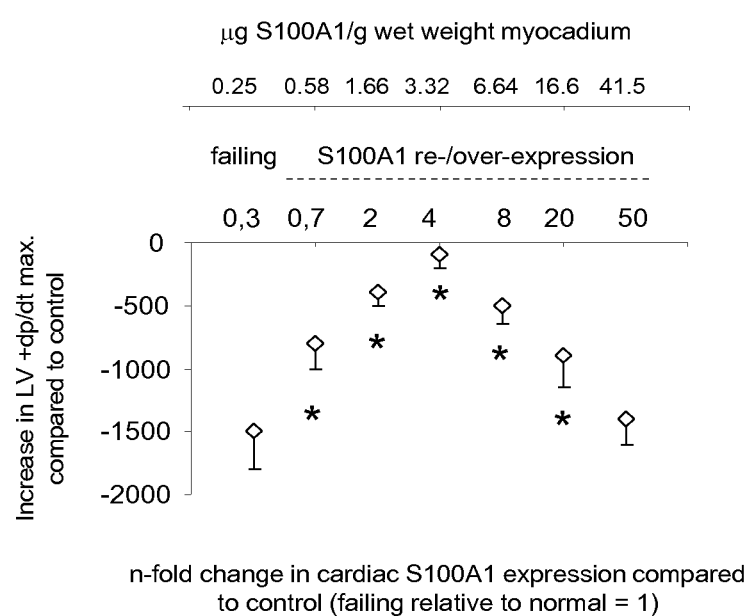
Figure 4:
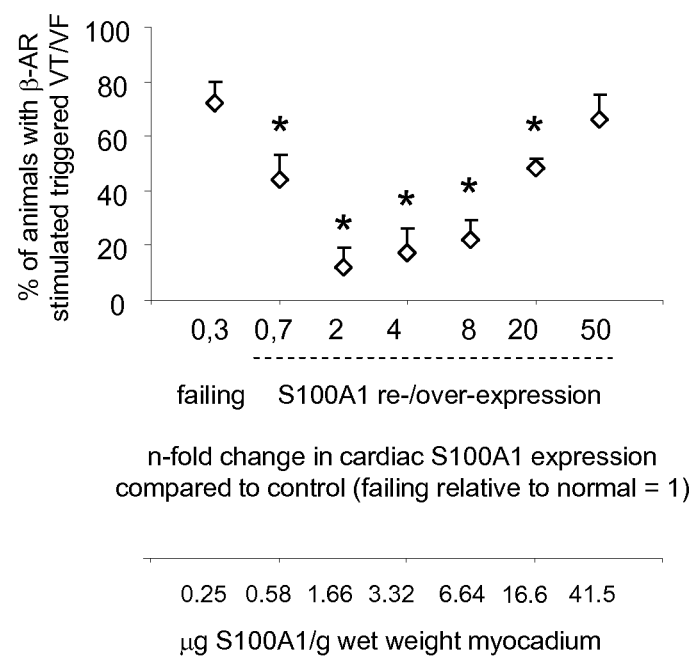

FIG. 2 and FIG. 3 show that S100A1 re-expression and over-expression in failing mouse hearts restores and improves cardiac function assessed by LV EF % (FIG. 2) and left ventricular catheterization with maximal LV pressure rise increase (LV+dp/dt max) (FIG. 3) as surrogate marker for invasive hemodynamic. Therapeutic actions peak around 4-fold S100A1 overexpression relating to a total S100A1 protein amount of 3.32 µg S100A1 protein/g wet weight myocardium. The S100A1 therapeutic window of contractile performance enhancement falls into the range between 0.25 and 41.4 µg S100A1 protein/g wet weight myocardium. Values reflect the relative range from re-expression to normal and up to 50 fold relative increase in S100A1 protein levels. Further increase in cardiac S100A1 protein concentrations results in the complete loss of S100A1's therapeutic performance enhancement FIG. 4 depicts that S100A1 re-expression and over-expression in failing mouse hearts prevents β-adrenergically triggered ventricular tachyarrhythmias including re-expression to normal and up to a 50 fold increase in S100A1 protein levels. The S100A1 therapeutic window against β-adrenergically triggered ventricular tachyarrhythmias falls into the range between 0.25 and 41.4 µg S100A1 protein/g wet weight myocardium. Values reflect the relative range from re-expression to normal and up to 50 fold relative increase in myocardial S100A1 protein levels. Further increase in cardiac S100A1 protein concentrations results in complete loss of S100A1's therapeutic anti-arrhythmic actions.

Figure 5:
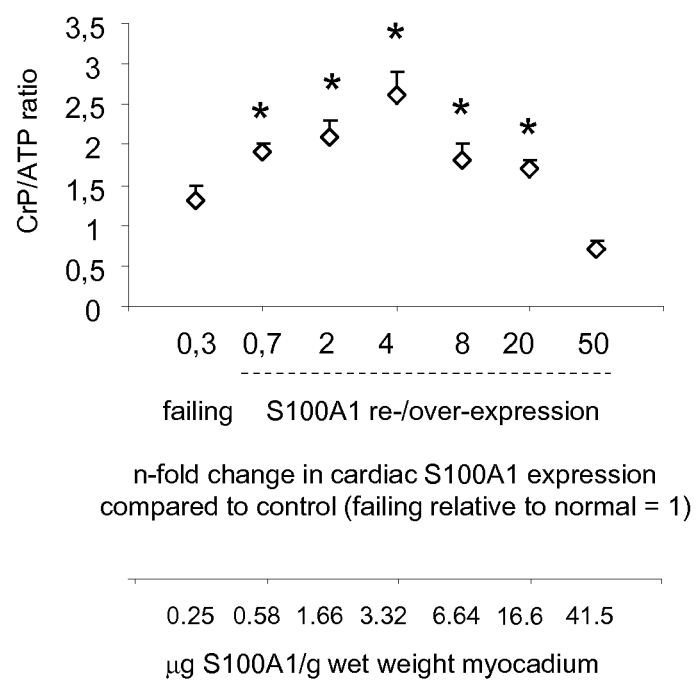

FIG. 5 explains that S100A1 re-expression and over-expression in failing mouse hearts improves the CrP/ATP ratio as surrogate for cardiac metabolism restoration including re-expression to normal and up to a 50 fold increase in S100A1 protein levels. The S100A1 therapeutic window against β-adrenergically triggered ventricular tachyarrhythmias falls into the range between 0.25 and 41.4 µg S100A1 protein/g wet weight myocardium. Values reflect the relative range from re-expression to normal and up to 50 fold relative increase in S100A1 protein levels. Further increase in cardiac S100A1 protein concentrations results in complete loss of S100A1's therapeutic anti-arrhythmic actions.

Example 3: Large Animal Models

This Example details the therapeutic window of viral-based re-expression and augmentation of myocardial S100A1 protein concentrations in domestic pigs with impaired cardiac function. The results for S100A1 dose-dependency in heart failure mice provide the base for determining the therapeutic window of S100A1 re-expression animal models that approximate human weight, size and cardiovascular anatomy and pathophysiology. Post-ischemic heart failure in pigs was induced by experimental myocardial infarction through temporary occlusion of the left circumflex coronary artery by percutaneous balloon occlusion. S100A1 re-expression and overexpression was achieved by retrograde intravenous application of increasing dosages of AAV6-S100A1 with S100A1 expression controlled by a cardiac specific promoter element. Analytical techniques and molecular tools used to this end are described in detail in Pleger et al. Science Translational Medicine (2011) 3, 92ra64. AAV6 was used in addition to AAV9 exploiting its greater myocardial transduction efficacy of AAV6 to achieve increasing myocardial S100A1 protein concentrations. S100A1 re-/overexpression 1.6, 6, 20 and 50 fold corresponds to intravenous AAV9-S100A1 dosages (total virus particles; tvp) of $1.5 \times 10^{13}$ (1.6-fold) and AAV6-S100A1 dosages of $1.5 \times 10^{11}$ (6-fold), $1.5 \times 10^{12}$ (20 fold) and $1.5 \times 10^{13}$ (50-fold), respectively.

Figure 6:
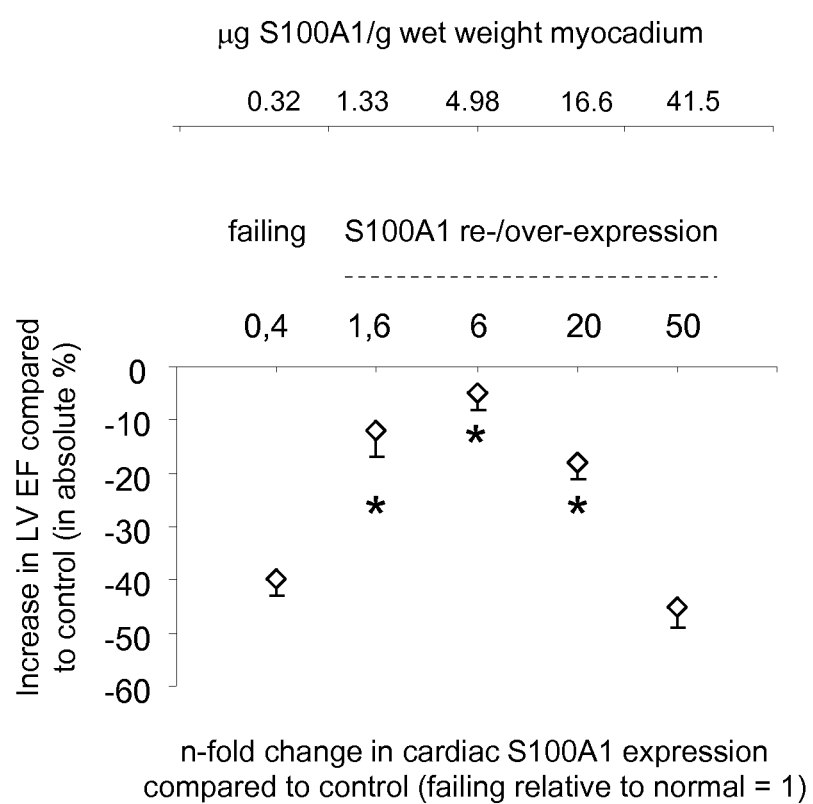
Figure 7:
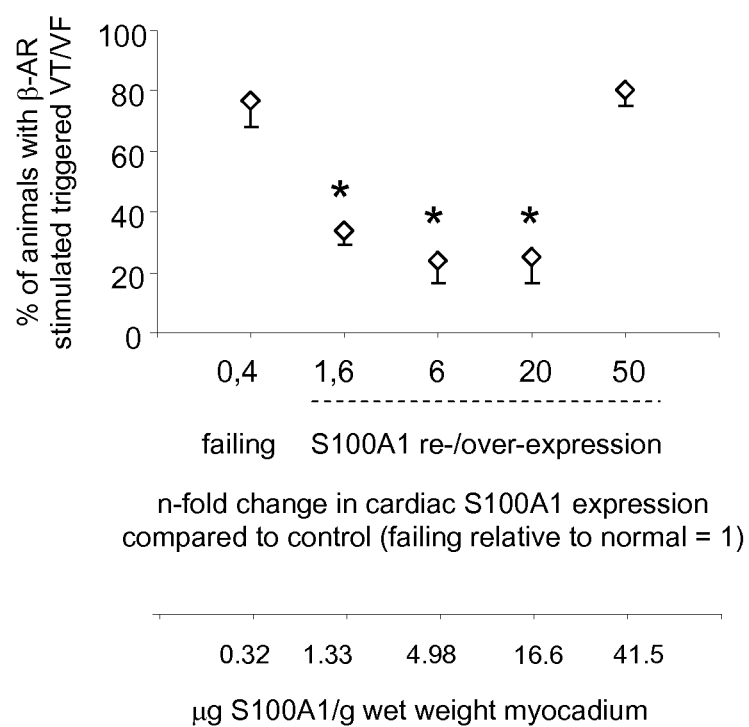

FIG. 6 and FIG. 7 show that S100A1 re-expression and over-expression in failing pig hearts restores and improves cardiac function assessed by LV EF % and left ventricular catheterization with LV+dp/dt max as surrogate for invasive hemodynamic including re-expression to normal and up to a 50 fold increase in S100A1 protein levels. The S100A1 therapeutic window against β-adrenergically triggered ventricular tachyarrhythmias falls into the range between 0.32 and 41.4 μg S100A1 protein/g wet weight myocardium. Values reflect the relative range from re-expression to normal and up to 50 fold relative increase in S100A1 protein levels. Further increase in cardiac S100A1 protein concentrations results in complete loss of S100A1's therapeutic actions.

Figure 8:
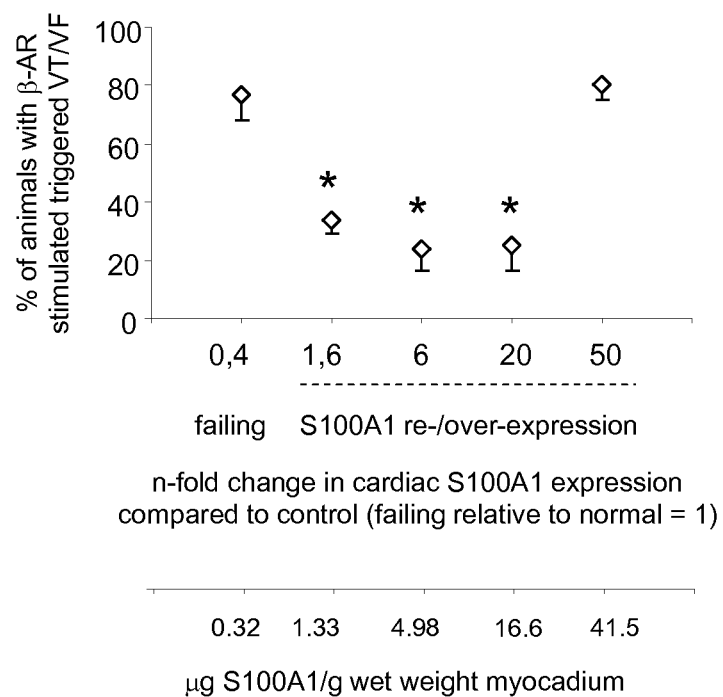
Figure 9:
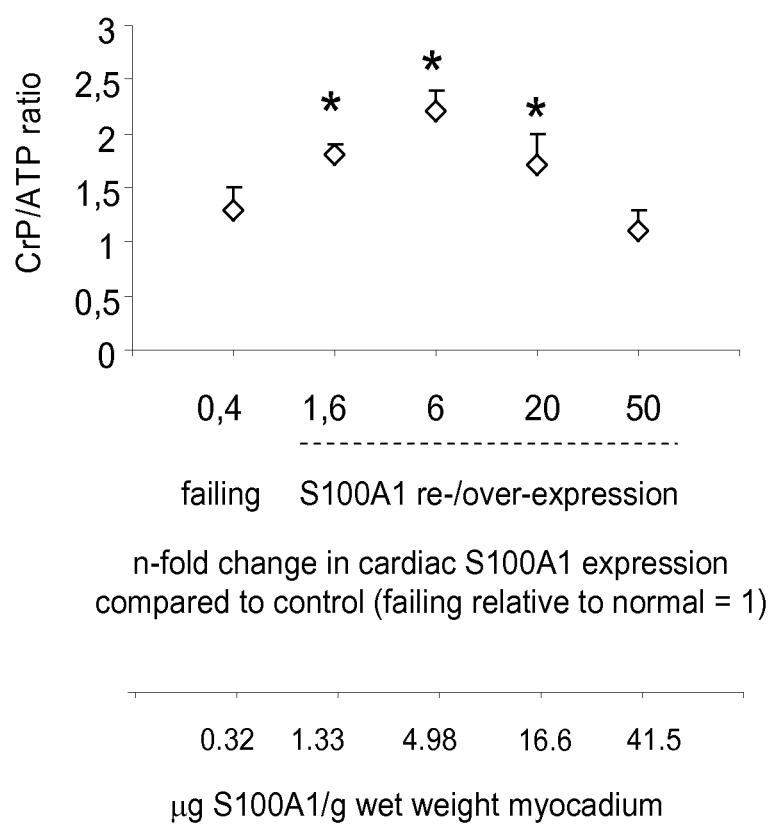

FIG. 8 depicts that S100A1 re-expression and over-expression in failing mouse hearts prevents β-adrenergically triggered ventricular tachyarrhythmias including re-expression to normal and up to a 50 fold increase in S100A1 protein levels. The S100A1 therapeutic window against β-adrenergically triggered ventricular tachyarrhythmias falls into the range between 0.32 and 41.4 μg S100A1 protein/g wet weight myocardium. Values reflect the relative range from re-expression to normal and up to 50 fold relative increase in S100A1 protein levels. Further increase in cardiac S100A1 protein concentrations results in complete loss of S100A1's therapeutic actions FIG. 9 explains that S100A1 re-expression and over-expression in failing pig myocardium improves the CrP/ATP as a surrogate for cardiac metabolism restoration including re-expression to normal and up to a 50 fold increase in S100A1 protein levels. The S100A1 therapeutic window against β-adrenergically triggered ventricular tachyarrhythmias falls into the range between 0.32 and 41.4 μg S100A1 protein/g wet weight myocardium. Values reflect the relative range from re-expression to normal and up to 50 fold relative increase in S100A1 protein levels.

Example 4: Methodology for Assessment of Total Myocardial S100A1 Protein Levels

The detection of S100A1 was performed by custom-made enzyme-linked immunosorbent assay (ELISA). 500 mg of snap-frozen left ventricular myocardium was homogenized in 2.5 ml ice cold buffer (phosphate buffered saline (PBS), pH 7.4, 5 mM EGTA, 5 mM EDTA, protease inhibitor cocktail I and II (Sigma Aldrich)) using an Ultra-Turrax T25 at 24.000 rpm (5 times, 30 seconds). Samples were then centrifuged at 5.000 rpm for 10 min at room temperature. The supernatant was collected and stored at −80° C. For ELISA measurement, a microtiter plate (Maxisorb, Nunc) was coated with the capture antibody (anti-S100oα rabbit polyclonal, abcam, ab11428). Therefore 100 μl of a capture antibody solution (2 μg/ml in coating solution, #80050, Alpha Diagnostic International) were loaded into the wells and incubated at 4° C. over night. Next day, each well was washed 3 times with wash solution (#80080, Alpha Diagnostic International). Thereafter, 300 μl of blocking solution (#80060, Alpha Diagnostic International) were added. After 3 hrs of incubation, wells were washed with wash solution. 100 μl of the serum samples (diluted 2:1 in sample diluent, HEPES 23.8 g/l, BSA 10 g/l, NaCl 5.84 g/l, Tween-20 0.1% in ddH$_2$O) were added to the corresponding wells in duplicates and incubated at 4° C. over night. A standard curve was included (2.8 ng/ml, 5.6 ng/ml, 28 ng/ml, 56 ng/ml, 140 ng/ml of recombinant human S100A1). Next day, wells were washed and 100 μl of the detection antibody (human S100A1 affinity purified polyclonal sheep IgG, R&D Systems) diluted 1:5000 in PBS (NaCl 8 g/l, KCl 0.2 g/l, Na$_2$HPO$_4$ 1.42 g/l, KH$_2$PO$_4$ 0.245 g/l, Tween-20 5% in ddH$_2$O) were added to the wells. After 3 hrs of incubation at room temperature and washing, 100 μl of a horseradish peroxidase conjugated revealing antibody (donkey anti-sheep IgG-HRP, sc-2473, Santa Cruz) diluted 1:1000 in PBS were added and the plate was incubated for 2 hrs at room temperature. After washing, 100 μl of TMB (3,3',5,5'-Tetramethylbenzidin)-substrate (#80091, Alpha Diagnostic International) were pipetted into the wells. After 20 min of incubation, 50 μl of stop solution (#80100, Alpha Diagnostic International) were added. The optical density of each well was measured with a multiplate reader (Multiskan Spectrum, Thermo Fisher Scientific) at 450 nm and corrected at 570 nm.

The invention claimed is:

1. A method for improving cardiac function in a human suffering from ischemic heart failure comprising: intravenously administering to a human suffering from ischemic heart failure an AAV6 vector comprising a nucleic acid encoding an S100A1 protein, wherein the AAV6 vector is administered in a dosage of $5\times10^{10}$-$1\times10^{12}$ total viral particles (tvp),
wherein expression of the nucleic acid results in the increase in the concentration of the S100A1 protein in the myocardium of the human suffering from ischemic heart failure by 2-20 fold compared to a concentration of S100A1 protein in a control human, whereby said increase in S100A1 protein leads to improved cardiac function.

2. The method according to claim 1, wherein the human suffers from a cardiac disorder associated with defective calcium cycling and/or defective contractile performance in muscle cells.

3. The method according to claim 1, wherein the human suffers from a cardiac disorder selected from the group consisting of postischemic contractile dysfunction, congestive heart failure, cardiogenic shock, septic shock, myocardial infarction, cardiomyopathy, dysfunction of heart valves, and ventricular disorder.

4. The method according to claim 1, wherein the human suffers from a primary or secondary cardiomyopathy.

5. The method according to claim 4, wherein the human suffers from primary cardiomyopathy, and wherein the primary cardiomyopathy is selected from inherited cardiomyopathy and cardiomyopathy caused by spontaneous mutations.

6. The method according to claim 4, wherein the human suffers from secondary cardiomyopathy, and wherein the secondary cardiomyopathy is selected from ischemic cardiomyopathy caused by arteriosclerosis, dilated cardiomyopathy caused by infection or intoxication of the myocardium, hypertensive heart disease caused by pulmonary arterial and/or arterial hypertension and diseases of the heart valves.

7. The method of claim 1, wherein the intracellular level of said S100 A1 protein is raised in at least 30% of the cells of the heart tissue of said human.

8. The method of claim 1, wherein the intracellular level of said S100A1 protein is raised for a period of at least 7 days.

* * * * *